United States Patent
Liu et al.

(10) Patent No.: US 9,464,985 B2
(45) Date of Patent: Oct. 11, 2016

(54) PLASMON RESONANCE IMAGING APPARATUS HAVING NANO-LYCURGUS-CUP ARRAYS AND METHODS OF USE

(71) Applicant: The Board of Trustees of the University of Illinois, Urbana, IL (US)

(72) Inventors: Gang Logan Liu, Champaign, IL (US); Manas Ranjan Gartia, Urbana, IL (US); Austin Yin Kyai Hsiao, Sunnyvale, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 387 days.

(21) Appl. No.: 14/156,836

(22) Filed: Jan. 16, 2014

(65) Prior Publication Data

US 2014/0206101 A1    Jul. 24, 2014

Related U.S. Application Data

(60) Provisional application No. 61/753,229, filed on Jan. 16, 2013, provisional application No. 61/810,411, filed on Apr. 10, 2013.

(51) Int. Cl.
*G01N 33/551* (2006.01)
*G01N 21/41* (2006.01)
*G01N 21/552* (2014.01)

(52) U.S. Cl.
CPC ............ *G01N 21/41* (2013.01); *G01N 21/554* (2013.01)

(58) Field of Classification Search
None
See application file for complete search history.

(56) References Cited

U.S. PATENT DOCUMENTS

| | | | | |
|---|---|---|---|---|
| 7,705,280 | B2 * | 4/2010 | Nuzzo | G01N 21/554 250/208.1 |
| 8,445,188 | B2 * | 5/2013 | Mohseni | G03F 7/20 430/324 |
| 2009/0323060 | A1 * | 12/2009 | Knipp | G01J 3/02 356/327 |
| 2012/0112165 | A1 * | 5/2012 | Charlton | H01L 27/14603 257/21 |
| 2012/0156100 | A1 * | 6/2012 | Tsai | G01N 21/6428 422/82.08 |
| 2013/0065777 | A1 * | 3/2013 | Altug | G01N 21/554 506/9 |
| 2013/0260472 | A1 * | 10/2013 | Holt | G01N 33/48721 436/149 |
| 2014/0367589 | A1 * | 12/2014 | Chiou | B82Y 15/00 250/458.1 |
| 2015/0005197 | A1 * | 1/2015 | Kennedy | G01N 21/6452 506/14 |

OTHER PUBLICATIONS

Brolo et al., "Surface Plasmon Sensor Based on the Enhanced Light Transmission through Arrays of Nanoholes in Gold Films", Langmuir, 20:4813-4815 (2004).

(Continued)

*Primary Examiner* — Chris L Chin
(74) *Attorney, Agent, or Firm* — McDonnell Boehnen Hulbert & Berghoff LLP

(57) ABSTRACT

Apparatus and methods are disclosed that are configured to permit nanoplasmonic spectroscopy sensing in the form of colorimetric sensing. An example apparatus involves: (a) an array layer having a top surface and a bottom surface, wherein a plurality of nanoholes are defined in the top surface of the array layer, wherein the plurality of nanoholes each have at least one sidewall surface and a bottom surface, (b) a thin metal film disposed on the top surface of the array layer and on the bottom surface of each of the plurality of nanoholes, and (c) a plurality of nanoparticles disposed on the at least one sidewall surface of the plurality of nanoholes.

20 Claims, 47 Drawing Sheets
(14 of 47 Drawing Sheet(s) Filed in Color)

(56) References Cited

OTHER PUBLICATIONS

Chanda et al., "Coupling of plasmonic and optical cavity modes in quasi-three-dimensional plasmonic crystals", Nature Communications (2011).
Ebbesen et al., "Extraordinary optical transmission through sub-wavelength hole arrays", Nature, 391:667-669 (1998).
Fernandez et al., "Use of interference lithography to pattern arrays of submicron resist structures for field emission flat panel displays", Journal of Vacuum Science & Technology B, 15:729-735 (1997).
Gartia et al., "Rigorous surface enhanced Raman spectral characterization of large-area high-uniformity silver-coated tapered silica nanopillar arrays", Nanotechnology, 21:395701 (2010).
Genet et al., "Light in tiny holes", Nature, 445:39-46 (2007).
Lee et al., "High-fidelity Optofluidic On-Chip Sensors Using Well-Defined Gold Nanowell Crystals", Analytical Chemistry, 83:9174-9180 (2011).
Yang et al., "Enhanced Optical Transmission Mediated by Localized Plasmons in Anisotropic Three-Dimensional Nanohole Arrays", Nano Lett, 10:3173-3178 (2010).
Stewart et al., "Quantitative multispectral biosensing and 1D imaging using quasi-3D plasmonic crystals", PNAS, 103 (46):17143-17148 (2006).
Yanik et al., "Seeing protein monolayers with naked eye through plasmonic Fano resonances", PNAS, 108 (29):11784-11789 (2011).
McMahon et al., "Tailoring the sensing capabilities of nanohole arrays in gold films with Rayleigh anomaly-surface plasmon polaritons" Optics Express, 15:18119-18129 (2007).
Xu et al., "Structural Colors: From Plasmonic to Carbon Nanostructures", Small, 7(22):3128-3136 (2011).

\* cited by examiner

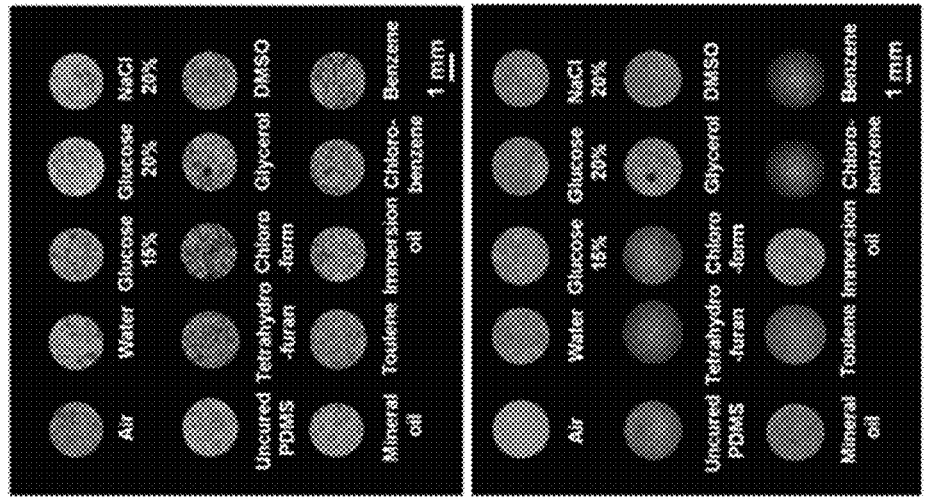
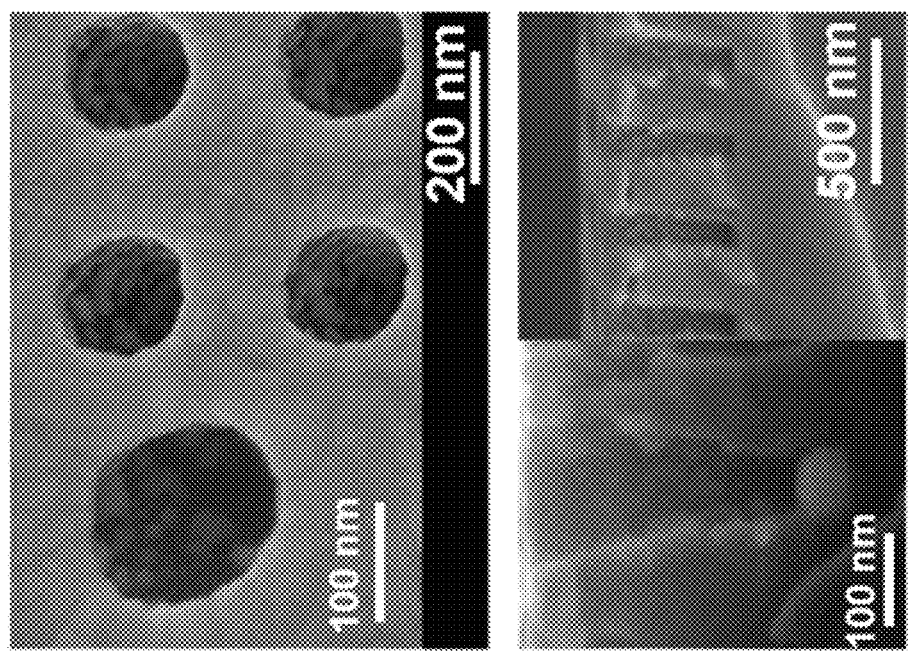
Figure 1D
Figure 1C

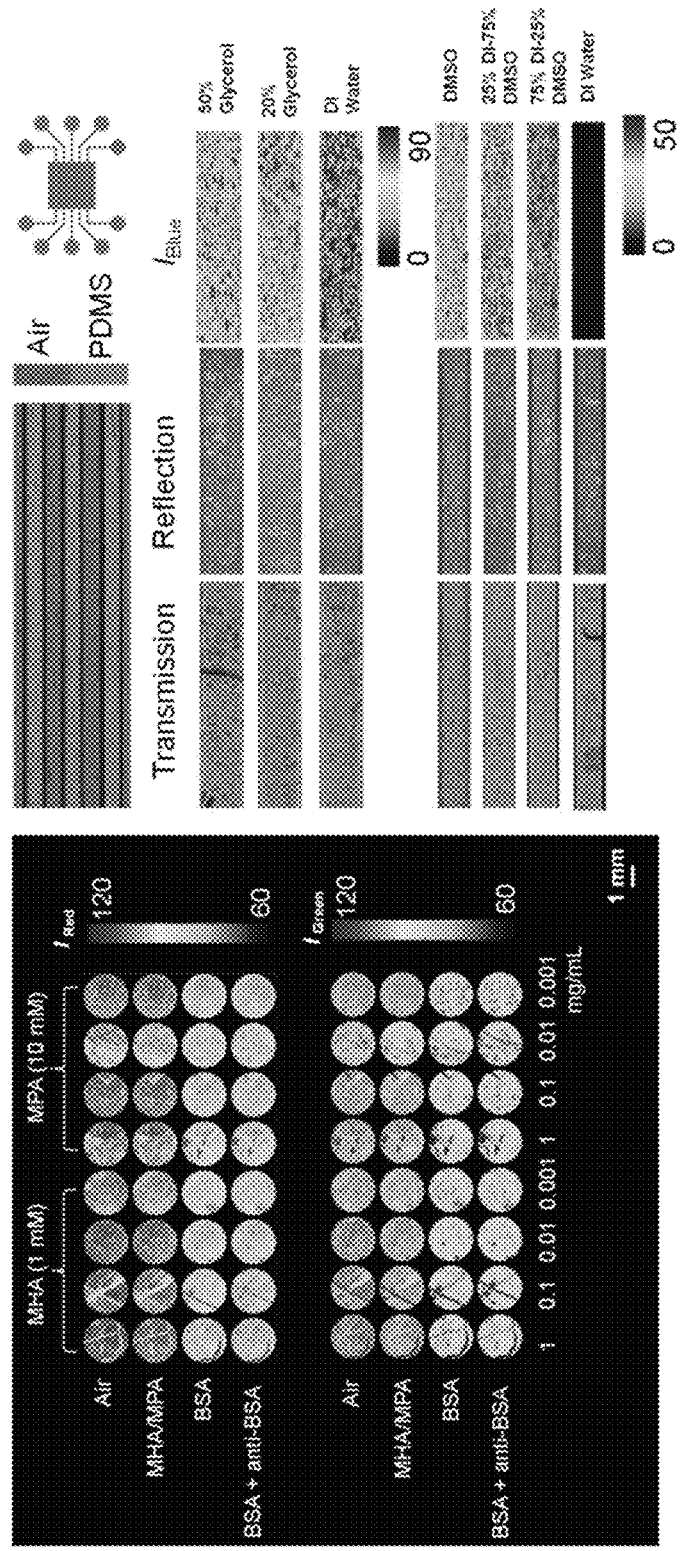
Figure 6A
Figure 6B

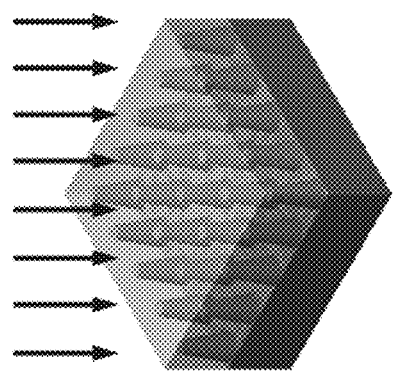
Figure 8B
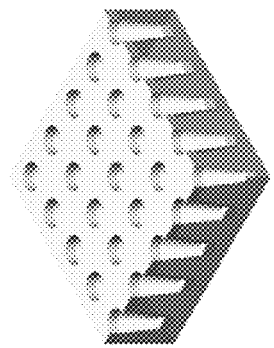
Figure 8D
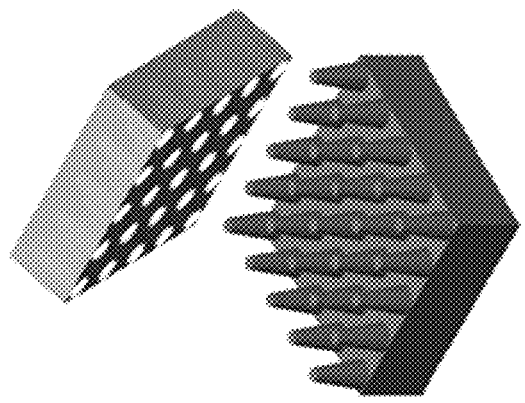
Figure 8A
Figure 8C

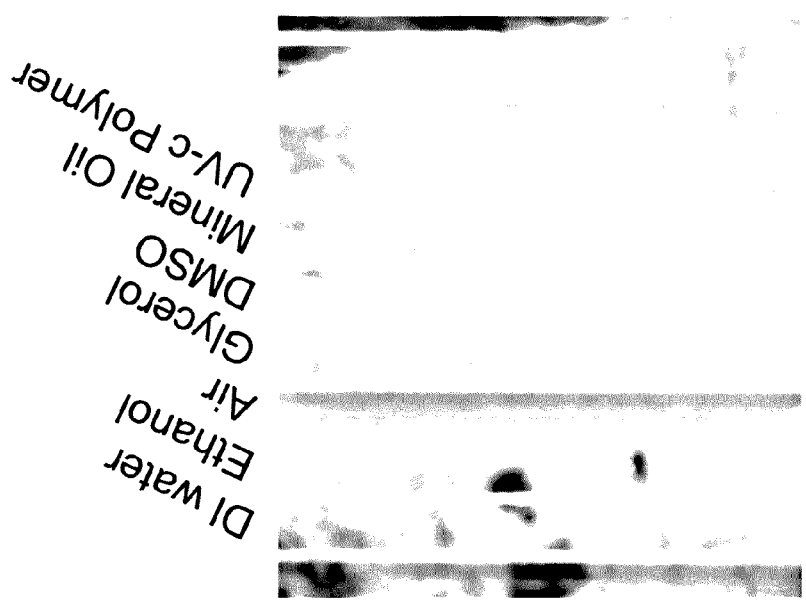
Figure 28A Transmission
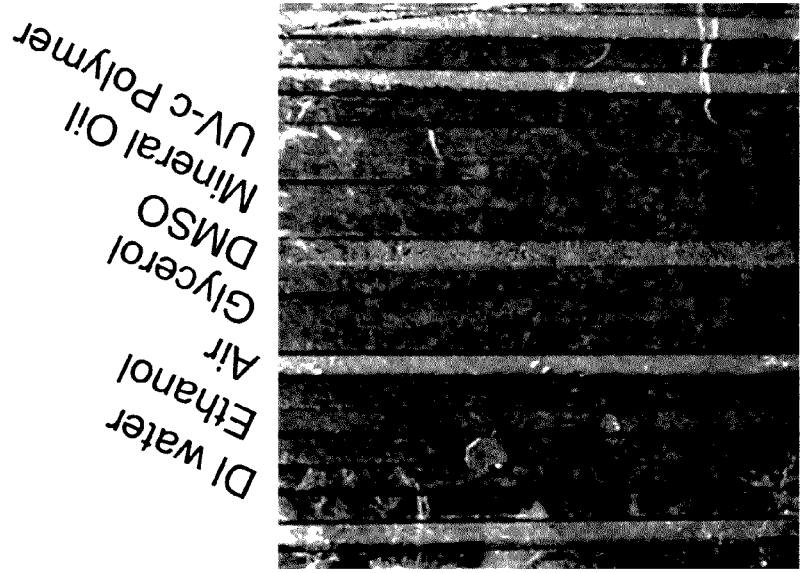
Figure 28B Reflection

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue 1 has 5' thiol modification

<400> SEQUENCE: 1
cagcaaatgg gctccgac                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Residue 1 has 5' hexachloro-fluorescein (HEX)
      modification

<400> SEQUENCE: 2
gtcgtttacc cgaggctg                                                 18
```

US 9,464,985 B2

PLASMON RESONANCE IMAGING APPARATUS HAVING NANO-LYCURGUS-CUP ARRAYS AND METHODS OF USE

CROSS-REFERENCE TO RELATED APPLICATIONS

This application claims the benefit of the filing date of U.S. Provisional Patent Application Ser. No. 61/753,229, filed Jan. 16, 2013 and U.S. Provisional Patent Application Ser. No. 61/810,411, filed Apr. 10, 2013, which are hereby incorporated by reference in their entirety.

STATEMENT OF UNITED STATES GOVERNMENT CONTRACT

The invention described herein was made by an agency of the United States Government or under a contract with an agency of the United States Government. The name of the U.S. Government agency and the Government contract numbers are: Department of Energy DE-G02-07ER 46453; DE-FG02-07ER 46471 and DE-AC52-07NA27344/B598612.

BACKGROUND

With the advancement of nanoscale fabrication, label-free sensors such as photonic crystal, whispering gallery mode ("WGM") and surface plasmon resonance ("SPR") based devices are increasingly being used for detecting DNA bases, recognizing antigen-antibody, probing protein interaction, immunoassays and identifying pathogens. Most of the above sensors work on the principle of shift in the resonance wavelength after conjugation of biomolecules to the surface of the sensor. However, the resonance peak wavelength shift ("PWS") for most of the sensors known in the art is on the order of only a few nanometers. SPR sensors do have a higher sensitivity of $2\times10^6$ nm per refractive-index unit ("RIU") for bulk refractive index, yet the absolute change in wavelength is extremely minimal for known SPR sensors in a Kretschmann configuration. As a result, the identification of the unknown target analyte (or concentration of a known target analyte) requires specialized instrument such as high precision spectrometer, multiplexer for sweeping the laser wavelengths, WGM trap, complex optical system to generate SPR (for example, prism, accurate angle tuning for the optical beam) etc.

Localized surface plasmon resonance ("LSPR") sensors, based on colloidal plasmonic particles (e.g., silver or gold), overcome some of the above limitations. However, the sensitivity of LSPR based sensors are at least an order of magnitude less compared to the gold standard prism coupled SPR sensors (Kretschmann configuration). In the LSPR configuration, the scattering spectra of the plasmonic particles shift to a different wavelength (usually to a longer wavelength) after conjugation to specific analytes, but the colloid particle sizes and positions are random and difficult to control over a large area. Thus, in the same sample area, different particles give rise to different scattering spectra such that the shifts in the wavelength are different for the same analyte. In addition, a high precision spectrometer is required to record the spectra and then complex image analysis is required to extract usable data.

Another known method to obtain high sensitivity plasmonic resonance is to make sub-wavelength holes in optically thick metal surfaces, commonly referred to as extraordinary optical transmission ("EOT") substrates. The fabrication of such substrates relies on expensive, time consuming and low throughput electron beam lithography and focused ion beam milling. Also, due to presence of single layer of metal surface, usually the nonradiative Drude (ohmic) damping losses are high, leading to damping of resonance with analytes on the top of the metal surface. In addition, EOT substrates generally show multiple transmission peaks in the visible range, making it difficult for true colorimetric sensing modalities. Quasi 3-D plasmonic crystals offer a way to increase the sensitivity by employing multiple layers of metal surfaces on nanohole surfaces. However, the resonance of such devices has been mostly demonstrated in near infrared and far infrared wavelength. Also, after adsorption of analyte, minimal to no resonance shift is observed. Most of the analyte detection or quantification is accomplished through the change in the infrared transmission intensities.

SUMMARY

Lycurgus cup was created by ancient Romans 2000 years ago and may appear to have different colors depending on the direction of light illumination in which it is viewed due to metal nanoparticle optical scattering throughout the glass of the cup. Methods and apparatus of the present invention involve a sensor having a large-area high-density array of nanoscale Lycurgus cups or nanoholes that may have 100 times better sensitivity than other reported nanoplasmonic device. Example embodiments provide nanoplasmonic spectroscopy sensing that, for the first time, has the form of colorimetric sensing that may be observed with the naked eye or ordinary visible color photography. Some example embodiments advantageously act as a "biochemical color camera" to observe and perform quantitative biochemical sensing with unprecedented sensitivities. The example embodiments described herein may advantageously be utilized as a sensor for highly sensitive refractive-index sensing, DNA hybridization detection, and protein-protein interaction. In addition, the example embodiments may be used for DNA microarrays, therapeutic antibody screening for drug discovery and pathogen detection, especially in resource-poor settings. The example embodiments also beneficially provide a low cost sensor with higher sensitivity than known SPR/LSPR instruments. Some example embodiments may also permit integration of the sensor with a microfluidic device for lab-on-chip applications.

In one aspect, an example apparatus involves: (a) an array layer having a top surface and a bottom surface, wherein a plurality of nanoholes are defined in the top surface of the array layer, wherein the plurality of nanoholes each have at least one sidewall surface and a bottom surface, (b) a thin metal film disposed on the top surface of the array layer and on the bottom surface of each of the plurality of nanoholes and (c) a plurality of nanoparticles disposed on the at least one sidewall surface of the plurality of nanoholes.

In another aspect, an example apparatus involves: (a) a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes, (b) a light source having a light emitting surface, (c) a computing device having a camera, (d) a housing having at least one sidewall that defines a chamber, wherein the at least one sidewall is opaque, wherein the at least one sidewall defines a slot at a location between the first and second ends of the housing, wherein the slot is configured to permit ingress and egress of the sensor within the chamber, wherein the housing has a first end and a second end, wherein the first end of the housing defines a base, wherein the light emitting surface of the light source is arranged within or beneath the base, wherein the base is configured to permit light from the light emitting surface to reach a bottom surface of the sensor, wherein the second end of the housing is configured to receive the computing device and position the camera in line with a top surface of the sensor.

In a further aspect, an example apparatus involves: (a) a plate defining a plurality of wells, and (b) a plurality of sensors each disposed within one of the plurality of wells, wherein each sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes.

In yet another aspect, an example method involves: (a) providing at least one sensor, wherein the at least one sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes, (b) receiving, by the sensor, at least one target analyte adjacent to a top surface of the sensor, (c) receiving, by the sensor, a broadband light transmission, (d) in response to receiving a broadband light transmission, the sensor transmitting or reflecting a specific wavelength of light, wherein the specific wavelength of light is a function of a refractive index of the at least one target analyte, and (e) causing, by the sensor, a shift in the specific wavelength of transmitted or reflected light.

In a further aspect, an example method involves: (a) receiving, by a computing device, a message providing instructions to capture an image of a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes, (b) capturing, by the computing device, an image of the sensor that is transmitting or reflecting light, (c) receiving, by the computing device, a message indicating the concentration of a target analyte that is disposed on a top surface of the sensor, (d) analyzing, by the computing device, the image of the sensor, (e) receiving, by the computing device, a message requesting that analytical data for the image of the sensor be displayed, and (f) displaying, by the computing device, the results of the analysis.

In still another aspect, a non-transitory computer-readable medium is provided. The nontransitory computer readable medium is configured to store program instructions that, when executed by a processor, cause the processor to carry out functions including: (a) providing at least one sensor, wherein the at least one sensor comprises (i) an array layer having a top surface and a bottom surface, wherein a plurality of nanoholes are defined in the top surface of the array layer, wherein the plurality of nanoholes each have at least one sidewall surface and a bottom surface, (iii) a thin metal film disposed on the top surface of the array layer and on the bottom surface of each of the plurality of nanoholes and (iv) a plurality of nanoparticles disposed on the at least one sidewall surface of the plurality of nanoholes, (b) receiving, by the sensor, at least one target analyte adjacent to a top surface of the sensor, (c) receiving, by the sensor, a broadband light transmission, (d) in response to receiving a broadband light transmission, the sensor transmitting or reflecting a specific wavelength of light, wherein the specific wavelength of light is a function of a refractive index of the at least one target analyte, and (e) causing, by the sensor, a shift in the specific wavelength of transmitted or reflected light.

In an additional aspect, a non-transitory computer-readable medium is provided. The nontransitory computer readable medium is configured to store program instructions that, when executed by a processor, cause the processor to carry out functions including: (a) receiving, by a computing device, a message providing instructions to capture an image of a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes, (b) capturing, by the computing device, an image of the sensor that is transmitting or reflecting light, (c) receiving, by the computing device, a message indicating the concentration of a target analyte that is disposed on a top surface of the sensor, (d) analyzing, by the computing device, the image of the sensor, (e) receiving, by the computing device, a message requesting that analytical data for the image of the sensor be displayed, and (f) displaying, by the computing device, the results of the analysis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 also shows that green light is transmitted by the sensor in transmission imaging mode (left) and red light is reflected by the sensor in reflection imaging mode (right).

FIG. 1B further shows an optical micrograph of the sensor according to one example embodiment taken using a camera under direct illumination (green, lower left) and without illumination (red, lower right) of a Xenon lamp flashlight.

FIG. 1C shows a scanning electron microscope ("SEM") image having bottom perspective view (top) of one example embodiment of the apparatus and shows SEM images having cross-sectional views of a plurality of nanoholes of the sensor according to one example embodiment.

FIG. 1D shows images of example embodiments of the sensor in the optical transmission mode (top) and reflection mode (bottom) for fourteen different chemicals with varying refractive indices.

FIG. 2C also shows a graph (top right) illustrating the zero-order transmission spectra for six example embodiments of the sensor each having different Ag thickness (t=40-100 nm) and each with height of h=500 nm for the plurality of nanoholes. FIG. 2C also shows a graph (bottom left) illustrating the zero-order transmission spectra of two example embodiments of the sensor each having a different pitch for the plurality of nanoholes, p=320 nm, p=350 nm. The transmission spectrum shifted with increase in the pitch. FIG. 2C further shows a graph (bottom right) illustrating the zero-order transmission spectra for four example embodiments of the sensor, two of the sensors have a thin metal film of Ag (40 nm) and the other two sensors having a thin metal film of Au (40 nm). In addition, two different heights of the plurality of nanoholes (h=500 nm and h=1000 nm) were used for the two sensors coated in Ag and for the two sensors coated in Au.

FIG. 6A shows bright field transmission images illustrating the variation of red channel (top) and green channel (bottom) intensity derived from the bright field transmission of a sensor according to an example embodiment coated with BSA (third and seventh row) and BSA+anti-BSA (fourth and eighth row). The images with air (first and fifth row) and MHA/MPA (second and sixth row) interfaces are also shown. The first four columns are for the cases when MHA (1 mM) is used for protein immobilization (0.001-1 mg/mL). The last four columns are the cases when MPA (10 mM) is used for protein immobilization (0.001-1 mg/mL) on the sensor surface.

FIG. 6B shows bright field transmission images of an example embodiment of a sensor with a PDMS microfluidic device (schematically shown in the upper-right) disposed on the top of the sensor. The orange color is due to the PDMS being in contact with the sensor. The green color is for the empty microfluidics channel. The images below show the bright field transmission (left), reflection (middle) and blue channel intensities (right) of mixing experiments on the sensor with DI water-Gycerol (middle) and DI water-DMSO (bottom).

FIG. 8A shows a master mold with nanocones disposed on a glass substrate, according to one example embodiment. In use, the mold may be cleaned and silanized for 30 minutes followed by an ethanol and deionized water rinse.

FIG. 8B shows 5 μL of UV-curable polymer (NOA-61) evenly dispersed on the top surface of the nanocone master mold of FIG. 8A. A PET sheet is placed on top of the polymer to act as a substrate. The master mold, polymer and PET sheet were exposed to UV-light (105 mW cm$^{-2}$) for 60 seconds.

FIG. 8C shows the PET substrate and polymer with a plurality of nanoholes after being peeled off the master mold according to one example embodiment.

FIG. 8D shows an example embodiment of the PET substrate layer and polymer array layer after metallization with Ag or Au to produce a thin metal film and nanoparticles to complete the fabrication of the sensor according to one example embodiment.

FIG. 28A is a top view of an image of a microfluidic device disposed on a sensor with a metal film and nanoparticles comprising silver according to one example embodiment. Different chemicals are disposed within the microfluidic device with a light source in transmission mode.

FIG. 28B is a top view of an image of a microfluidic device disposed on a sensor with a metal film and nanoparticles comprising silver according to one example embodiment. Different chemicals are disposed within the microfluidic device with a light source in reflection mode.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, "about" means+/−5%.

Figure 22:
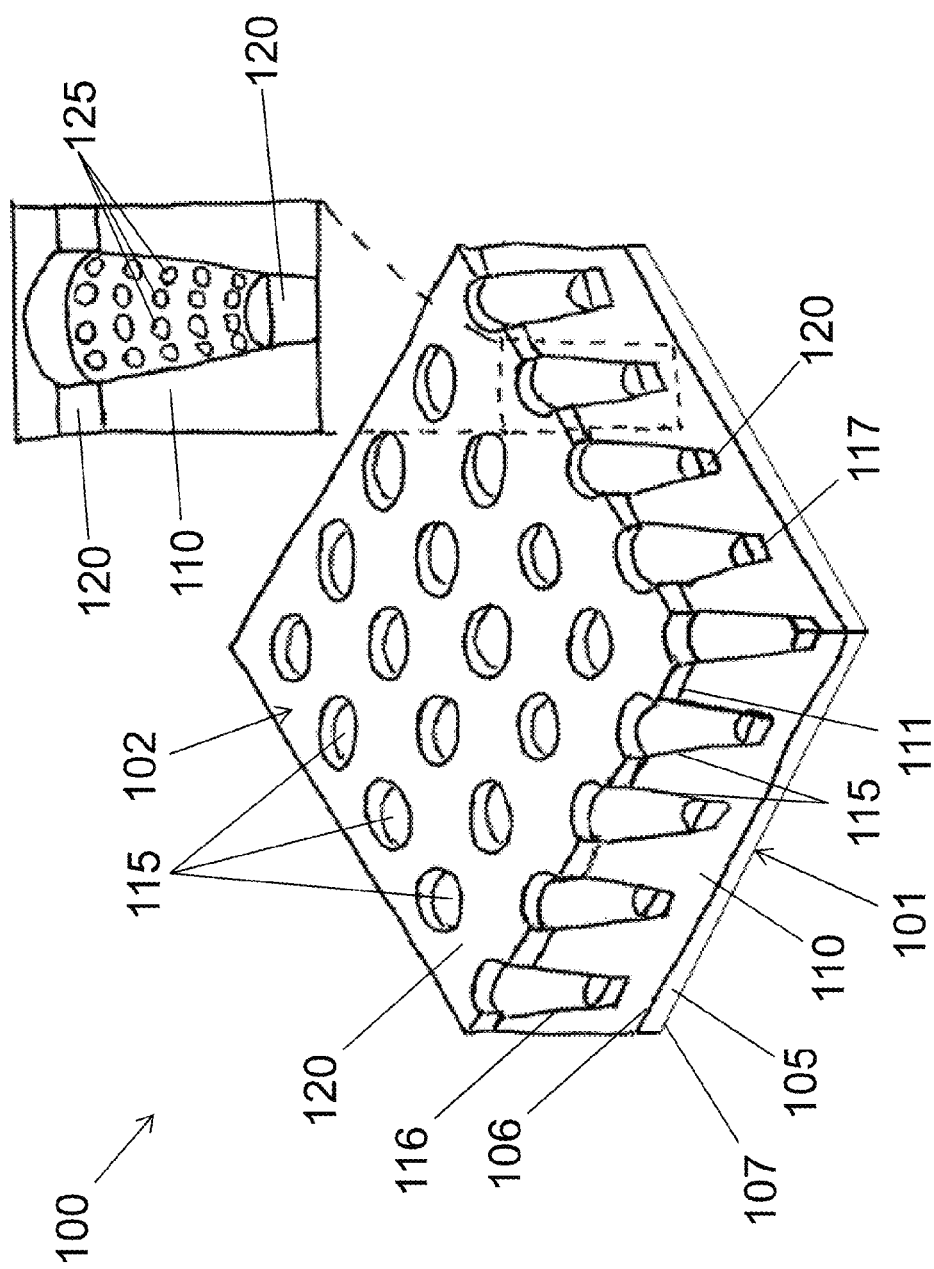
FIG. 22 is a perspective view of a sensor according to one example embodiment and includes a detail view of the nanoparticles along the sidewall of a nanohole.

The present embodiments advantageously provide a sensor that permits nanoplasmonic spectroscopy sensing in the form of colorimetric sensing that may be observed with the naked eye or ordinary visible color photography, for example. Referring now to FIG. 22, a sensor apparatus 100 is shown. The sensor 100 may include a substrate layer 105 having a top surface 106 and a bottom surface 107. The substrate layer 105 may be made of a material that is clear or transparent or translucent permitting light to pass through. In one embodiment, the substrate layer 105 may be made of plastic, for example, Polyethylene terephthalate ("PET"). In a further embodiment, the substrate layer 105 may be a PET sheet. In various other embodiments, the substrate layer 105 may be made of PDMS polymer, kapton tape, glass or silk paper, among other possibilities. In some embodiments, the substrate layer 105 may be made of an opaque material such as silicon, but in these embodiments the sensor 100 will only operate in reflection mode as discussed in more detail below.

In the embodiment shown in FIG. 22, an array layer 110 is disposed on the top surface 106 of the substrate 105. In another embodiment, the array layer 110 may be self-supporting and stand alone without a substrate layer 105. In this embodiment, the array layer may be formed through injection molding, for example. The array layer 110 may also be made of a material that is clear or transparent or translucent permitting light to pass through, as described above with respect to the substrate layer 105. In one embodiment, the array layer 110 may be made of a UV-curable polymer, such as NOA-60, 61, 63, 65, 68, 68T, 70, 71, 72, 73, 74, 75, 76, 78, 81, 83H, 84, 85, 86, 86H, 87, 88, 89, 13685, 1375, 138, 142, 143, UVS-91, NEA-121, 123, 123L, 123M, 123S, 123K, 123T, NEA-123HGA, NEA-123SHGA, NEA-123THGA, NEA-123 KHGA, NCA-130, PDMS, MasterBond UV epoxy (UV25, UV15, UV18SUV, UV15X-6Med-2, UV15-7TK1A, UV10TKLO-2), Loctite 3335 Light Cure Adhesive, UV curable Illumabond (UV Cure 60-7105, 60-7108, 60-7111, 60-7114, 60-7155, 60-7156, 60-7158, 60-7159, 60-7170), RA-1 UV Curing Epoxy Adhesive, EPO-TEK UV cure polymer, PDMS, PMMA, hydrogel or silk, among other possibilities. In some embodiments, the array layer 110 may be made of an opaque material such as silicon, but in these embodiments the sensor 100 will only operate in reflection mode as discussed in more detail below.

A plurality of nanoholes 115 may be defined in a top surface 111 of the array layer 110. The plurality of nanoholes 115 may each have at least one sidewall surface 116 and a bottom surface 117. In one embodiment, the plurality of nanoholes 115 may each have a conical or frustoconical shape, for example. In this embodiment, there is a single sidewall 116 that is continuous. In various other embodiments, the plurality of nanoholes 115 may have a polygonal shape defined by a plurality of sidewalls. In various embodiments, the sidewall surface may have a pitch ranging from about 200 nm to about 950 nm, preferably ranging from about 300 nm to about 550 nm. The provision of sidewall pitch aids in the transmission and reflection of light by providing more surface area in the direct path of transmitted light as compared to nanoholes having completely vertical walls (see FIG. 3a). In some embodiments, the plurality of nanoholes may have a height ranging from about 100 nm to about 1500 nm, preferably ranging from about 400 nm to about 600 nm.

Figure 3A:
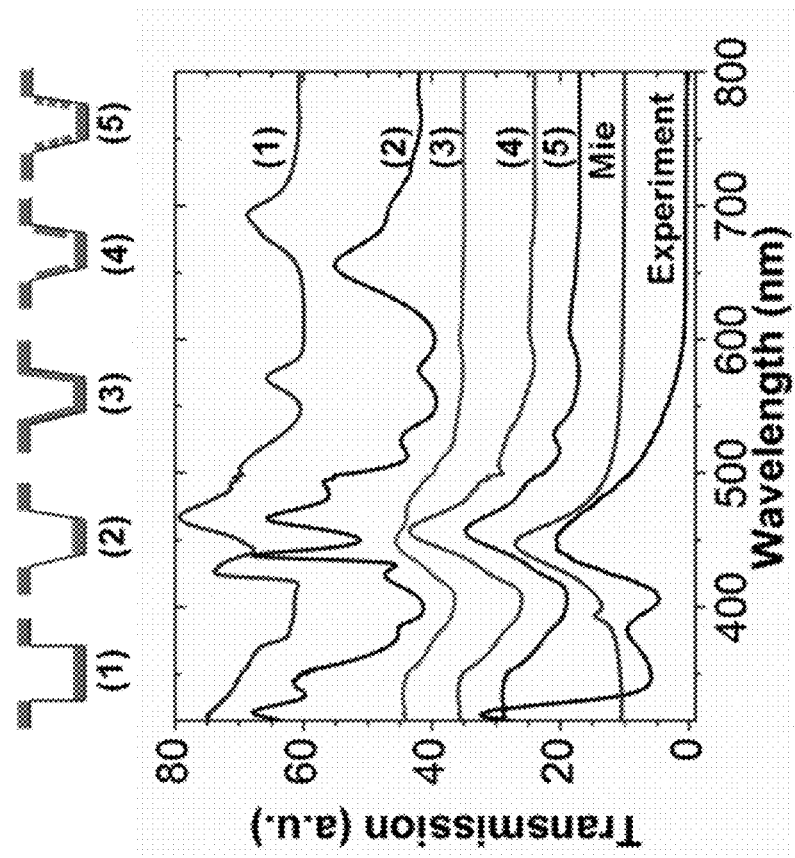
FIG. 3A shows a finite difference time domain ("FDTD") simulated transmission spectra for five example embodiments of sensors each having different shaped nanoholes labeled (1)-(5). For all the simulations, the height of the plurality of nanoholes was h=500 nm and the thickness of the thin film metal is t=90 nm. The experimental transmission spectrum and calculated extinction spectrum for a nanoparticle (having a diameter of d=50 nm) in a surrounding refractive-index of n=1.56 is also presented (Mie).

In addition, a thin metal film 120 may be disposed on the top surface 111 of the array layer 110 and on the bottom surface 117 of each of the plurality of nanoholes 115, while a plurality of nanoparticles 125 may be disposed on the sidewall surface 116 of the plurality of nanoholes 115. In one embodiment, the thin metal film may have a thickness ranging from about 20 nm to about 900 nm, preferably ranging from about 80 nm to about 100 nm. In embodiments in which the metal film has a thickness greater than 120 nm, the sensor 100 will only in reflection mode, as described below. In one embodiment, the plurality of nanoparticles 125 include a discontinuous metal film that is interrupted at intervals, rather than as a continuous film, as shown in FIG. 3A (example 4). In an alternative embodiment, as shown in FIGS. 1C, 3A (example 5) and 22, the plurality of nanoparticles 125 may be discrete particles randomly deposited on the sidewalls 115. Each of the foregoing arrangements is configured to permit light to pass from the bottom 101 of the sensor 100 through the sidewalls 115. In one embodiment, the plurality of nanoparticles 125 may be metal. In other embodiments, the thin metal film 120 and the plurality of nanoparticles 125 may include plasmonic metals such as gold, silver, aluminum, copper, platinum or alloys of the foregoing metals, among other possibilities. The resonance of the sensor will vary depending upon the type of metal employed for the thin metal film 120. The metal used for the thin metal film 120 and the nanoparticles 125 should be the same to ensure that the reflective properties are consistent.

In operation, the sensor 100 is configured to permit two modes of analysis, namely a transmission mode and a reflection mode. In transmission mode, light is transmitted from beneath the bottom surface 101 of the sensor 100 and through the portion of the sidewall surface 116 of the plurality of nanoholes 115 that is not obstructed by the thin metal film 120 or nanoparticles 125. In reflection mode, light is transmitted from above the top surface 102 of the sensor 100 and reflected off of the thin metal film 120 and the nanoparticles 125. The transmission and reflection modes cause different colors to be displayed. In addition, the gradations of the colors vary based on the type of target analyte being analyzed, as well as the concentration of the target analyte that is present. After binding of the target analyte to the thin metal film 120 and nanoparticles 125, the resonance position of the transmission and/or reflection spectrum will be different. For example, the transmission/reflection intensity of the sensor 100 typically increases after target analyte binding.

Figure 23:
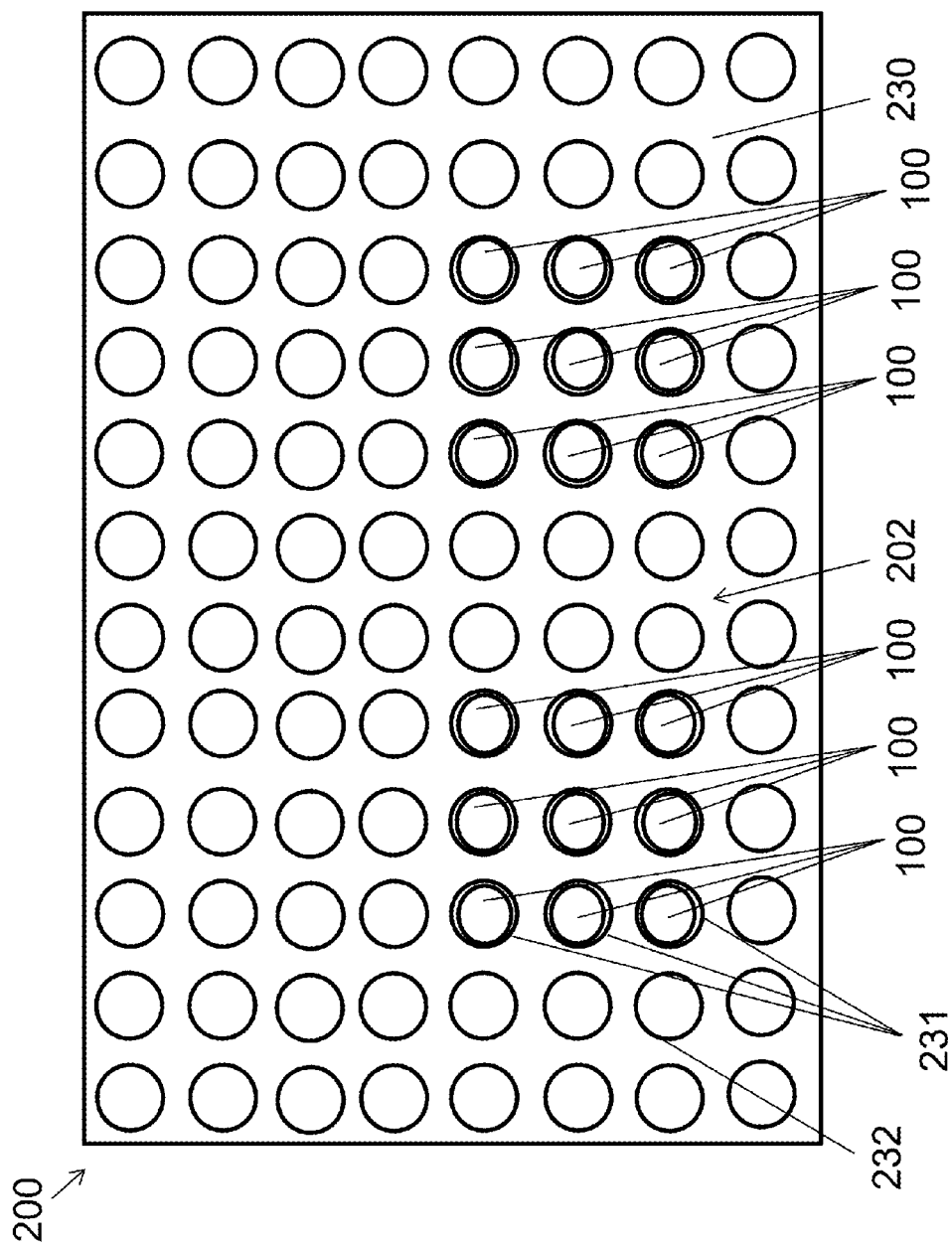
FIG. 23 is a top view of a well plate defining a plurality of wells with a plurality of sensors each disposed within one of the plurality of wells according to one example embodiment.
Figure 24:
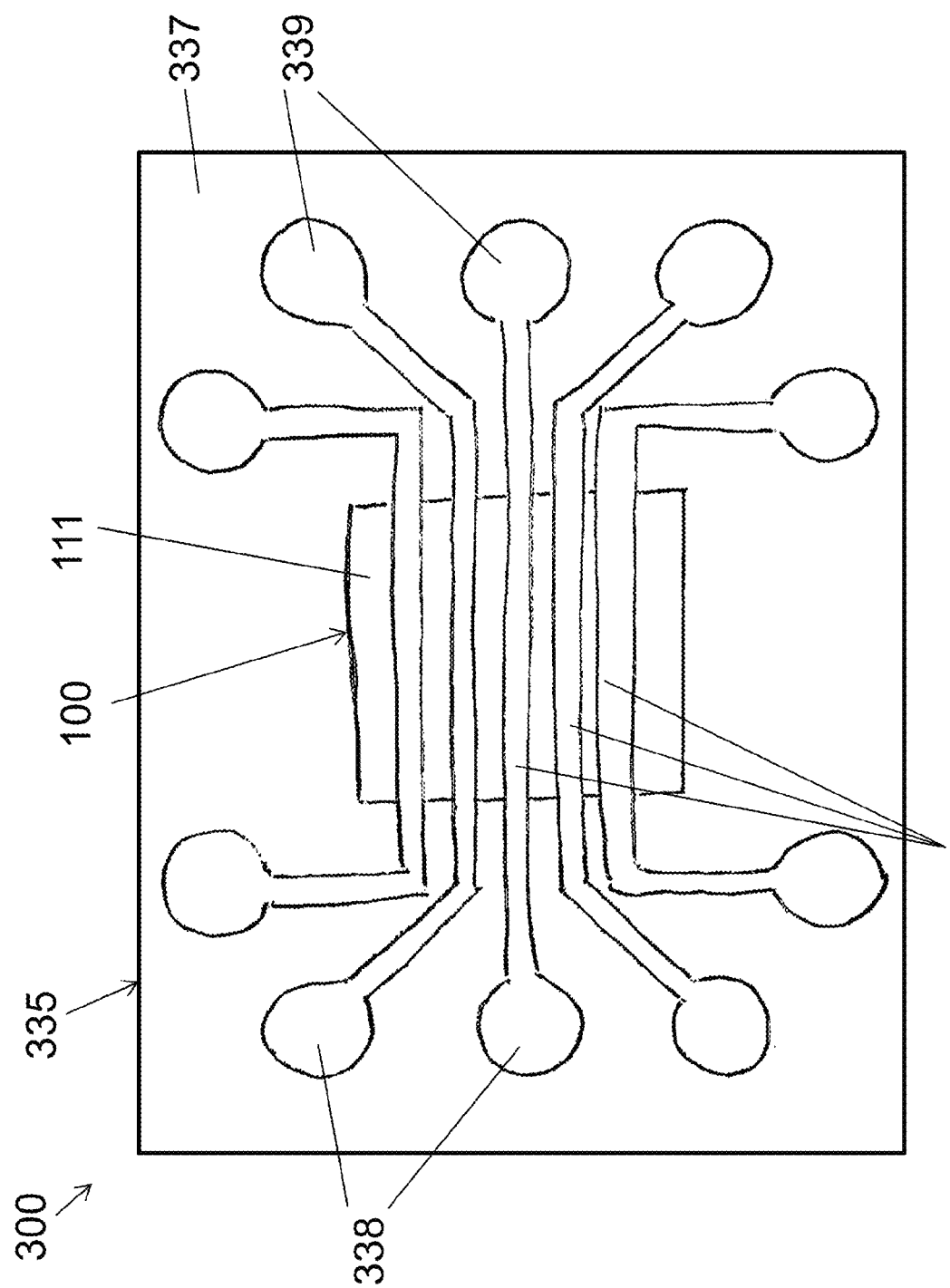
FIG. 24 is a top view of a microfluidic device disposed on a sensor according to one example embodiment.

Referring now to FIG. 23, an apparatus 200 is shown. Apparatus 200 includes a plate 230 defining a plurality of wells 231. In this embodiment, a plurality of sensors 100 each taking the form of the sensor apparatus 100 may each be disposed within one of the wells 231. This arrangement permits different target analytes to be placed in each well 231 for analysis at the same time. In one embodiment, the plate 230 may be clear or transparent permitting the transmission of light therethrough. In other embodiments, the walls 232 of the wells 231 may be opaque to minimize cross-talk or interference from light transmission in adjacent wells. The opaque walls would be more beneficial during reflection mode than for transmission mode.

Referring now to FIGS. 24 and 27-29, an apparatus 300 is shown. Apparatus 300 may include a sensor 100 taking the form of the sensor apparatus 100 and may include a microfluidic device 335 disposed on the top surface 111 of the array layer 110 of the sensor 100. In one embodiment, the microfluidic device 335 may include a plurality of channels 336 defined in a base 337. The plurality of channels 336 each have an inlet 338 at a first end and an outlet 339 at a second end. In one embodiment, the base 337 may be clear or transparent or translucent permitting the transmission of light therethrough. The interface of the microfluidic device 335 and the sensor 100 permits fluid communication between the plurality of channels 336 and the top surface 102 of the sensor 100 to permit binding of the target analyte to the thin metal film 120 and nanoparticles 125 in operation.

Figure 25:
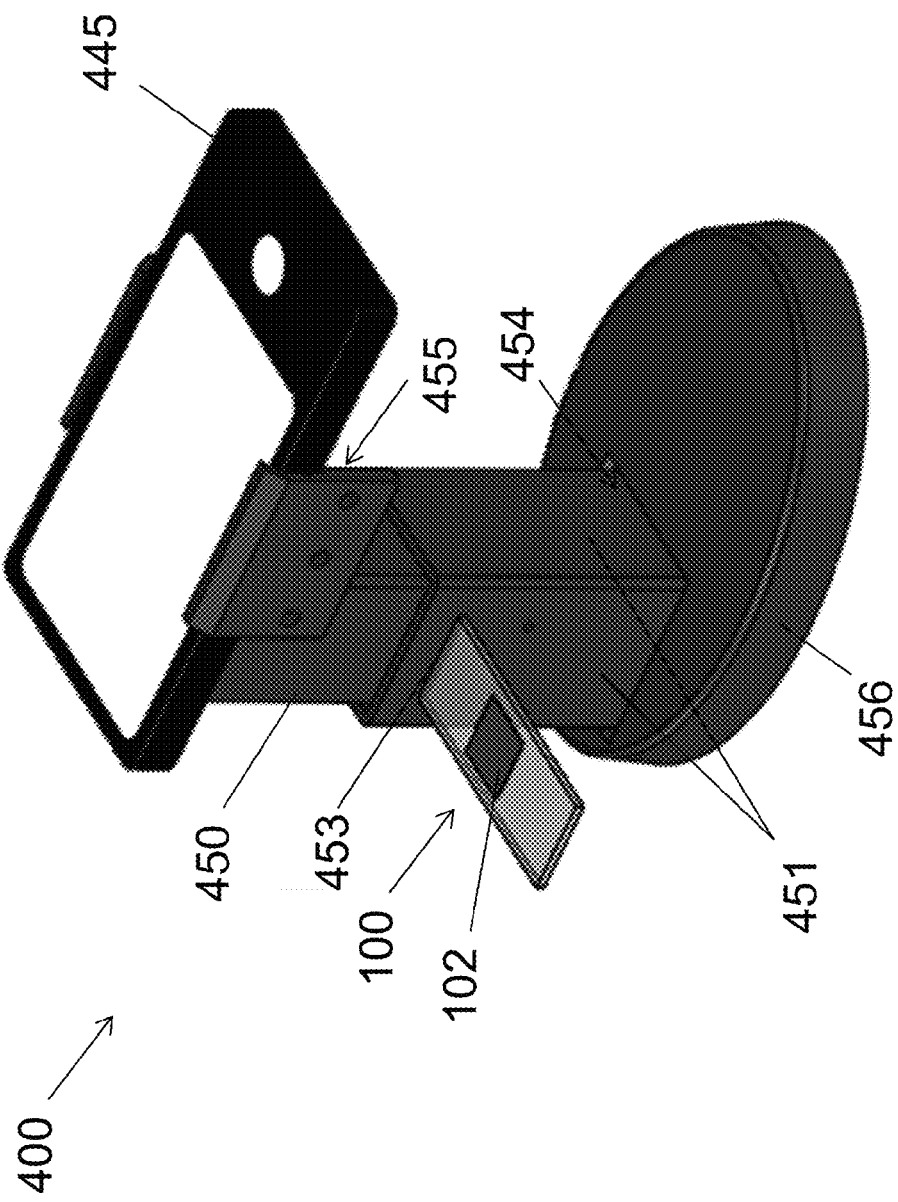
FIG. 25 is perspective view of an apparatus according to one example embodiment.
Figure 26:
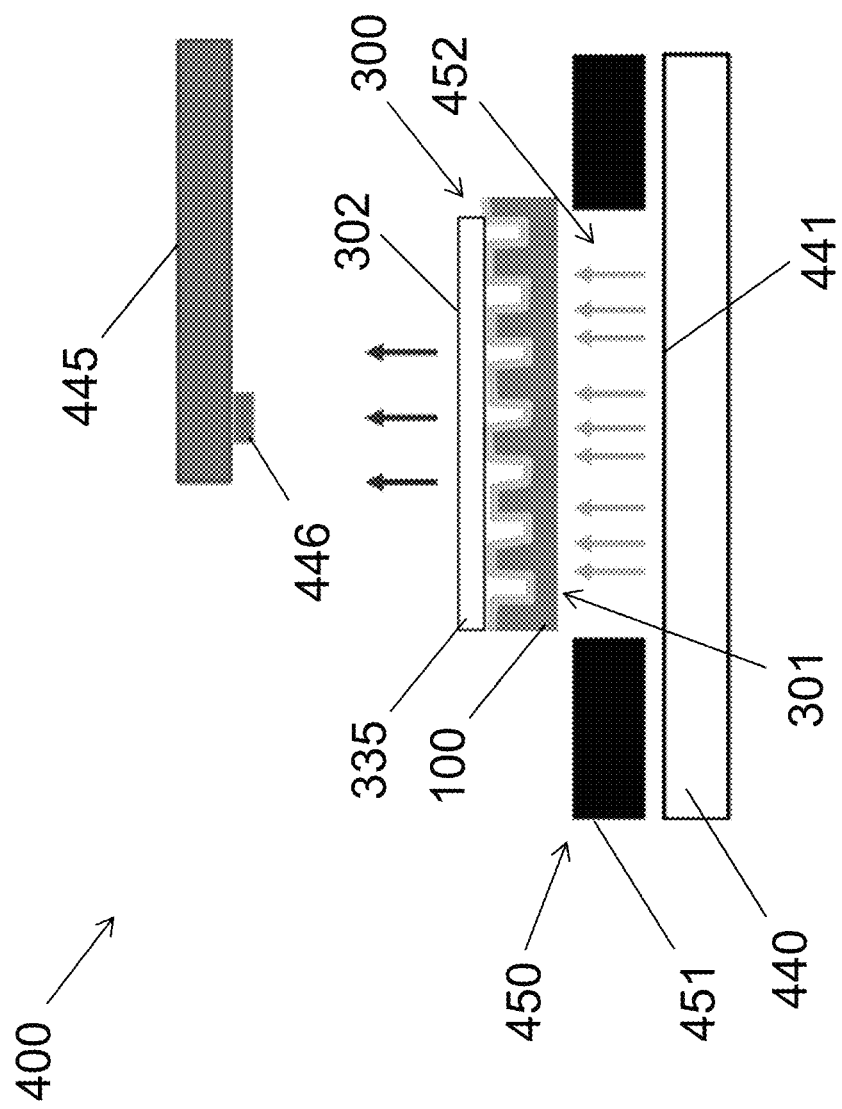
FIG. 26 is perspective view of an apparatus according to one example embodiment.
Figure 27:
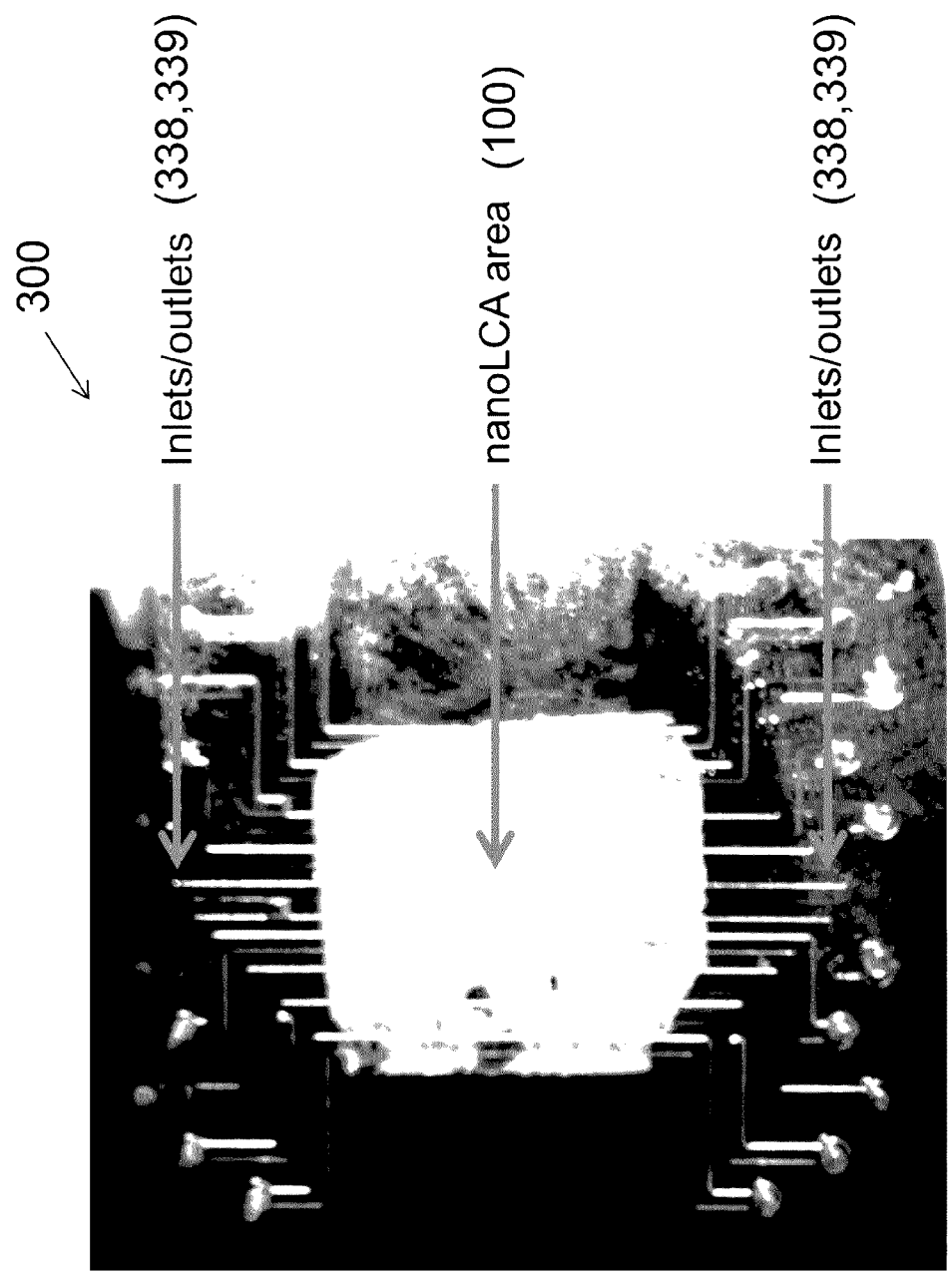
FIG. 27 is a top view of an image of a microfluidic device disposed on a sensor with a metal film and nanoparticles comprising silver according to one example embodiment. The image was taken by a camera of a mobile phone.
Figure 29:
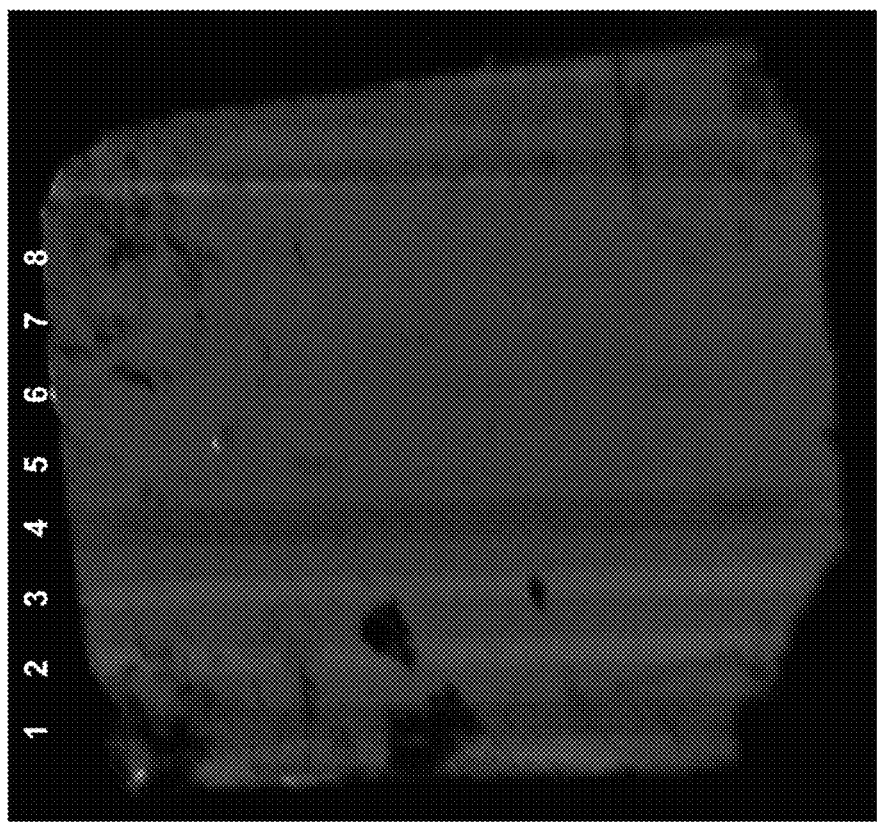
FIG. 29 is a top view of an image of a microfluidic device disposed on a sensor with a metal film and nanoparticles comprising gold according to one example embodiment. Different chemicals are disposed within the microfluidic device with a light source in transmission mode.

Referring now to FIGS. 25 and 26, an apparatus 400 is shown. Apparatus 400 may include a sensor apparatus 100 (FIG. 25), 200 (not shown) or 300 (FIG. 26). Apparatus 400 may further include a light source 440. In one embodiment, the light source 440 may be an LED screen or one or more point LEDs. In one embodiment, the light source 440 may be arranged beneath the bottom surface 101 of the sensor 100 to transmit light through the sensor 100 in a transmission mode, shown in FIG. 1A (left) and in FIG. 29A. In another embodiment, the light source 440 may be arranged above the top surface 102 of the sensor 100 in a reflection mode, shown in FIG. 1A (right) and in FIG. 28B. Further, FIG. 2D shows the results for two different polarizations of incident light. Note that s-polarization is directed out-of-plane incident light (i.e., into the paper), whereas p-polarization is in-plane incident light. Incident light may be transmitted at an angle 0, where the angle 0 is measured with respect to normal, such that 0 degrees is normal incidence. With respect to s-polarization light, as the angle of incident light increases, the intensity of the light transmission decreases, and the position of resonance remains fairly unaltered. For p-polarization light, as the angle of incident light increases, the intensity of the transmitted light decreases as well, but the position of resonance of the sensor shifts to a higher wavelength. The contour plots of FIG. 2D represent the corresponding dispersion of the sensor 100 (i.e., the relationship between energy and momentum on the sensor 100). As such, the incident light is preferably as collimated as possible and Normal Incident Light (0±10 degrees) is preferred. A light source may likewise be arranged and utilized in a similar manner with respect to apparatus 100, 200 and 300.

Apparatus 400 may also include a computing device 445. In one embodiment, the computing device 445 may include personal computers, laptop computers, tablet computers, cellular phones, and countless types of Internet-capable devices. In one embodiment, the computing device 445 may include a camera 446 configured to take photographs and/or video of the sensor 100. In a further embodiment, the computing device 445 may include a second light source enabling the apparatus to operate in reflection mode through light directed at the top surface 102, 202, 302 of the sensor 100, 200, 300. In one embodiment, the camera may have a flash that serves as the second light source in reflection mode.

In addition, apparatus 400 may include a housing 450 with a first end 454 and a second end 455 and having at least one sidewall 451 extending between the first end 454 and the second end 455 of the housing 450. A single sidewall 451 may have a continuous form with a circular or oval cross-section. Alternatively, a plurality of sidewalls 451 may be joined together having a polygonal cross-section. The sidewall(s) 451 defines a chamber 452. In one embodiment, the sidewall(s) 451 may be opaque to direct light from the light source 440 to the sensor 100. In one embodiment, the sidewall 451 may define a slot 453 at a location between the first and second ends 454, 455 of the housing 450. The slot 453 may be configured to permit ingress and egress of the sensor 100, 200, 300 within the chamber 452. In one embodiment, the first end 454 of the housing 450 may be coupled to a base 456. The light emitting surface 441 of the light source 440 may be arranged within or beneath the base 456. In one embodiment, the base 456 may be configured to permit light from the light emitting surface 441 to reach a bottom surface 101, 301 of the sensor 100, 300, in transmission mode. In one embodiment, the second end 455 of the housing 450 may be configured to receive the computing device 445 and position the camera 446 in line with a top surface 102, 302 of the sensor 100, 300. In one embodiment, the camera may be positioned according to the focal length of the camera, which may vary according to camera model, but which may range from about 3 cm to about 6 cm, for example, above a top surface 102, 302 of the sensor 100, 300 to measure the index of refraction in a detection zone at a distance of about 5 nm to about 50 nm above the top surface 102, 302 of the sensor 100, 300.

Figure 30:
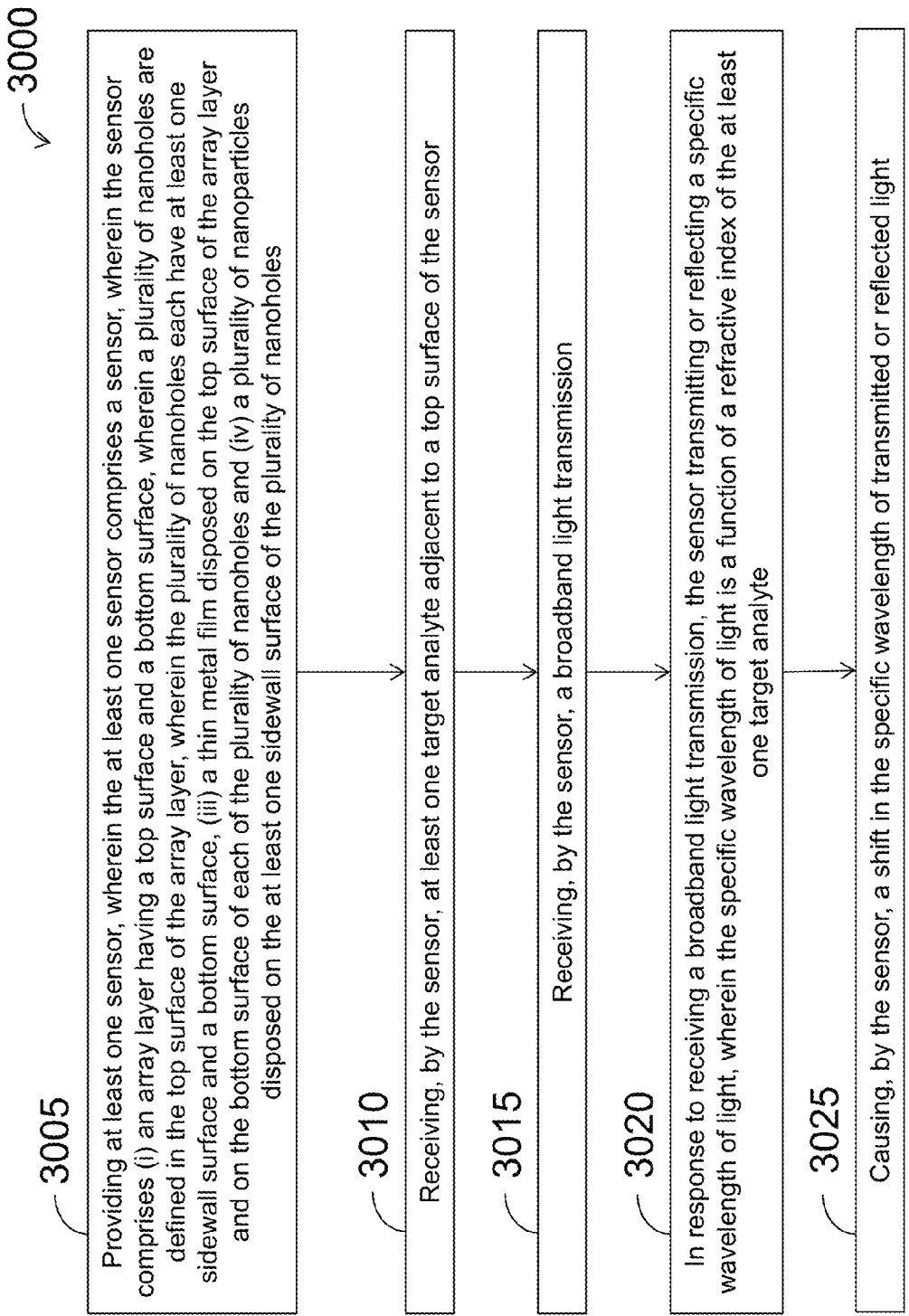
FIG. 30 is a flowchart of a method, according to an example embodiment.

FIG. 30 is a flow chart of a method, according to an example embodiment. Example methods, such as method 3000 of FIG. 30, may be carried out by an operator or a control system and/or by other components in communication with or disposed on the sensor apparatus. A control system may take the form of program instructions stored on a non-transitory computer readable medium and a processor that executes the instructions. However, a control system may take other forms including software, hardware, and/or firmware.

Example methods may be implemented as part of observing and performing quantitative biochemical sensing. As shown by block 3005, method 3000 involves providing at least one sensor taking the form of any of the sensor apparatus 100, 200, 300 or 400 described above. At block 3010, the sensor receives at least one target analyte adjacent to a top surface of the sensor. Then at block 3015, the sensor receives a broadband light transmission. In one embodiment, the light transmission may be directed at a bottom surface of the sensor in a transmission mode. In an alternative embodiment, the light transmission may be directed at a top surface of the sensor in a reflection mode. In response to receiving a broadband light transmission, the sensor transmits or reflects a specific wavelength of light, wherein the specific wavelength of light is a function of a refractive index of the target analyte, as shown at block 3020. Then, at block 3025, the sensor causes a shift in the specific wavelength of transmitted or reflected light.

In further embodiments, the target analytes bind to the thin metal film of the sensor. The binding may be due to natural adsorption of molecules on the surface (e.g., due to Van der Waals reaction) or may be due to the reaction of specific recognition molecules placed on the top surface of the sensor. The recognition molecules, which will preferentially react with the target molecules, are generally covalently bound to the top surface of the sensor. A recognition molecule, a target molecule or an analyte may be, for example, a nucleic acid (DNA, RNA or analogs thereof), polypeptide, protein solutions, peptide solutions, single or double stranded DNA solutions, RNA solutions, RNA-DNA hybrid solutions, solutions containing compounds from a combinatorial chemical library, antigen, polyclonal antibody, monoclonal antibody, single chain antibody (scFv), F(ab) fragment, F(ab')2 fragment, Fv fragment, small organic molecule, cell (e.g., a eukaryotic cell, prokaryotic cell, mammalian cell, or any other type of cell), virus, bacteria, polymer or biological sample. A biological sample may be for example, blood, plasma, serum, gastrointestinal secretions, tissues, tumors, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatic fluid.

A proper surface chemistry protocol to immobilize the recognition molecules on the top surface of the sensor permits the sensor to function. In one embodiment, one surface chemistry protocol that may be used is thiol chemistry to bond thiol modified DNA and molecules to immobilize on the top surface of the sensor (detailed in the Example section below). In another embodiment, another surface chemistry protocol that may be used is multilayer assembly based on electrostatic interaction of carboxylate (11-mercaptoundecanoic acid (MUA)) and amino group (poly(ethylenimine)) (MUA-PEI chemistry). In various other embodiments, methods to functionalize the top surface of the sensor include (i) poly (ethylene glycol)-carboxylate (PEG-carboxylate) activated with EDC-NHS and (ii) dextran chemistry. Improved molecular conjugation chemistry may be used to test, for example, cell lysate to demonstrate pathogen detection. Here, surface functionalized enzymes may be utilized to improve the affinity of particular pathogen to be captured on a plasmonic substrate. For example, vancomycin coating may preferentially capture E-coli bacteria on the surface even when using a real human blood sample.

In some embodiments, the shift in the specific wavelength of light is measured. This measurement may be observed by the naked eye of the operator, a microplate reader or by a computing device. Other measuring devices may include a spectrometer, a microarray scanner, a bright field microscope, a fluorescence microscope, a confocal microscope, a confocal fluorescence microscope, a phase contrast microscope, an SPR system, a Near Field Scanning Optical Microscope or a Fiber coupled spectrometer.

Figure 31:
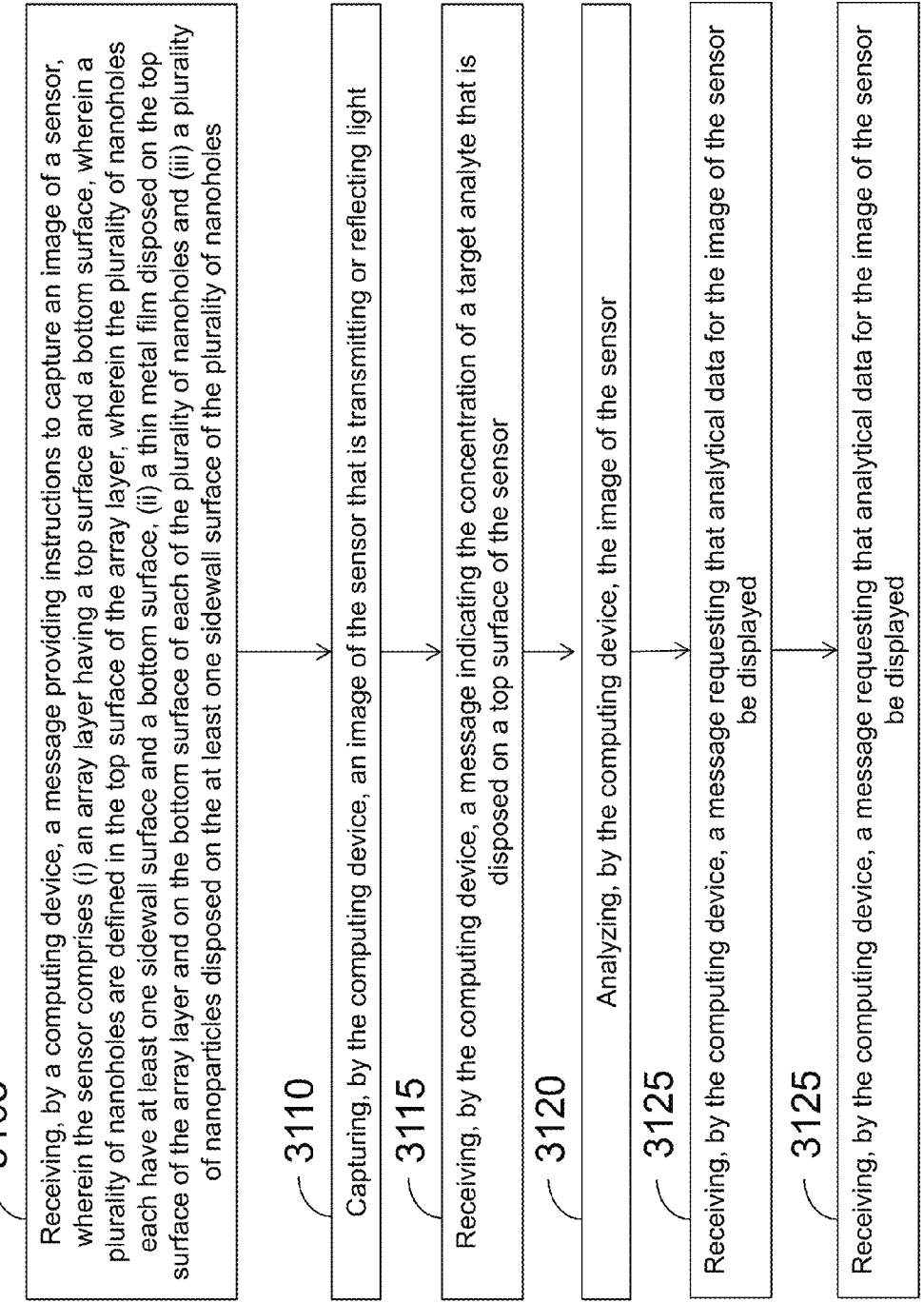
FIG. 31 is a flowchart of a method, according to another example embodiment.

Referring now to FIG. 31, as shown by block 3105, method 3100 includes a computing device receiving a message providing instructions to capture an image of a sensor taking the form of any of the sensor apparatus 100, 200, 300 or 400 described above. Then, at block 3110, the computing device captures an image of the sensor, while the sensor is transmitting or reflecting light. The computing device then receives a message indicating the concentration of a target analyte that is disposed on a top surface of the sensor, at block 3115. In response, the computing device analyzes the image of the sensor, as shown at block 3120. The computing device then receives, at block 3125, a message requesting that analytical data for the image of the sensor be displayed. At block 3130, the computing device displays the results of the analysis.

Figure 32C:
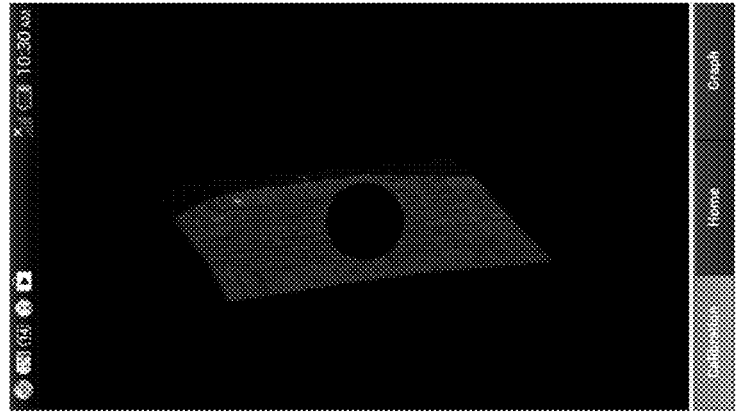
FIG. 32C is another screenshot of a graphical user interface configured to assist in carrying out the method of claim 31, according to an example embodiment.
Figure 32B:
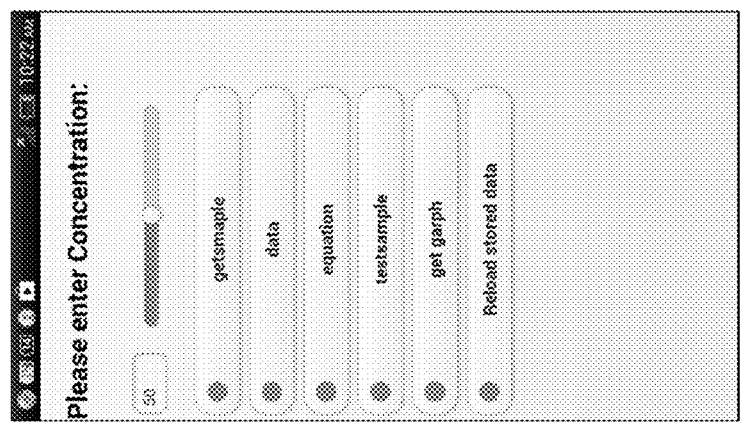
FIG. 32B is another screenshot of a graphical user interface configured to assist in carrying out the method of claim 31, according to an example embodiment.
Figure 32A:
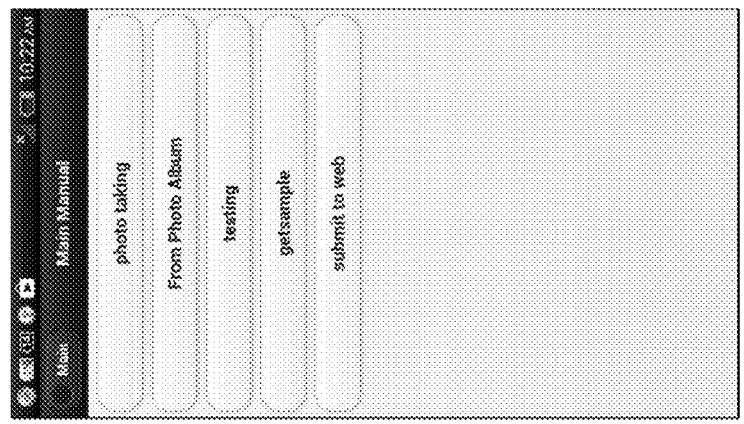
FIG. 32A is a screenshot of a graphical user interface configured to assist in carrying out the method of claim 31, according to an example embodiment.
Figure 32E:
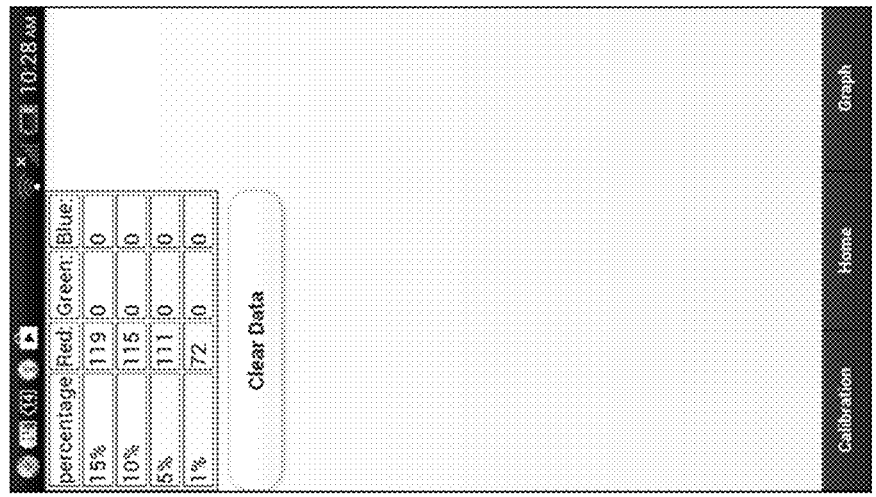
FIG. 32E is another screenshot of a graphical user interface configured to assist in carrying out the method of claim 31, according to an example embodiment.

A graphical user interface for a computing device, according to one example embodiment, is shown in FIG. 32A-E for carrying out the steps of method 3100. In this embodiment, the computing device is a mobile phone. In one embodiment, shown in FIG. 32A, a user may input a request via the computing device to capture or retrieve an image of sensor. The user may also request "testing," which may take the user to the Calibration page, which is for a user that wants to perform their own calibration. As shown in FIG. 32B, a GUI is provided to permit the user to enter the concentration of calibration sample, illustrated as a sodium chloride solution (NaCl) of 50 g/L. The concentration units may also be input by the user. For example, the concentration may be displayed as mg/mL, mg/L, mM (millimolar), mmol/L, mg/dL etc. Alternatively, in an embodiment in which the user does not want to perform the calibration, the user may instead request "getsample" to use a built-in calibration function that is part of the graphical user interface program.

Regardless of the calibration method used, a user may also request "getsample" to invoke the camera function, shown in FIG. 32C. The user may capture an image using the camera function and then select a region of the image for analysis. The black circle, shown in FIG. 32C represents the area selected by the user. After selection of the region for analysis, the computing device may responsively analyze the region. For example, the computing device may extract the value of red, green and blue channels from a 24 bit RGB image captured by the camera.

Figure 32D:
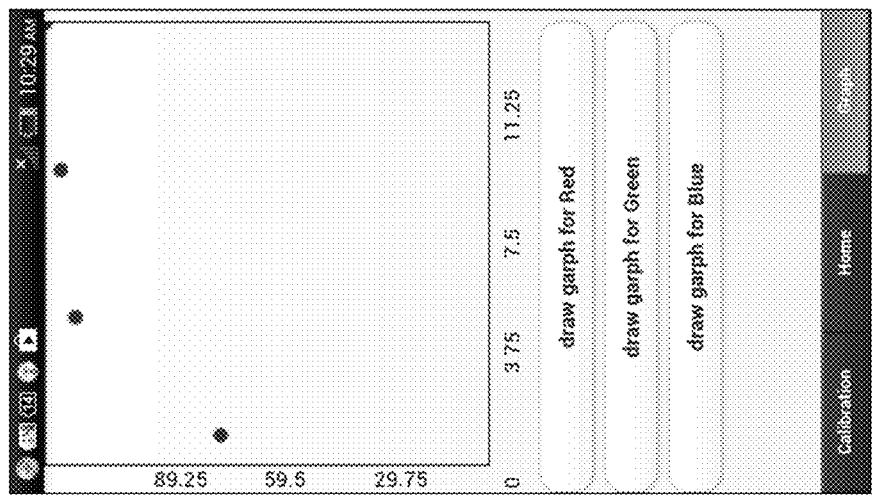
FIG. 32D is another screenshot of a graphical user interface configured to assist in carrying out the method of claim 31, according to an example embodiment.

In still another embodiment, shown in FIG. 32D, the user may then request "data," "equation" and "get graph" to view the data, the equation and the graph, respectively, as shown in FIG. 32D. For example, a graph is displayed by the computing device based on analytical data derived from a sensor image. In one embodiment, additional options are displayed for a user to view a graph showing red channel spectrum, green channel spectrum or the blue channel spectrum derived from the sensor image. In an additional embodiment, shown in FIG. 32E, a table is displayed by the computing device showing analytical data derived from a sensor image.

In some embodiments, the user may also request, via the computing device, that sensor images or analytical data be emailed or uploaded to a website, the cloud or other internet-based database.

In another embodiment, shown in FIG. 32B, a user may request "reload stored data" in order to reload data already obtained the user or another user, where the data may be stored on the computing device, on the Internet and/or in a cloud database. In still another embodiment, the user may request "testsample" in order to compare the results of an unknown sample with the calibration results and then obtain an output of the concentration of the unknown sample.

EXAMPLES

The nano Lycurgus Cup Array ("NanoLCA") sensor of the present invention exhibits metal nanoparticle-like single transmission wavelength peak in the whole visible ranges. Electromagnetic simulation revealed the plasmon resonance scattering modes of the metal nanoparticles on the nanohole side walls and the corresponding single-peak wavelength scattering light selectively transmitted by the nanoLCA. The huge transmission and reflection wavelength shifts upon binding of molecules on the flexible, high-throughput, large-area nanoLCA sensor. The wavelength shifts are up to 200 nm (with maximum sensitivity of 46000 nm per refractive-index unit ("RIU") and figure of merit ("FOM") of 1022), much greater than the typical nanoparticle plasmon resonance wavelength shift and large enough to detect the color differences directly by naked eyes and conventional bright field microscopes. This eliminates the need for precision spectrometer or fluorescence labeling. The ultrasensitive label free colorimetric plasmon resonance imaging of different refractive indices solutions, single- and double-stranded oligonucleotides and antigen-antibody protein interactions were demonstrated on the nanoLCA sensor.

A nanoimprint method was employed to produce nanoLCA substrate on plastic substrate to reduce cost and simplify the fabrication process. Metal (Ag or Au) was deposited on the nanoLCA by electron beam evaporation, producing metal surface on the rim of the holes, on the bottom of the holes and also nanoparticles-like structure on the sidewalls of the holes. Due to selective transmission of the scattering spectra from the nanoparticles, the sensor is characterized by single transmission spectral peak in the entire visible wavelength, giving rise to the Lycurgus cup effects. Due to unprecedented high sensitivity (about 46000 nm per RIU), the nanoLCA sensor is very sensitive in detecting small changes in refractive index of the analyte and gives rise to a huge shift in the resonance wavelength which is even detectable by naked eyes and normal bright field ("BF") microscopy making it a true colorimetric sensor.

Figure 1A:
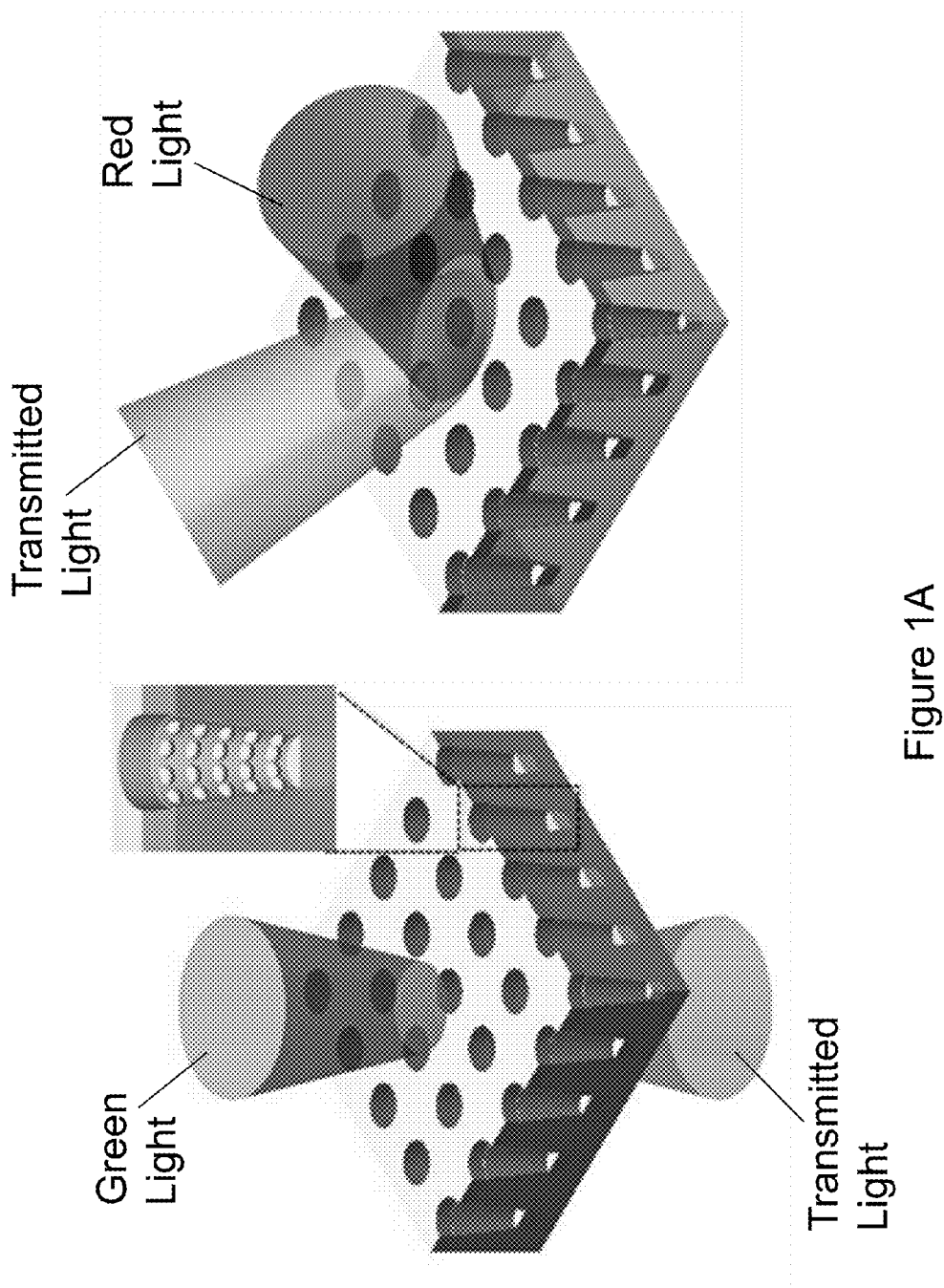
FIG. 1A shows a perspective view of the sensor according to one example embodiment and includes a detail view of the nanoparticles along the sidewall of a nanohole.
Figure 1B:
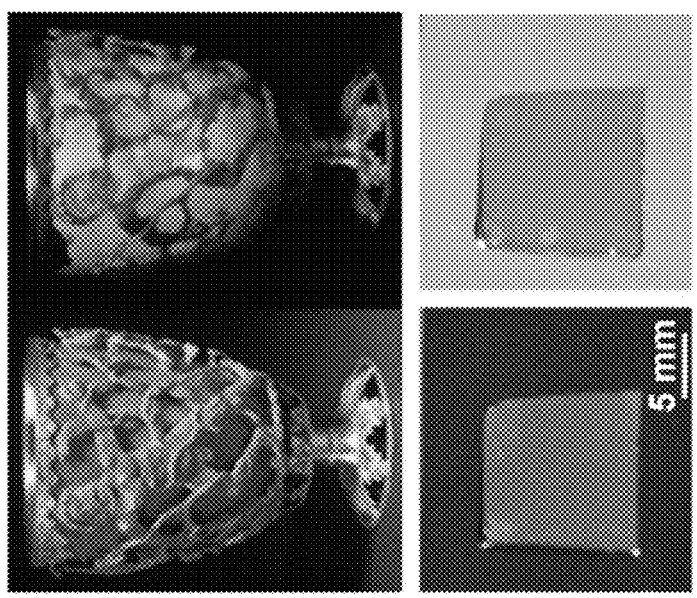
FIG. 1B shows the Lycurgus cup in British Museum dated back to fourth century AD. Due to scattering of nanoparticles on sidewall (5-60 nm in diameter), the cup appears green in reflected light (top left) and appears red in transmission light (top right).
Figure 7:
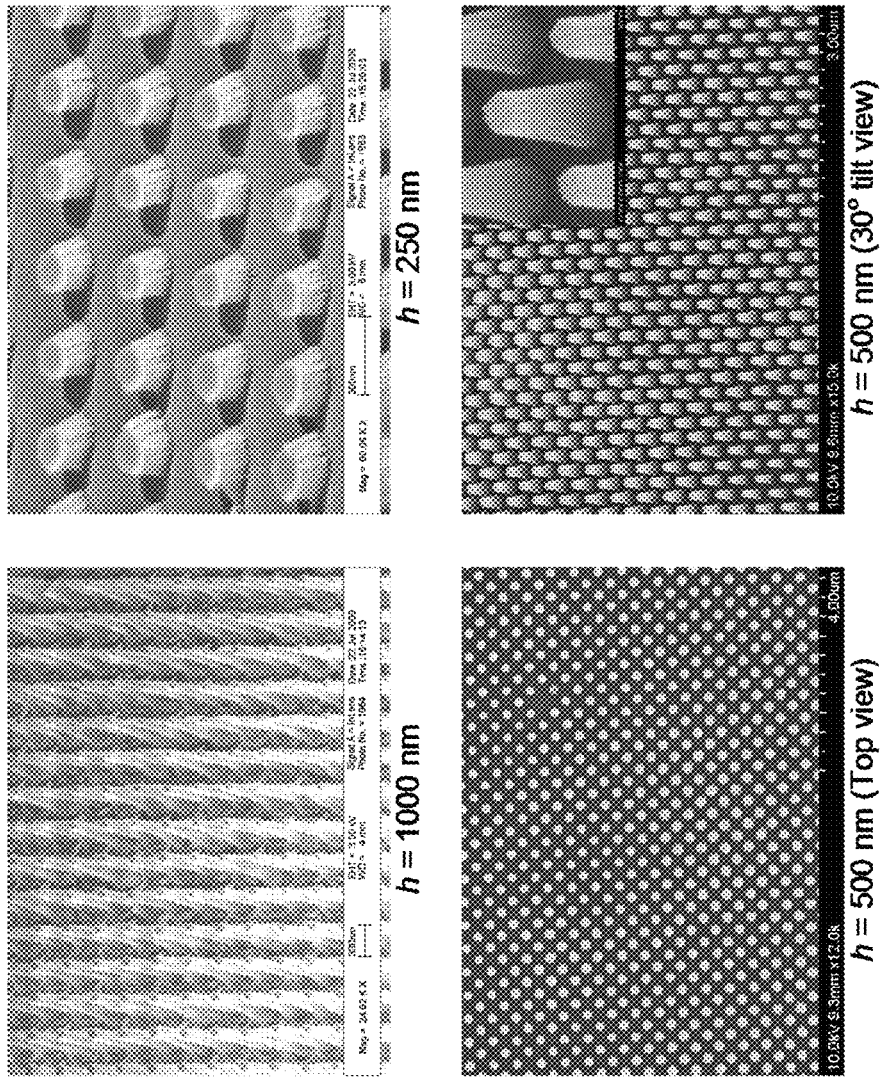
FIG. 7 shows SEM images of example embodiments of a master mold used to fabricate the sensor of the invention.

FIG. 1A depicts the schematic of the nanoLCA structure. As shown, the sensor comprises a nanofunnel-shaped cup structure with multiple nanoparticles disposed along the sidewalls. The master nanocone pattern is first fabricated on a glass substrate using a laser interference lithography technique with a range of different heights (h=250, 500 and 1000 nm), as shown in FIG. 7. The two-dimensional square lattice of nanoLCA (pitch, p=350 nm) was transferred to a flexible and optically transparent polyethylene terephthalate (PET) film using nanoreplica molding process (see Methods and FIG. 8). In order to make the structure surface plasmon active, different thicknesses, t, of a silver metal layer (t=40, 60, 70, 80, 90, 100 and 120 nm) were deposited. In order to demonstrate the apparent analogy to Lycurgus cup, FIG. 1B shows an optical image of the fabricated nanoLCA structure coated with metal (t=90 nm) with (left) and without (right) direct illumination of white light, respectively. The scanning electron micrograph ("SEM") of the nanoLCA (30° tilt and cross-sectional) is given in FIG. 1C. The metal nanoparticles on the sidewall of nanoLCA are quite apparent from the SEM images. The results obtained from nanoLCA with height, h=500 nm; diameter, d=180 nm and metal film thickness, t=90 nm; and pitch, p=350 nm showed better sensitivity and narrow spectral resonance features (compared to h=1000 nm). Due to strong interaction between surface plasmon and molecules near metal surface, surface plasmon based sensor has been widely used to exploit the plasmon-molecule interaction. One of such modalities is the refractive index sensing using surface plasmon for molecules that have no (or minimal) optical absorption or that has electronic absorption energies far away from the surface plasmon resonances. To illustrate the point, the refractive index sensing was demonstrated using fourteen different chemicals with varying refractive indices (n=1.333-1.56). As shown in FIG. 1D (top image is transmission mode and bottom image is reflection mode), the transmitted light through the nanoLCA sensor changed from light blue to green and to red with a gradual increase in the refractive index. For example, the intensity of Red channel increased to 208 (Immersion oil, n=1.51) from 18 (Air, n=1). The reflection images also showed large shift in color (from red to light green) upon the gradual increase of refractive index. Since the surface plasmon resonance peak shift is large (~100 nm) after changing the refractive index environment of the superstrate, it is possible to distinguish the chemicals from the colorful transmission images. FIG. 2B shows the mean red channel intensity (see Methods for the RGB analysis) derived from the images shown in FIG. 1D. The Earth Mover Distance (EMD) algorithm was implemented (see Methods) to compare how much the image with varying RI environment is different from that of image with water environment.

Figure 1E:
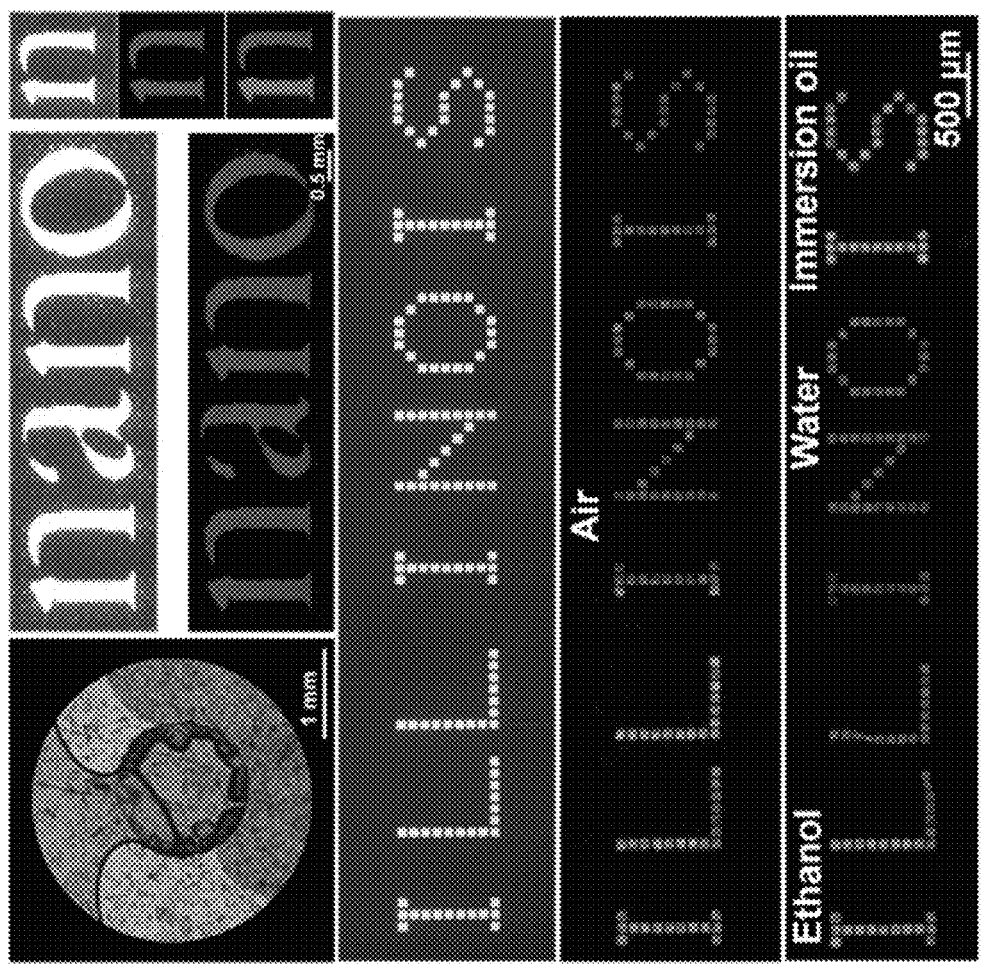
FIG. 1E shows images of example embodiments of the sensor with vibrant colors in transmission mode with a mixture of NaCl, immersion oil and ethanol. The word 'NANO' was printed on a transparency sheet and nanoLCA device was kept on top of it. Light was illuminated from the bottom of the transparency. An ethanol drop was placed on part of the letter 'N' which appears orange in the transmission image. The rest of the letter is green due to the transmission property of the apparatus. To illustrate the high spatial control, a lithography mask in quartz with the word 'ILLINOIS' was made and light was transmitted from the bottom of the mask while the nanoLCA sitting on top of it. The color appears green with air interface but changes to orange, light green and red for ethanol, water and immersion oil interfaces respectively.

In view of a large shift in the resonance wavelength due to higher sensitivity of the sensor, the refractive index change from the bright field transmission/reflection images may be monitored using a simple optical microscope with a white light source. FIG. 1E depicts structured illumination of nanoLCA using photolithographically patterned "NANO" and "ILLINOIS" mask. White light is illuminated from below the mask, but only green light passes through the nanoLCA sensor and is collected by the charge coupled device (CCD) detector of the microscope. After putting ethanol (refractive index, n=1.362) on the "IL" part of the word "ILLINOIS", the color changes from light blue to yellow. Similarly, the transmitted color changed from light blue to green and red for water and immersion oil respectively. The vibrant color created after mixing of 15% NaCl (middle orange), immersion oil (red), and ethanol (yellow) on the nanoLCA device is also shown in FIG. 1E.

Figure 2A:
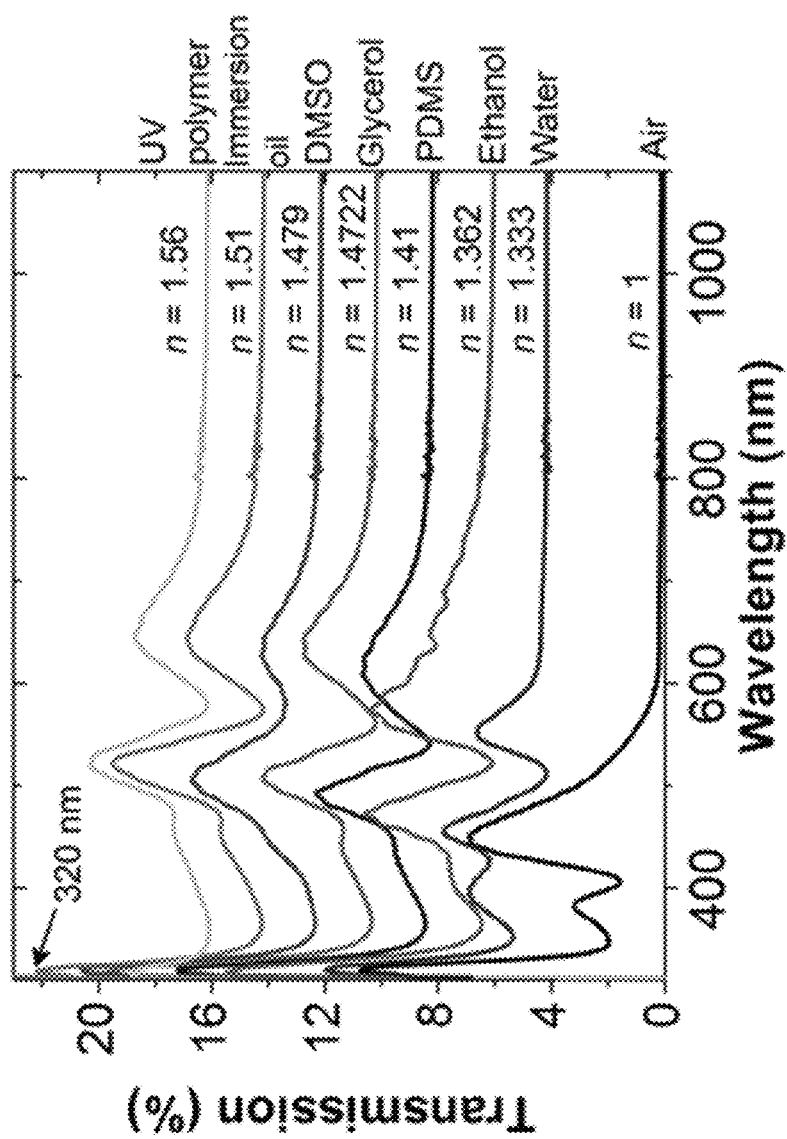
FIG. 2A shows a graph illustrating the zero-order transmission spectra of one example embodiment of the apparatus sensor (h=500, p=350 and t=90 nm) with different refractive index chemicals.
Figure 2B:
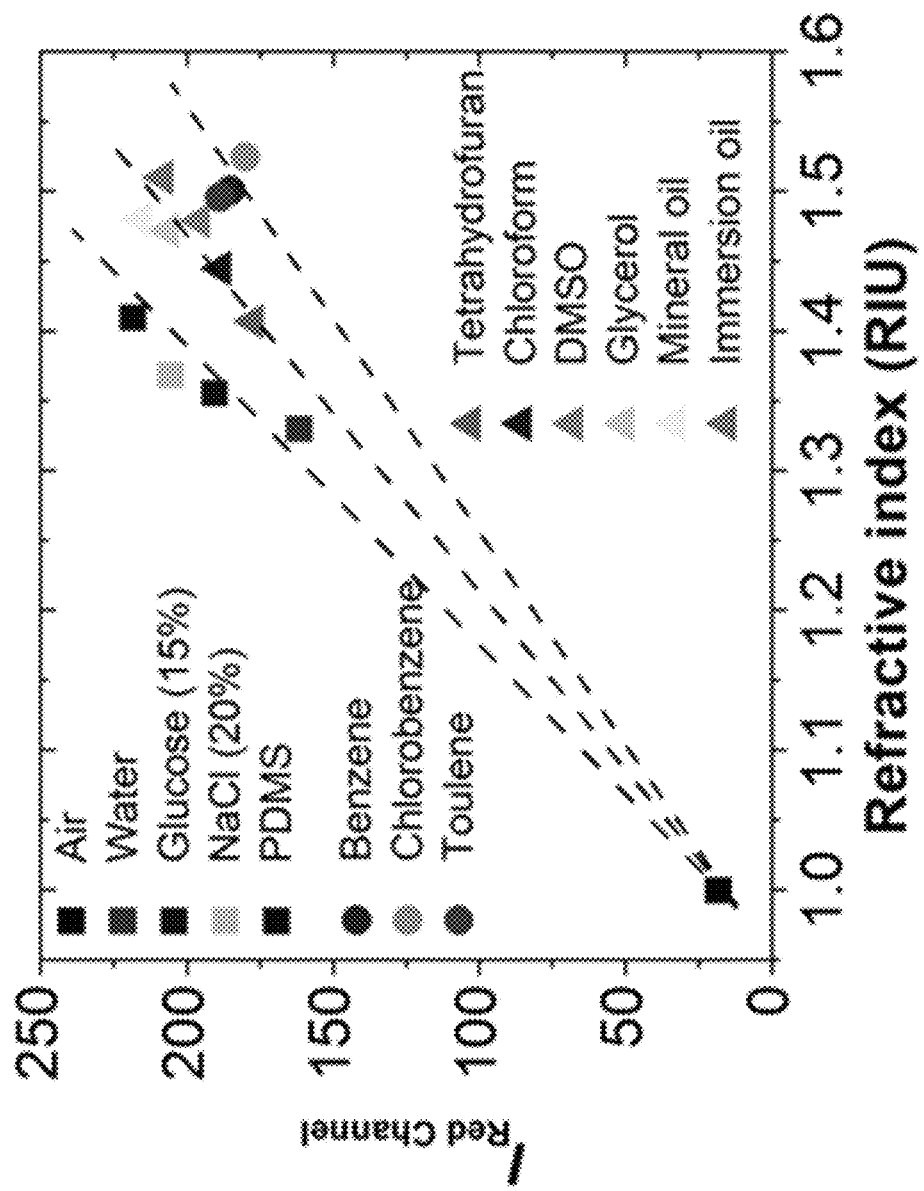
FIG. 2B shows a graph illustrating the variation of averaged red channel intensity with refractive-index.
Figure 9:
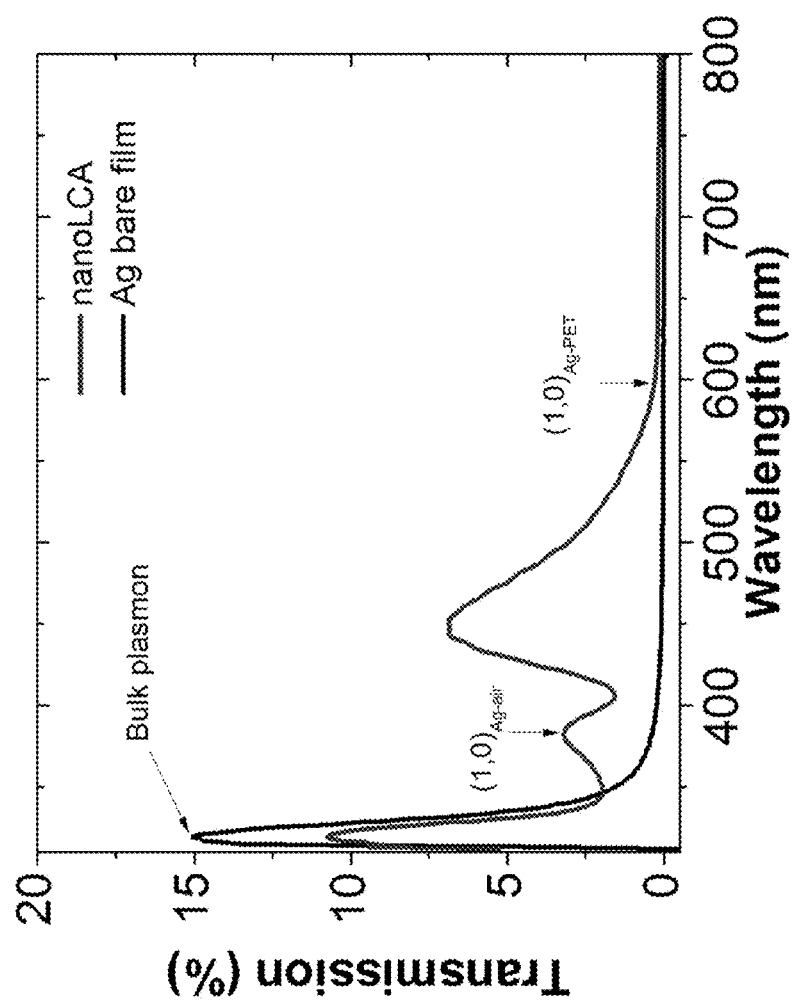
FIG. 9 shows the zero order transmission spectra of Ag bare film with a thickness t=90 nm on PET substrate and of a sensor with Ag film thickness t=90 nm, nanohole height h=500 nm and nanohole pitch p=350 nm according to one example embodiment.

FIG. 2A shows the spectroscopic results of the refractive index sensing on the nanoLCA sensor structure. The zeroth order transmission spectrum for Ag-air interface (n=1)

revealed a bulk plasmon peak for silver at λ=320 nm, as shown in FIG. 9. The peak at 2=381 nm is due to surface plasmon polariton-Bloch wave (SPP-BW) (1,0) mode at Ag-air interface (n=1). The SPP-BW and Wood's anomaly (WA) (due to the diffraction of light parallel to the surface) for a rectangular lattice structure can be approximately calculated using the relation:

$$\lambda_{SPP-BW} = \frac{p}{\sqrt{i^2+j^2}} \sqrt{\frac{\varepsilon_{Ag}(\lambda)\varepsilon_d}{\varepsilon_{Ag}(\lambda)+\varepsilon_d}} \quad (1)$$

$$\lambda_{WA} = \frac{p}{\sqrt{i^2+j^2}} \sqrt{\varepsilon_d} \quad (2)$$

where, i and j are the order of SPP-BW or WA. The dip at λ=350 nm is due to (1,0) WA at Ag-air interface. The intense peak at λ=450 nm cannot be predicted by any lowest order SPP-BW or WA from the calculation. However, using Mie scattering calculation (see Methods), the peak at λ=450 nm was found to be due to the scattering from Ag nanoparticles with diameter d=50 nm in PET environment (n=1.56). Upon changing the refractive index of the superstrate from air (n=1) to higher refractive indices solutions, the result showed that the bulk plasmon peak at λ=320 nm remains unchanged (FIG. 2A); the SPP-BW and WA features are red shifted, and the Mie scattered LSPR peak was red shifted by 100 nm for water (n=1.333) and by almost 200 nm for immersion oil (n=1.51).

The asymmetric nature of the spectrum also indicates the interference between SPP-BW, WA and scattered light from the nanoparticles transmitted by the nanoholes. Since the boundary conditions and interfaces at each side of the metal (metal-substrate (n=1.56) and metal-superstrate (e.g. n=1)) are different and each side of the nanoLCA can support excitation of surface plasmon, the asymmetric structure leads to two sets of transmission peaks. However, the intensity of the Mie scattered peak is much stronger than the supported SPP-BW peaks and hence, only single color is being transmitted by the nanoLCA structure. In addition, the index-matching layer (n=1.56) covering the nanoLCA structure leads to similar coupling efficiency for the two modes and manifested in transmission peaks of similar intensities (FIG. 2A).

Figure 2C:
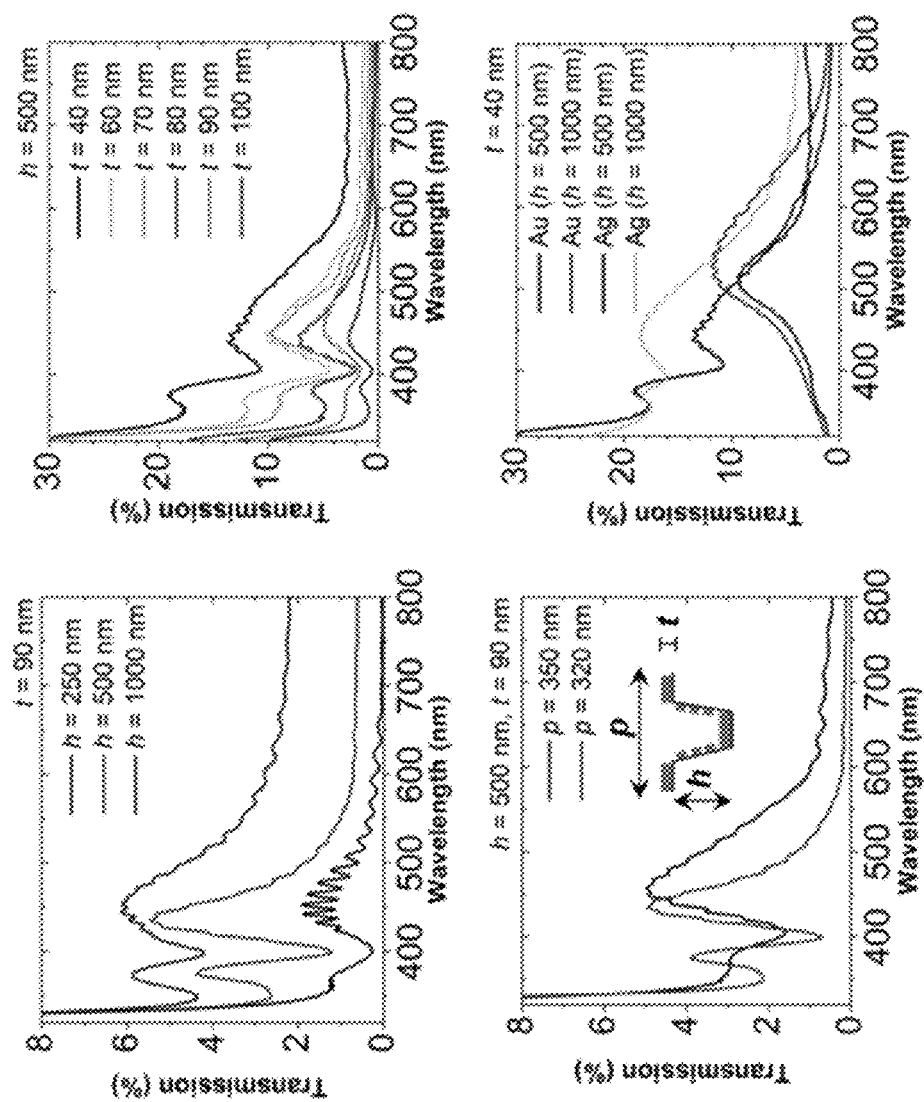
FIG. 2C shows a graph (top left) illustrating the zero-order transmission spectra for three example embodiments of the sensor with different heights of nanoholes, h=250 nm (black, bottom), h=500 nm (red, middle), and h=1000 nm (blue, top) and each with a thin metal film of Ag having a thickness of t=90 nm.
Figure 2D:
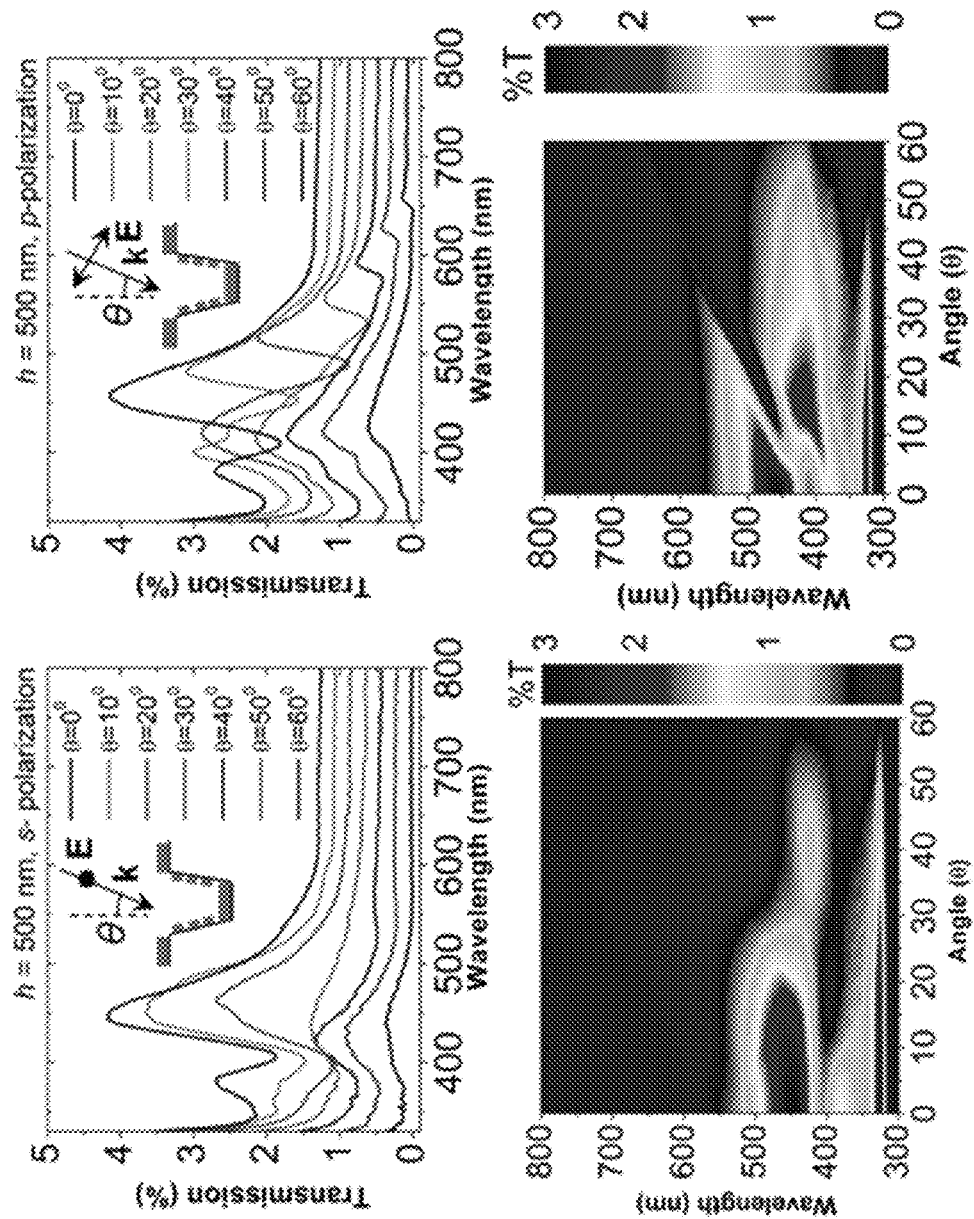
FIG. 2D is a graph showing the measured transmission spectra of nanoLCA in s-polarized (top left) and p-polarized light (top right). The incident angle was varied from θ=0° to θ=60°. The corresponding dispersion curve for each polarization is also presented as a contour plot (bottom) with the angle of incidence varied with an increment of 10.
Figure 10:
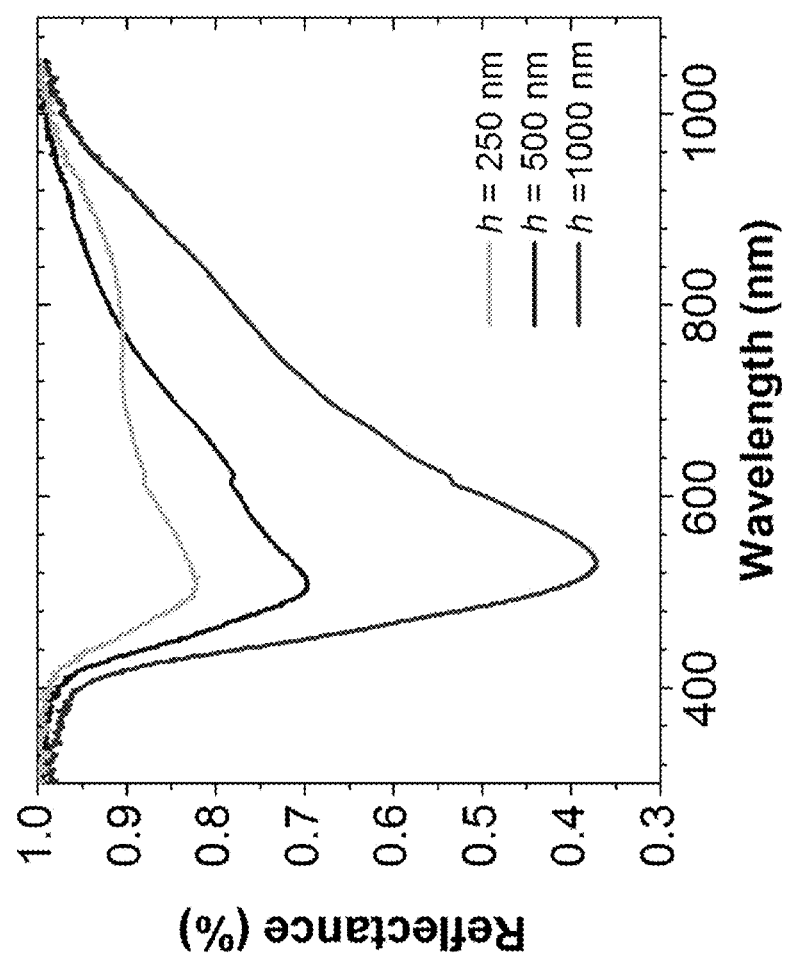
FIG. 10 shows the effect of nanohole depth on the Q-factor of a sensor according to one example embodiment. The reflectance dip becomes sharper indicating a higher Q-factor as the height of the nanoholes is increased.
Figure 11:
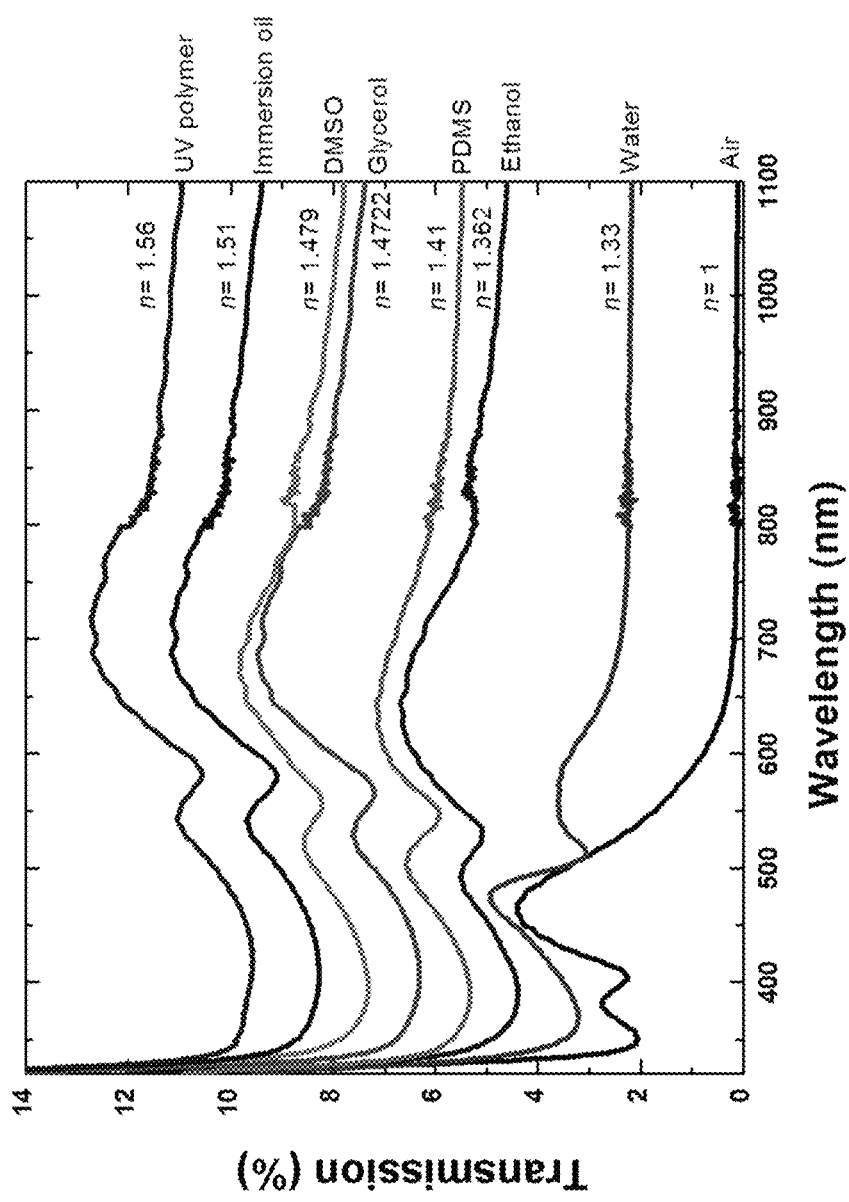
FIG. 11 shows a graph illustrating the transmission spectrum of an example embodiment of a sensor having a nanohole height h=1000 nm with chemicals of different refractive indices applied as a superstrate. The SPP-BW peak and the Mie scattering LSPR peak red shifted with increase of refractive index of the superstrate.
Figure 12:
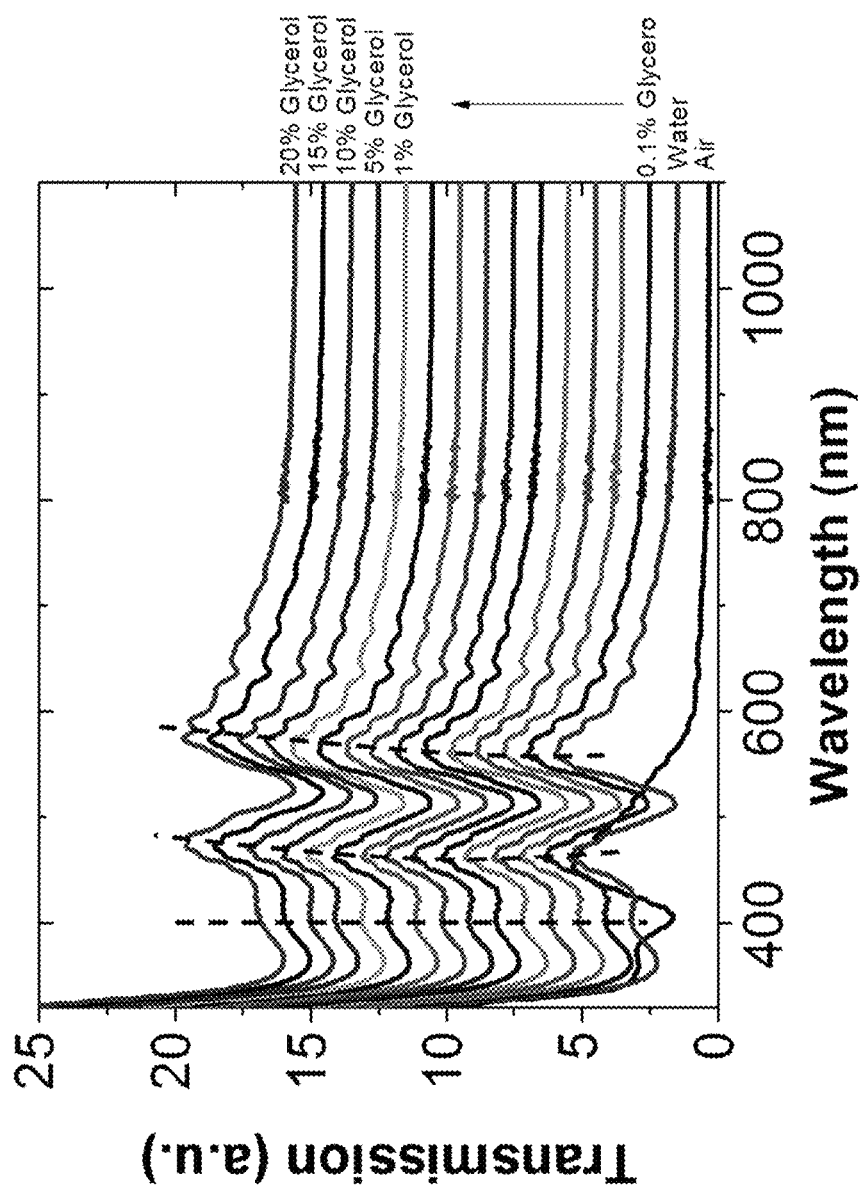
FIG. 12 shows a graph illustrating the transmission spectra of an example embodiment of a sensor having a nanohole height h=500 nm with different concentrations of Glycerol solution. The LSPR mode (~λ=560 nm) is red-shifted as the Glycerol concentration increases (0-20% by weight).
Figure 13A:
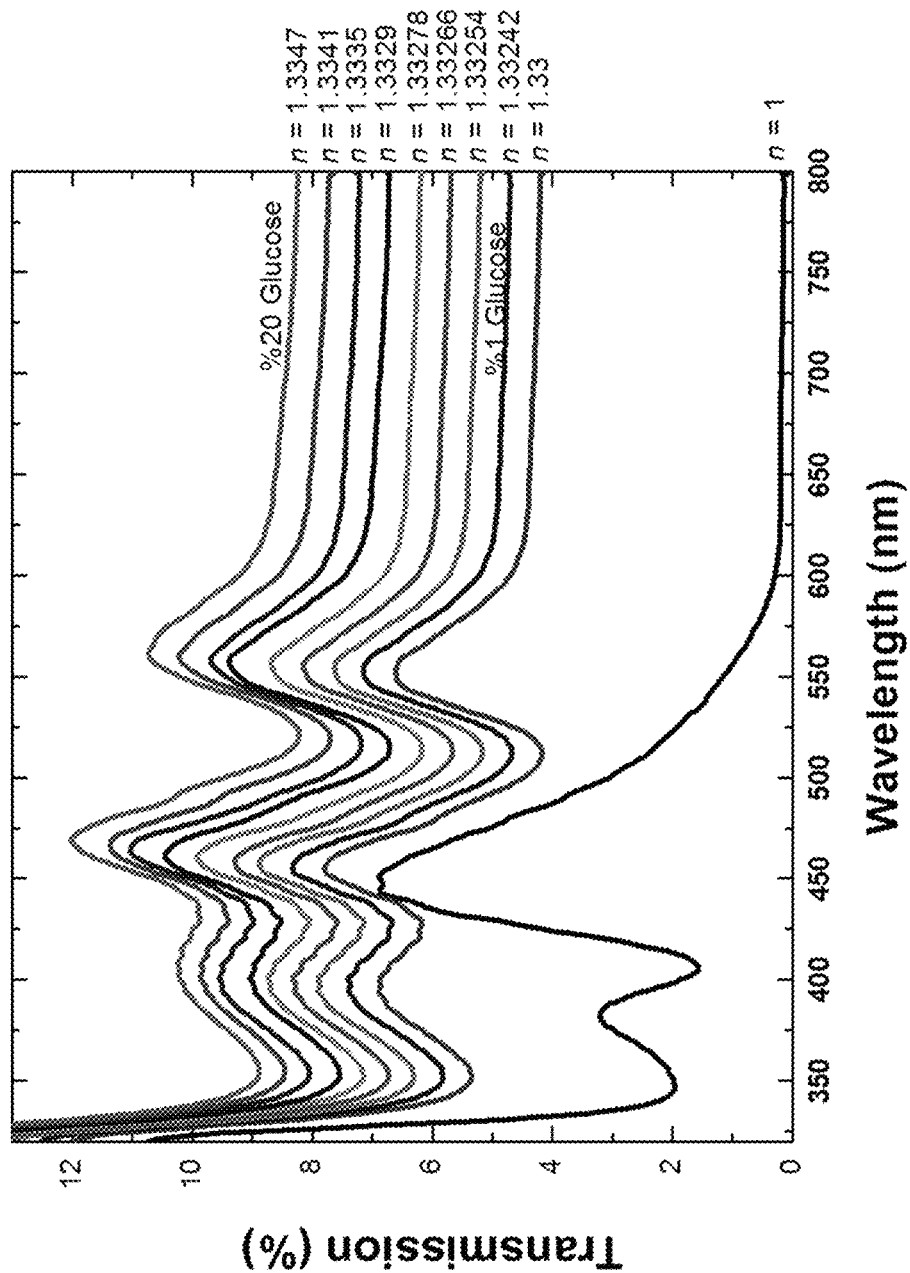
FIG. 13A is a graph that illustrates the transmission spectra of a sensor having a nanohole height h=500 nm with different concentrations of Glucose solution according to one example embodiment.
Figure 13B:
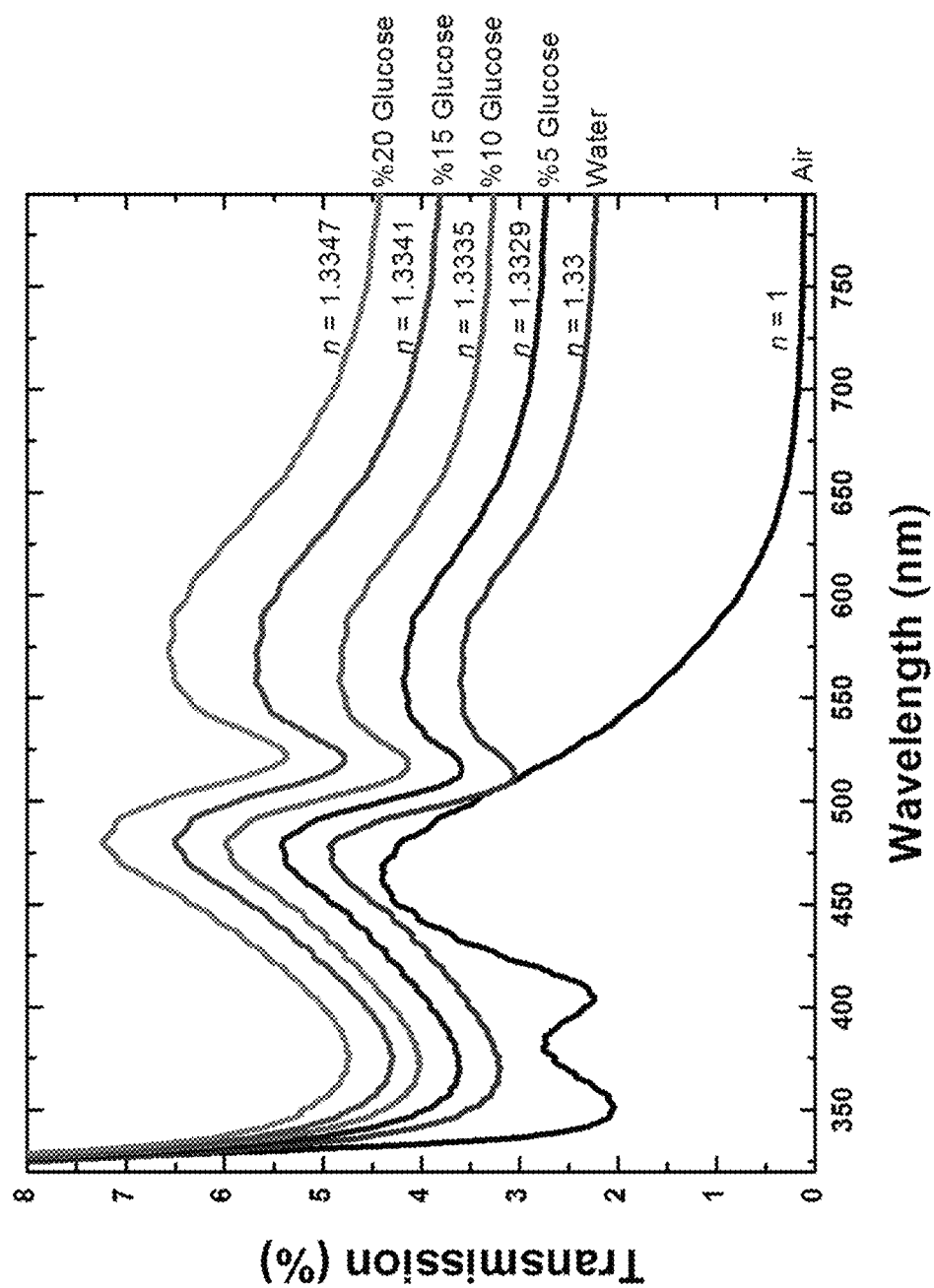
FIG. 13B is a graph that illustrates the transmission spectra of a sensor having a nanohole height h=1000 nm with different concentrations of Glucose solution according to one example embodiment.
Figure 14A:
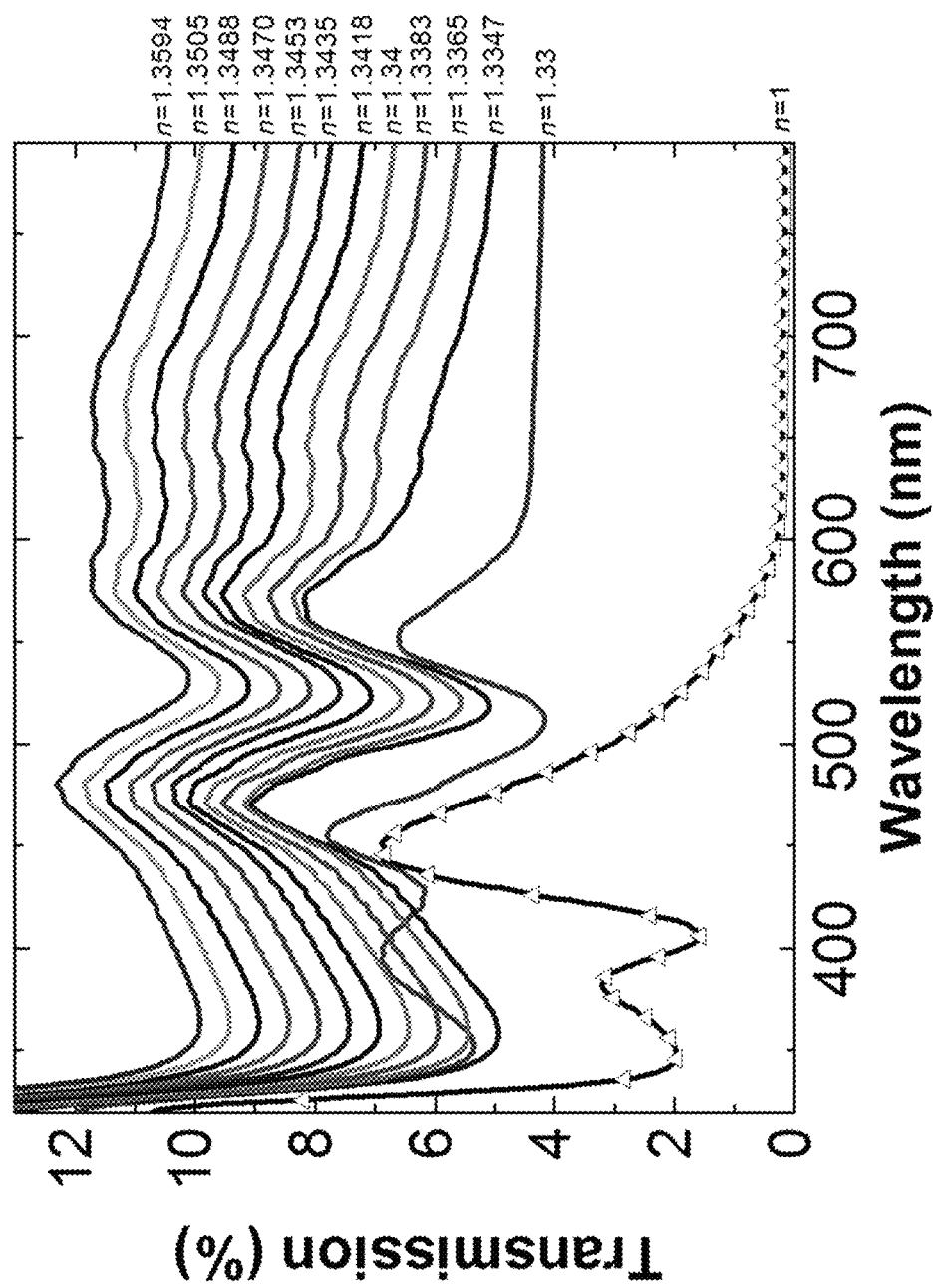
FIG. 14A is a graph that illustrates the transmission spectra of a sensor having a nanohole height h=500 nm with different concentrations of NaCl solution according to one example embodiment.
Figure 14B:
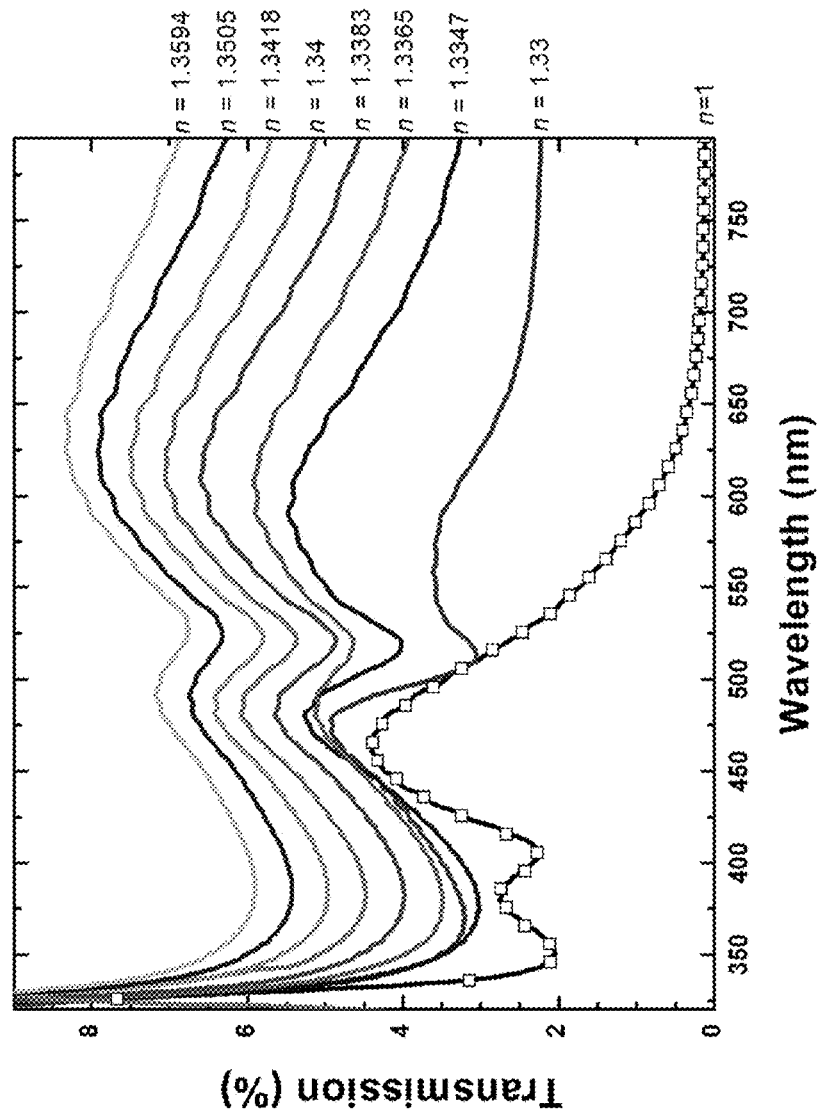
FIG. 14B is a graph that illustrates the transmission spectra of a sensor having a nanohole height h=1000 nm with different concentrations of NaCl solution according to one example embodiment.
Figure 15:
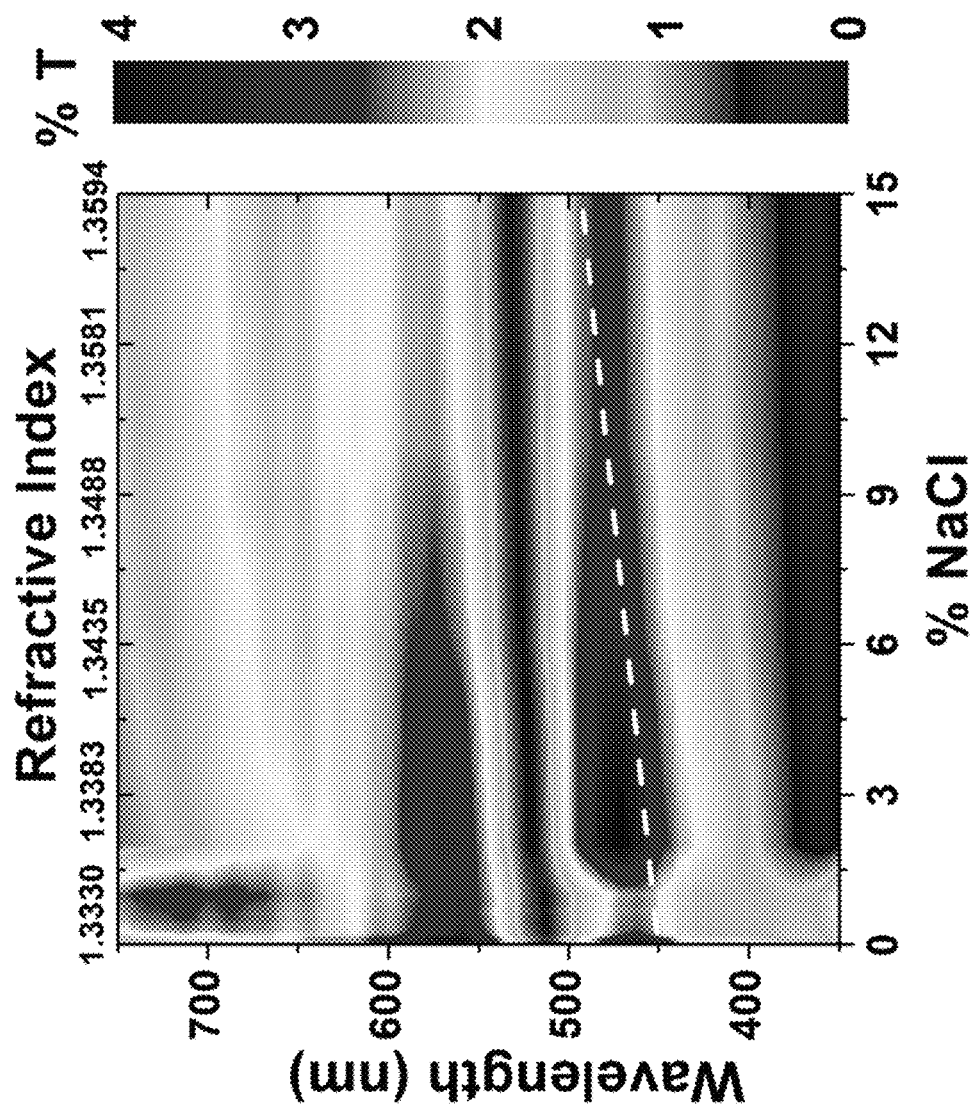
FIG. 15 is a contour plot illustrating the transmission spectra of a sensor having a nanohole height h=500 nm with different concentrations of NaCl solution according to one example embodiment.

Further detailed optical characterization was carried out to reveal the property of nanoLCA. FIG. 2C demonstrates the ability to control the resonance peak position by changing the height, h, and the pitch, p, of the nanoholes independently. The transmission intensity can be tuned by changing the metal thickness, t. The Q-factor of the sensor can be tuned by changing the height of the nanohole, as shown in FIG. 10. The peak position can also the tuned by changing the nanohole diameter (by employing different RI UV cure polymer during the replica molding process). The angular and polarization dependent property of the nanoLCA sensor is shown in FIG. 2D. In normal transmission (θ=0°), the transmission spectrum shows two pronounced peaks at λ=381 nm and λ=450 nm. However, increasing the angle of incidence from θ=0° to θ=60°, the intensity of peak at λ=381 nm gradually decreases for s-polarization. Also, the peak at λ=450 nm blue-shifted to higher energy upon increasing the incident angle for s-polarization. However, for p-polarization both the peaks at λ=381 nm and λ=450 nm shifted to lower energy (red shifted) with the increase in incidence angle. Also, for p-polarization, the coupling to SPP-BW becomes much stronger than the LSPR modes with increasing the angle of incidence. The appearance of λ=450 nm peak for s-polarization gives further indication that the peak at λ=450 nm is a LSPR peak as SPP should not be excited efficiently by s-polarized incident light.

Figure 3B:
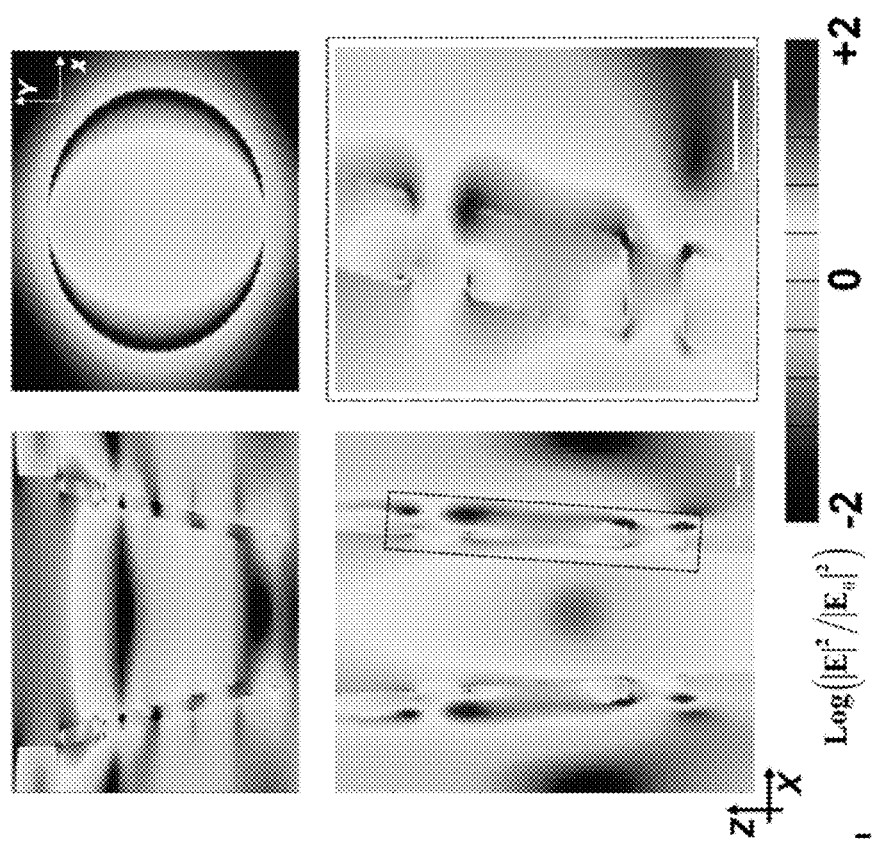
FIG. 3B shows the electric field distribution for a side view of for a nanohole (top left), a cross-sectional side view for the nanohole (X-Z, bottom left), a top view for the nanohole (X-Y, top right) and a detail view of a plurality of nanoparticles disposed on the sidewall of the nanohole (X-Z, bottom right).
Figure 3C:
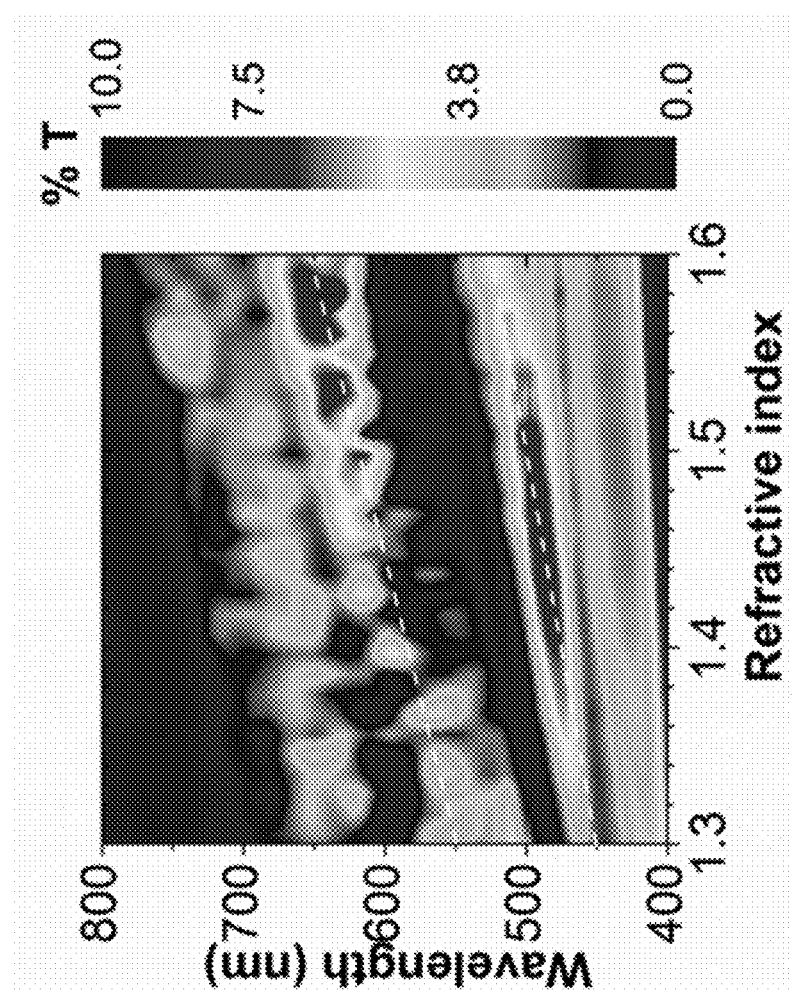
FIG. 3C shows an FDTD simulated contour plot illustrating the variation of transmission spectra by changing the refractive index ("RI") of surrounding medium for example embodiments of the sensor. The results show two distinct peaks with increasing RI. Also, the first peak red-shifted from $\lambda=450$ nm to $\lambda=525$ nm and the second peak is red-shifted from $\lambda=550$ nm to $\lambda=650$ nm with the increase of RI.
Figure 3D:
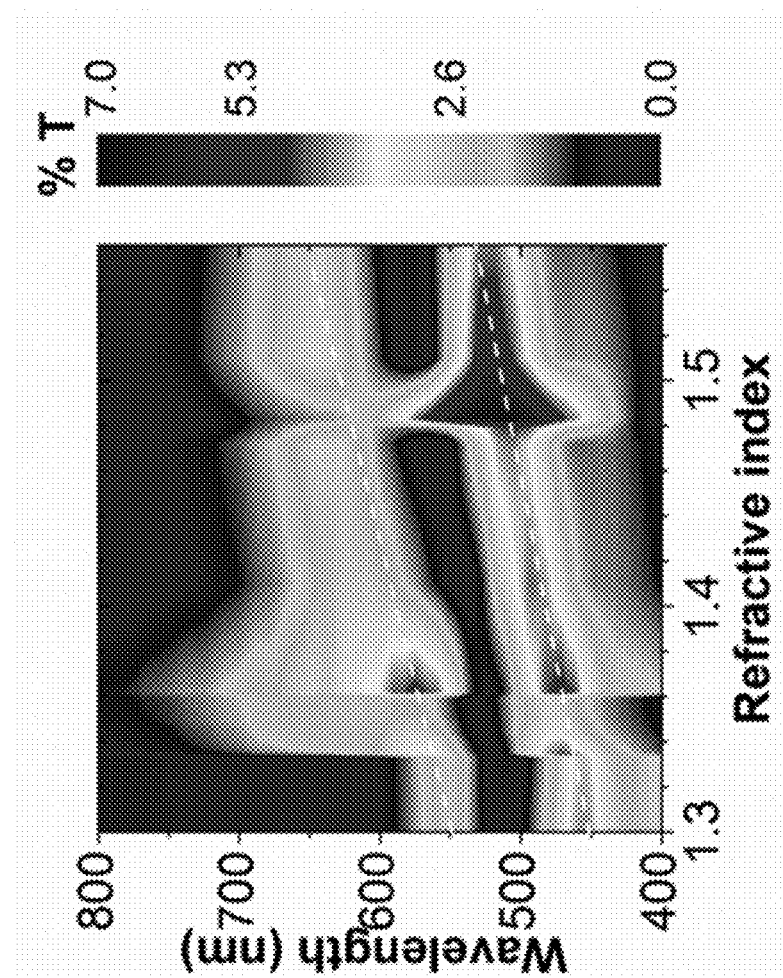
FIG. 3D shows a contour plot illustrating the experimentally obtained variation of transmission spectra by an example embodiment of the sensor in the presence of different RI liquids. The experimental contour plot showed remarkable resemblance to the FDTD simulated contour plot with appearance of two distinctive peaks and similar red-shift of resonance peaks.

To further understand the physics behind the experimental observations, full 3-D finite difference time domain ("FDTD") simulations are performed. To highlight the importance of nanohole shape and the side wall nanoparticles, five different nanohole shapes (labeled 1-5) are simulated in FIG. 3A. As expected, nanohole without metal film on the sidewalls and continuous metal film on the side walls (similar to quasi 3D plasmonics crystal or EOT structures) shows multiple transmission peaks in the simulation (case 1-3) and do not match with the experimental observations. However, with incorporation of discrete metal film on the sidewalls and multiple particle-like structures (case 4 and 5) as the analogy to the Lycurgus cup, similar peak features were observed as in the experiment (the slight discrepancy in the experiment and simulations were due to the difficulties in exactly simulating the randomly deposited nanoparticles on the wall). The intense peak at λ=450 nm is due to the LSPR mode at the gap between the nanoparticles and at the rim of the nanoLCA. The corresponding variation in the electric field intensity ($|E|^2$) is shown in FIG. 3B. The top (X-Y) and cross-sectional (X-Z) views of the intensity distribution represent the electric field enhancement ($Log|E/E_{inc}|^2$) associated with the corresponding plasmon resonances. The LSPR mode of the particle at Ag-PET interface at λ=450 nm is clearly visible in FIG. 3B. The cavity mode (SPP-BW) can also be found in FIG. 3B. In order to predict the sensitivity of the device to refractive index variation of the surrounding medium, a simulation was performed to calculate the transmission spectrum by changing the refractive index of superstrate disposed on the nanoLCA sensor. FIG. 2C shows the simulated variation of transmission as a function of refractive index (RI) of the surrounding medium. As observed in the experiment, the simulation results also showed red shift of both modes (SPP-BW and LSPR) with RI increase. The corresponding measured variation of transmission as a function of RI is shown in FIG. 2D. The simulation results are strikingly similar with the experimental results about the appearance of two peaks and red shifting with the increase of RI.

Figure 4B:
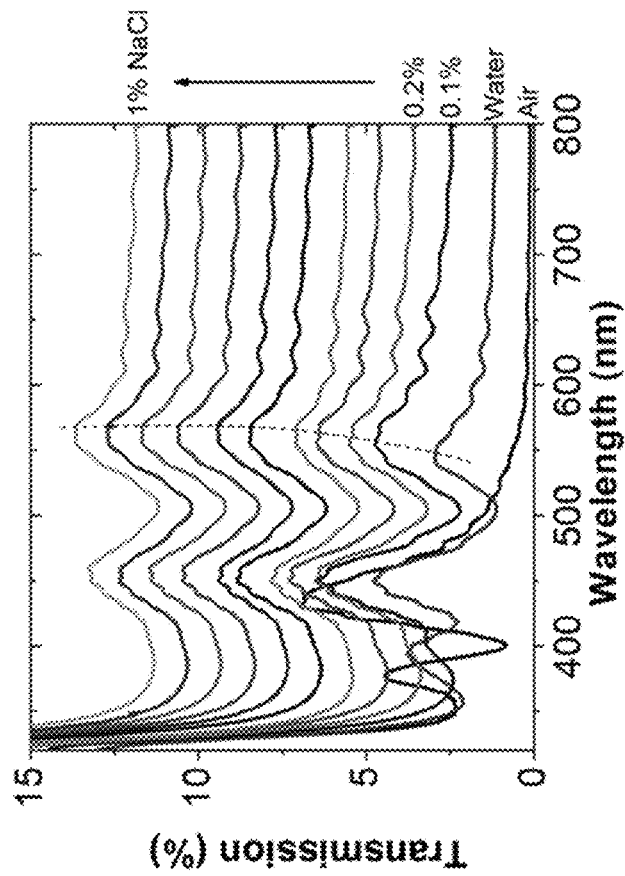
FIG. 4B shows a graph illustrating the transmission spectra of an example embodiment of the sensor in the presence of NaCl concentration of 0-1% with an increment of 0.1%. The LSPR resonance peak due to Mie scattering of nanoparticles along the sidewall (shown with dotted line) are red-shifted with a change in NaCl concentration.
Figure 4A:
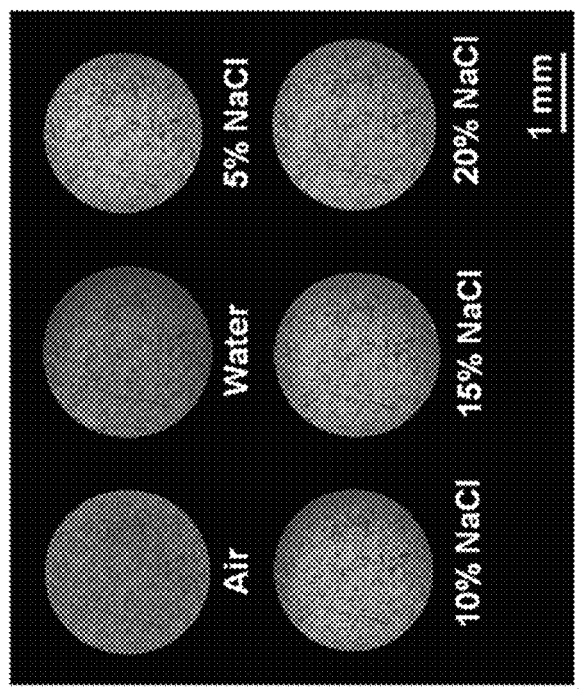
FIG. 4A is an optical micrograph of an example embodiment of the sensor having a height of h=500 nm and a thin metal film with a thickness of t=90 nm with different concentrations of NaCl solutions (0-20% by weight).
Figure 4C:
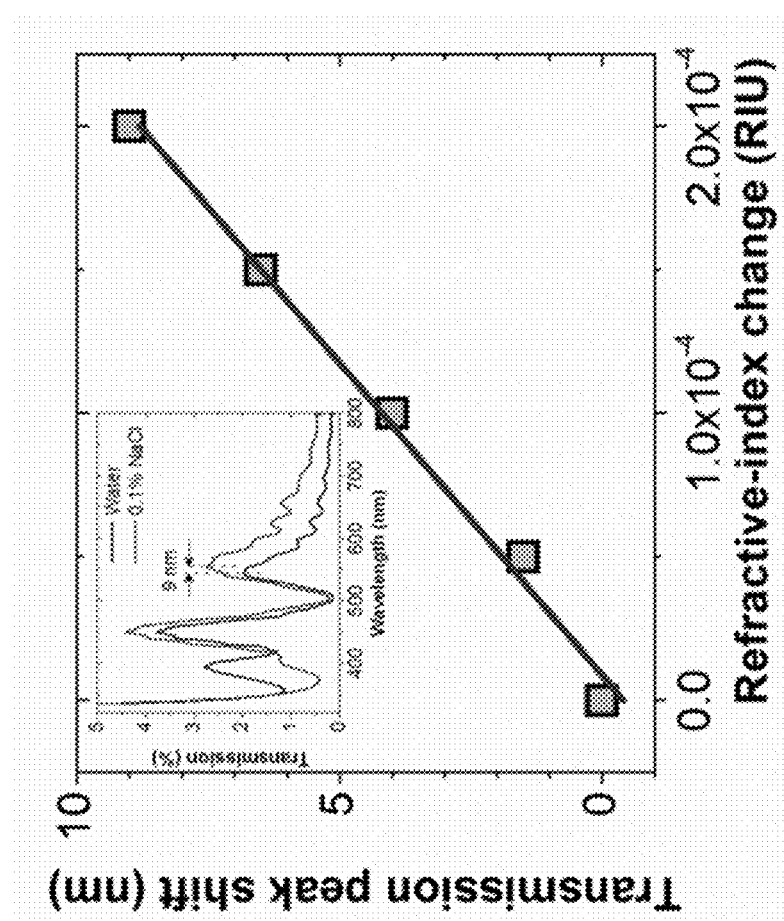
FIG. 4C is a graph showing the sensitivity of an example embodiment of the sensor calculated using a linear fitting scheme from the transmission spectra LSPR resonance peak shift obtained for NaCl concentration of 0-0.1% with an increment of 0.025%. The sensitivity was calculated to be 46,000 nm per RIU.
Figure 4D:
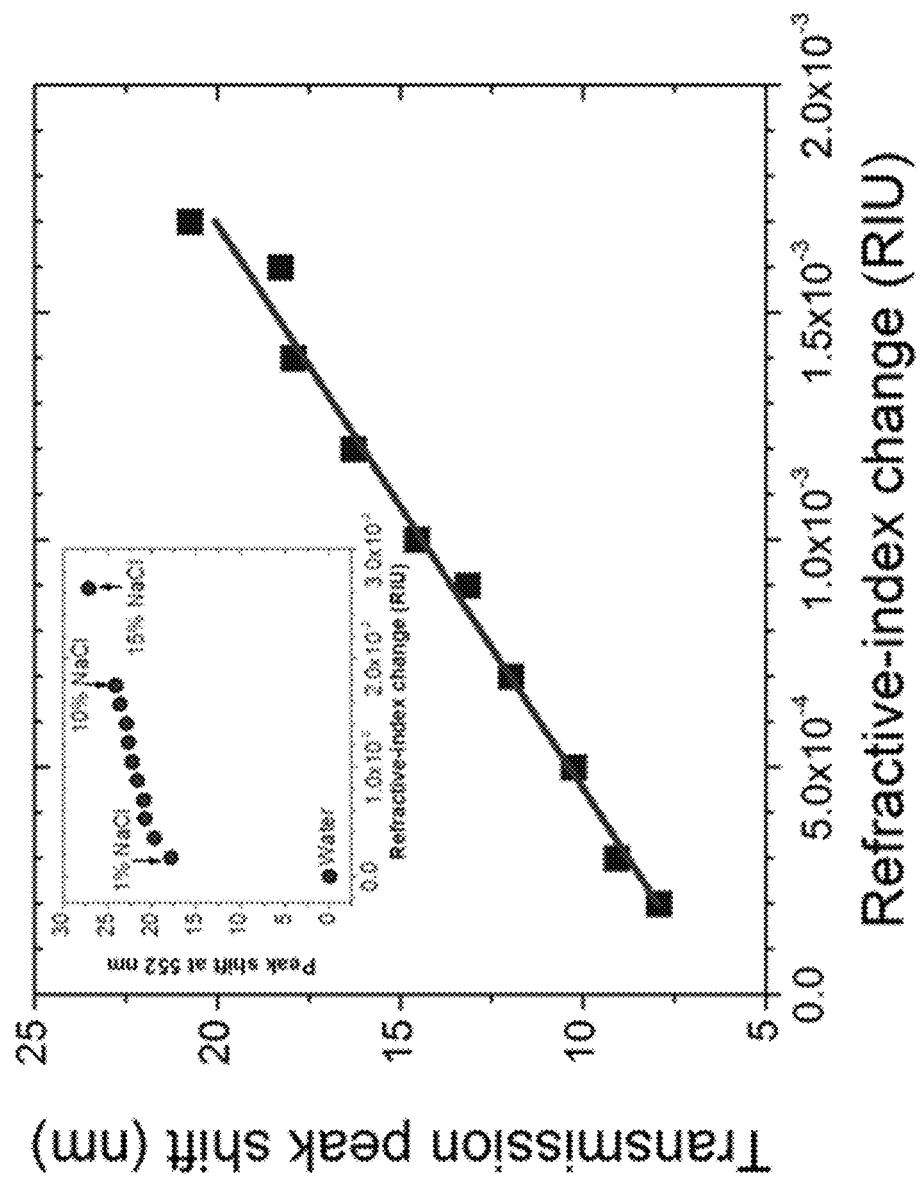
FIG. 4D is a graph showing the sensitivity of an example embodiment of the sensor calculated for NaCl concentration ranging from 0-1%. The average sensitivity in a high concentration range was calculated to be 8066 nm per RIU. The inset shows the LSPR resonance peak shift for the sensor for NaCl concentration ranging from 0-15%. The large peak shift at a lower concentration clearly demonstrates that the sensor is more sensitive in a lower concentration range.

In order to compare the sensitivity of the nanoLCA sensor, the LSPR peak wavelength shift was measured by precisely varying the concentration of NaCl solution. At low concentration (<1 mg mL$^{-1}$ or 0.1% NaCl), with a difference of RI by 2×10$^{-4}$ RIU (refractive index unit) wavelength shift of LSPR mode was observed to be ~9 nm (FIG. 4C), which corresponds to sensitivity of 46000 nm RIU$^{-1}$, exceeding all previously reported sensitivity by almost two orders of magnitude. An average sensitivity of 8066 nm RIU$^{-1}$ ($R^2$=0.987) was achieved for higher concentration (>1 mg mL$^{-1}$ or 0.1% NaCl) (FIG. 4D). In order to compare the sensitivity of different metallic plasmonic sensors, a metric called figure of merit (FOM), $$\frac{\Delta\lambda}{\Delta n}\left(\frac{1}{\Delta w}\right),$$

where Δλ is the amount of shift for the resonance peak wavelength for Δn is the change in the RI, Δw is the full-width-half-maximum (FWHM) of the peak in consideration, is widely used. A maximum FOM of ~1022 and an average FOM~179 were calculated, which far exceeds all reported FOM of nanohole structures (including the theoretical upper limit of FOM~108 for gold standard SPR sensors; metallic naoparticles has FOM~0.9-5.4 and SPP structure has FOM~23). The high sensitivity is due to selective transmission of nanoparticle scattering light by the nanoLCA sensor. There is also contribution from subradiant (long plasmon lifetime) SPP waves (at $\lambda$=381 nm) (with a narrow full width at half maximum of 18 nm). Due to longer plasmon lifetime, the plasmon energy can be transferred to the emissive superradiant LSPR mode (at $\lambda$=450 nm) (with FWHM of 48 nm) giving rise to further enhancement of local electric field. The corresponding bright-field image with different NaCl concentration is shown in FIG. 4A. Typical spectrum for low concentration of NaCl solution is reported in FIG. 4B. Transmission spectra obtained using other height (h=1000 nm) and chemicals (glycerol, glucose, NaCl) are reported in FIGS. 11-15.

Figure 16:
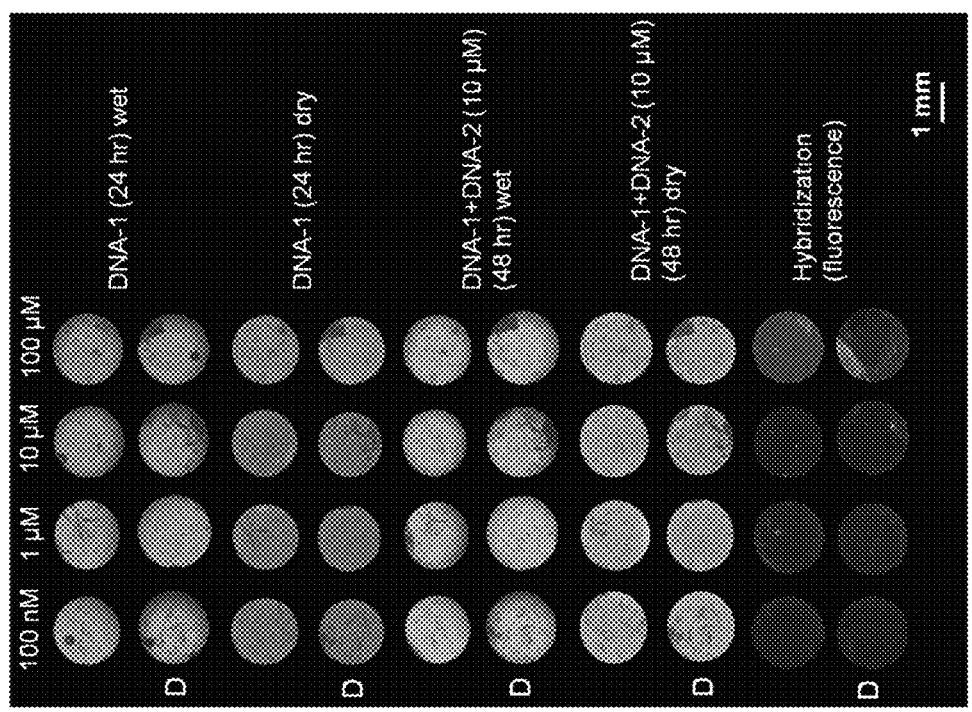
FIG. 16 is a bright field image of DNA in a high concentration limit. The concentration of "probe" DNA (5'-thiol-CAGCAAATGGGCTCCGAC-3'; SEQ ID NO: 01) or DNA-1 was varied (100 nm to 100 μM) using DI water. The first two rows are images of an example embodiment of the sensor after 24 hours of incubating DNA-1 solutions. "D" denotes duplicates. The third and fourth rows are images after washing and drying DNA-1. The fifth and sixth rows are images of an example embodiment of the sensor after 24 hours of incubating DNA-2 (3'-GTCGGAGC-CCATTTGCTG-5'-HEX; SEQ ID NO: 02) solution. The last four rows are the hybridization state in bright field and fluorescence imaging mode, respectively.
Figure 17:
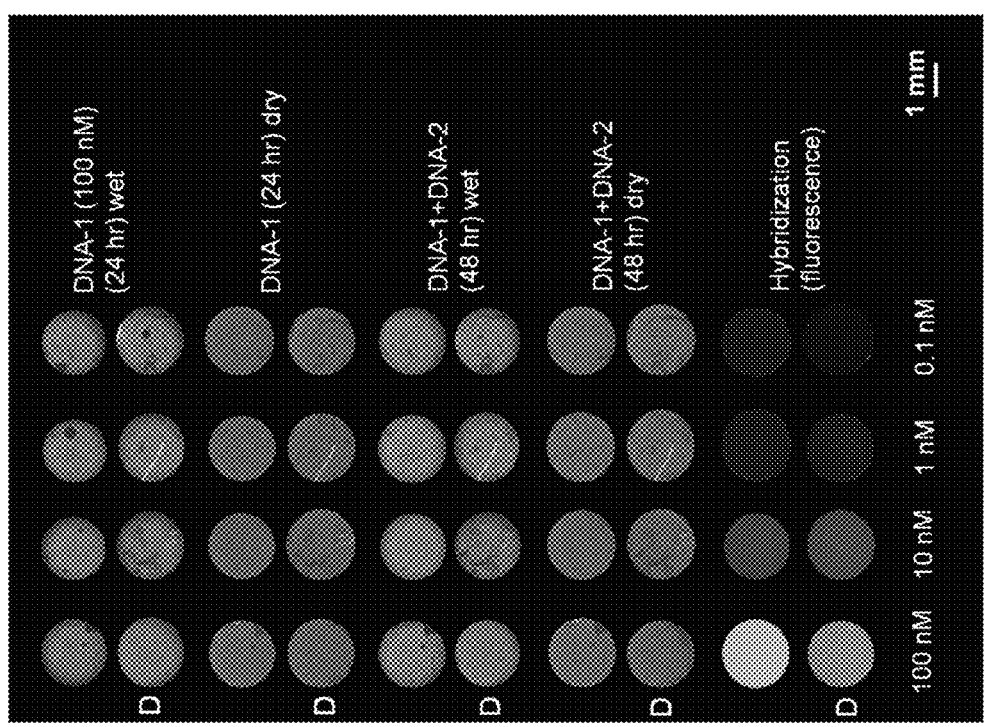
FIG. 17 is a bright field image of DNA in a low concentration limit. The concentration of "targer" DNA (3'-GTCG-GAGCCCATTTGCTG-5'-HEX; SEQ ID NO: 02) or DNA-2 was varied (100 μM to 100 nM) using 1×PBS. The first two rows are images of an example embodiment of the sensor after 24 hours of incubating DNA-1 (100 nM) solutions. "D" denotes duplicates. The third and fourth rows are images after washing and drying DNA-1. The fifth and sixth rows are images of an example embodiment of the sensor after 24 hours of incubating DNA-2 (3'-GTCG-GAGCCCATTTGCTG-5'-HEX; SEQ ID NO: 02) solution. The last four rows are the hybridization state in bright field and fluorescence imaging mode, respectively.
Figure 18:
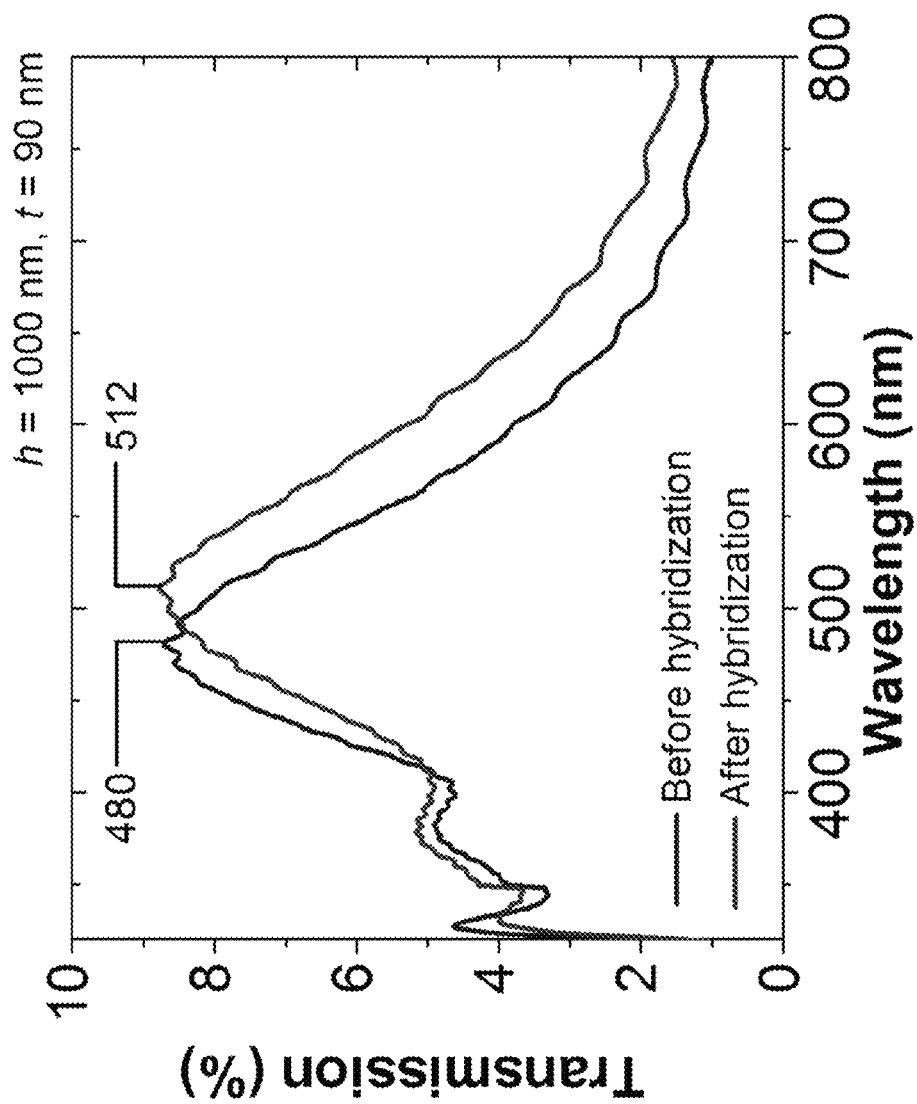
FIG. 18 is a graph illustrating the transmission spectrum of a sensor having a nanohole height h=1000 nm according to one example embodiment before and after DNA hybridization. The concentration of DNA-1 solution was 100 μM (prepared in DI water) and the concentration of DNA-2 solution was 10 μM (prepared in 1×PBS).

To demonstrate the utility of nanoLCA for biosensing applications, the hybridization of a short chain of probe oligonucleotides (5'-thiol-CAGCAAATGGGCTCCGAC-3' SEQ ID NO: 01) and its perfectly matched target oligonucleotide (3'-GTCGGAGCCCATTTGCTG-5'-HEX; SEQ ID NO: 02) were measured. The 5' end of the probe oligonucleotides was modified with a thiol group for ease of immobilizing on Ag surface. The colorimetric SPR imaging technique of the invention does not require any label on the DNA, however, the target oligo was tagged with fluorophore HEX for independently verifying the hybridization in fluorescence mode. FIG. 5A shows the detection of hybridization of oligonucleotides down to 100 pM through the BF imaging of nanoLCA. The colorless DNA was capable of being visualized and the concentration of DNA was capable of being differentiated based on the color change of the sensor device (raw images are shown in FIGS. 16 and 17). The transmission spectrum showed a red-shift of ~32 nm after DNA hybridization for the nanoLCA with h=1000 nm (FIG. 18).

Figure 5B:
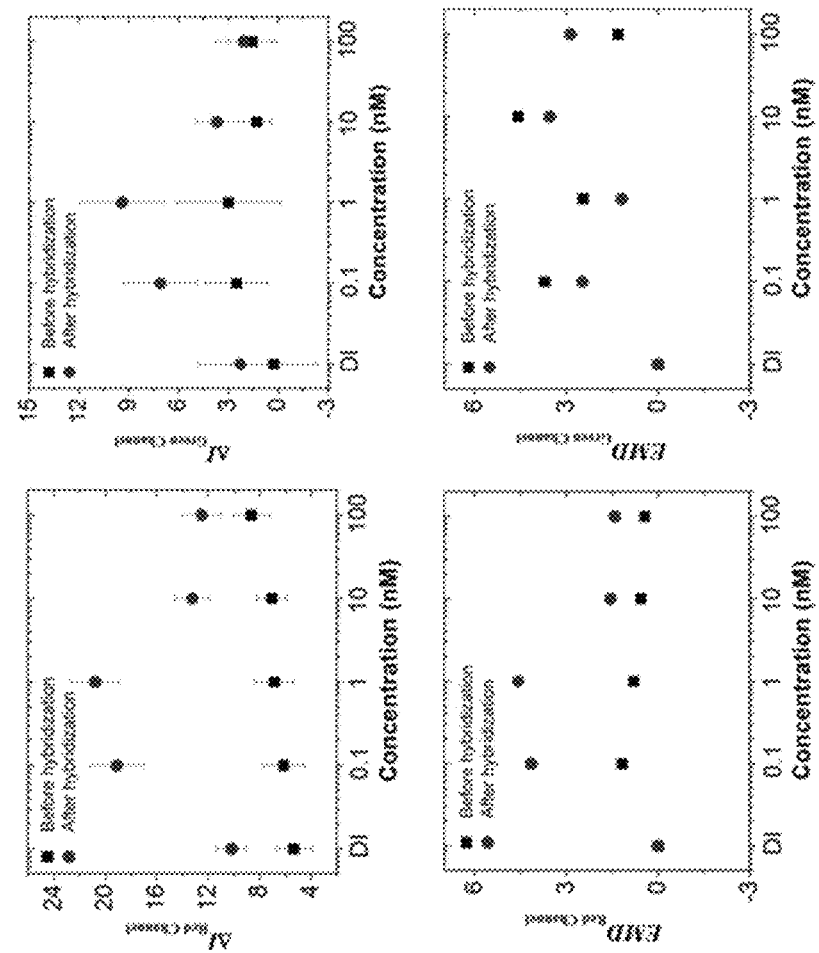
FIG. 5B is a series of graphs showing the variation of red and green channel intensity with different concentration of oligonucleotides before and after hybridization (top) and the variation of EMD counts with concentration for red and green channel (bottom).
Figure 5A:
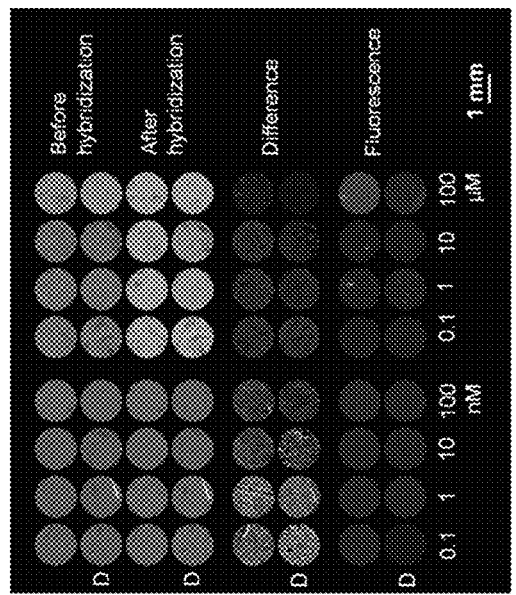
FIG. 5A shows bright field images of short chain oligonucleotides before and after hybridization. Here 'D' denotes duplicate experiments. The difference shows the direct subtraction of 'before hybridization' images from the 'after hybridization' images. Here, orange color (left) denotes higher count than blue color (right).

As shown in FIG. 5B, the hybridization of target oligonucleotide at 0.1 nM and 1 nM to the probe oligonucleotide resulted in approximately 1.9 and 2.1 times increase respectively in the intensity of the red channel compared to that of the negative control. Likewise, in the green channel, approximately 3.3 and 4.3 times increase was observed after the hybridization of the same concentrations of probe oligonucleotide. The difference in red channel intensity and EMD values are much more sensitive in lower concentration range compared to higher concentration, at which the sensor is more likely saturating (confirming an earlier observation about RI-solution testing).

Figure 19:
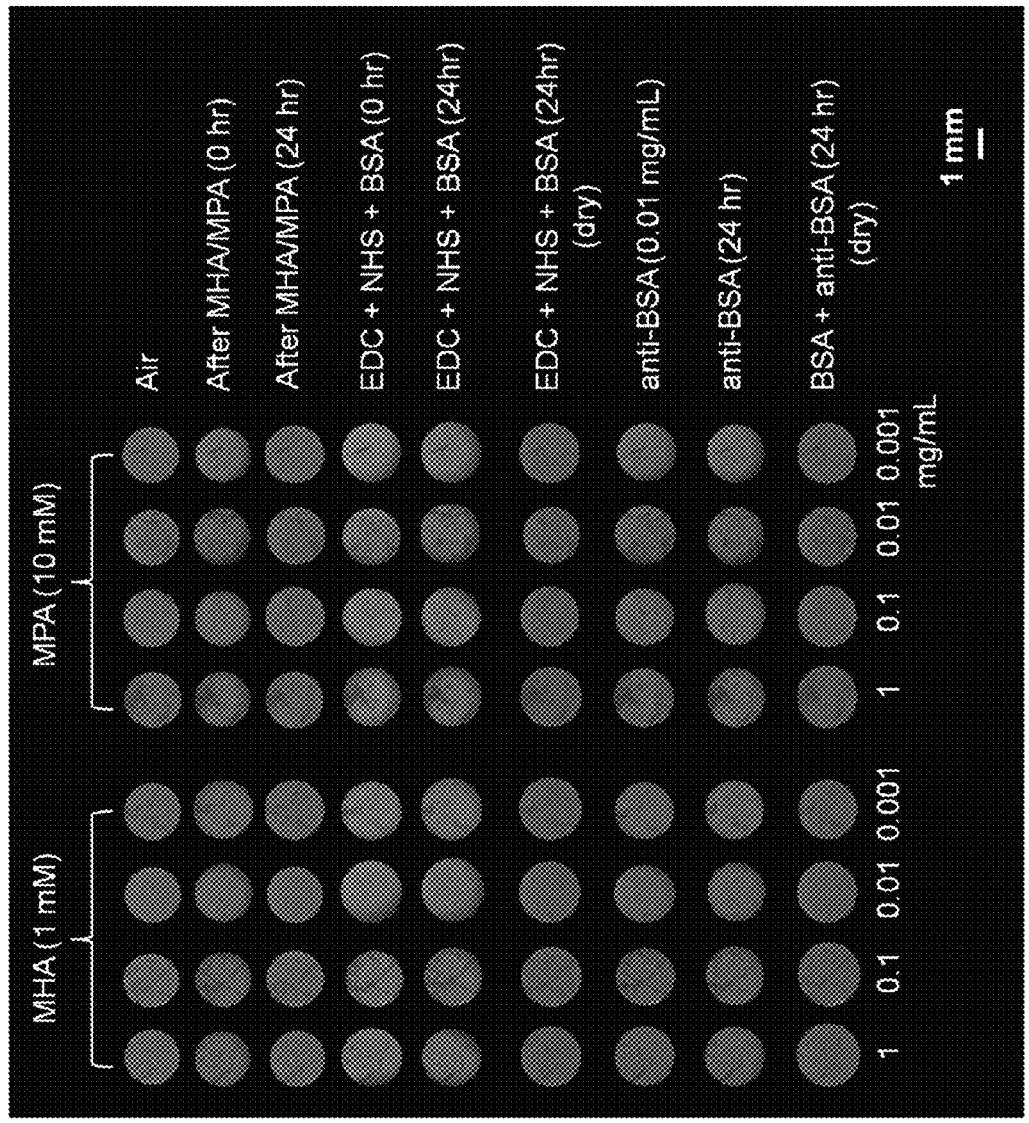
FIG. 19 shows bright field images of BSA and anti-BSA a sensor according to one example embodiment. The surface of the sensor was carboxylated using ethanolic solution of 3-Mercaptopropionic acid (MPA) (10 mM) and 6-Mercaptohexanoic acid (MHA) (1 mM). The bright field images of the example sensor are shown after each step.
Figure 20A:
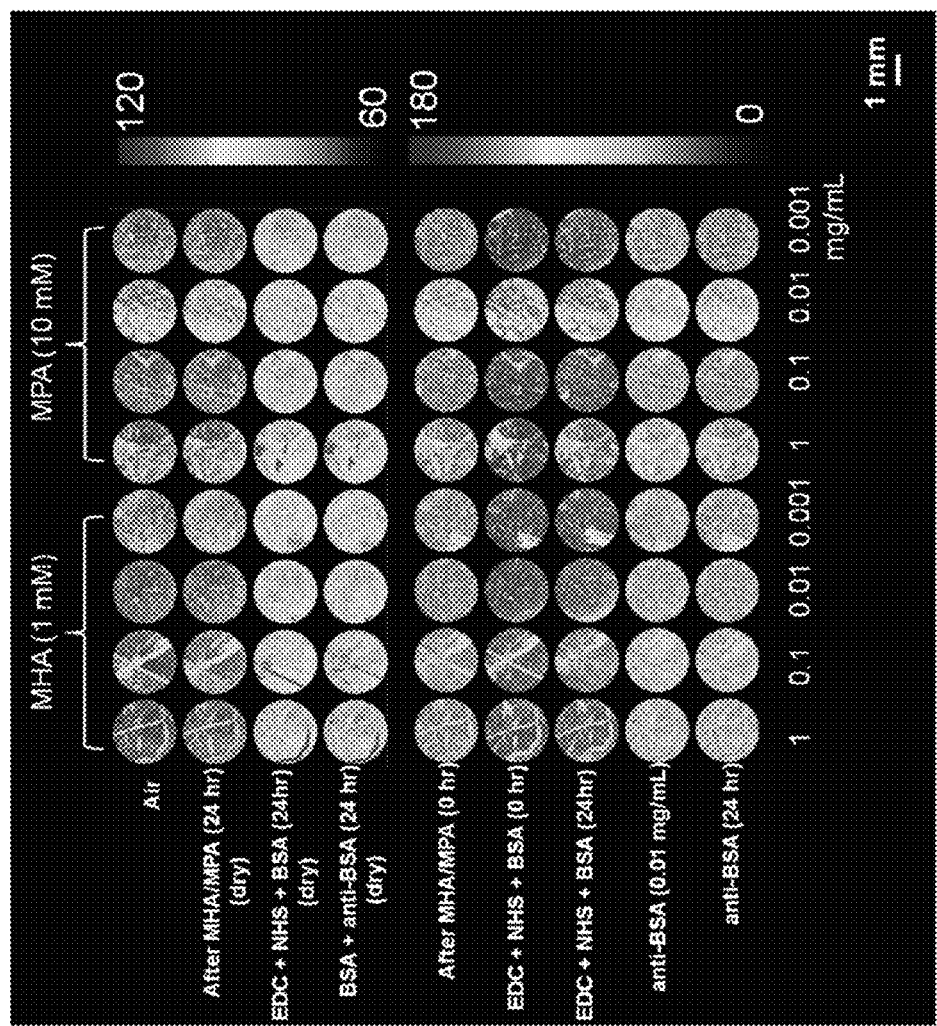
FIG. 20A shows a MATLAB analysis of the example sensors of FIG. 19 showing the red channel intensity distribution.
Figure 20B:
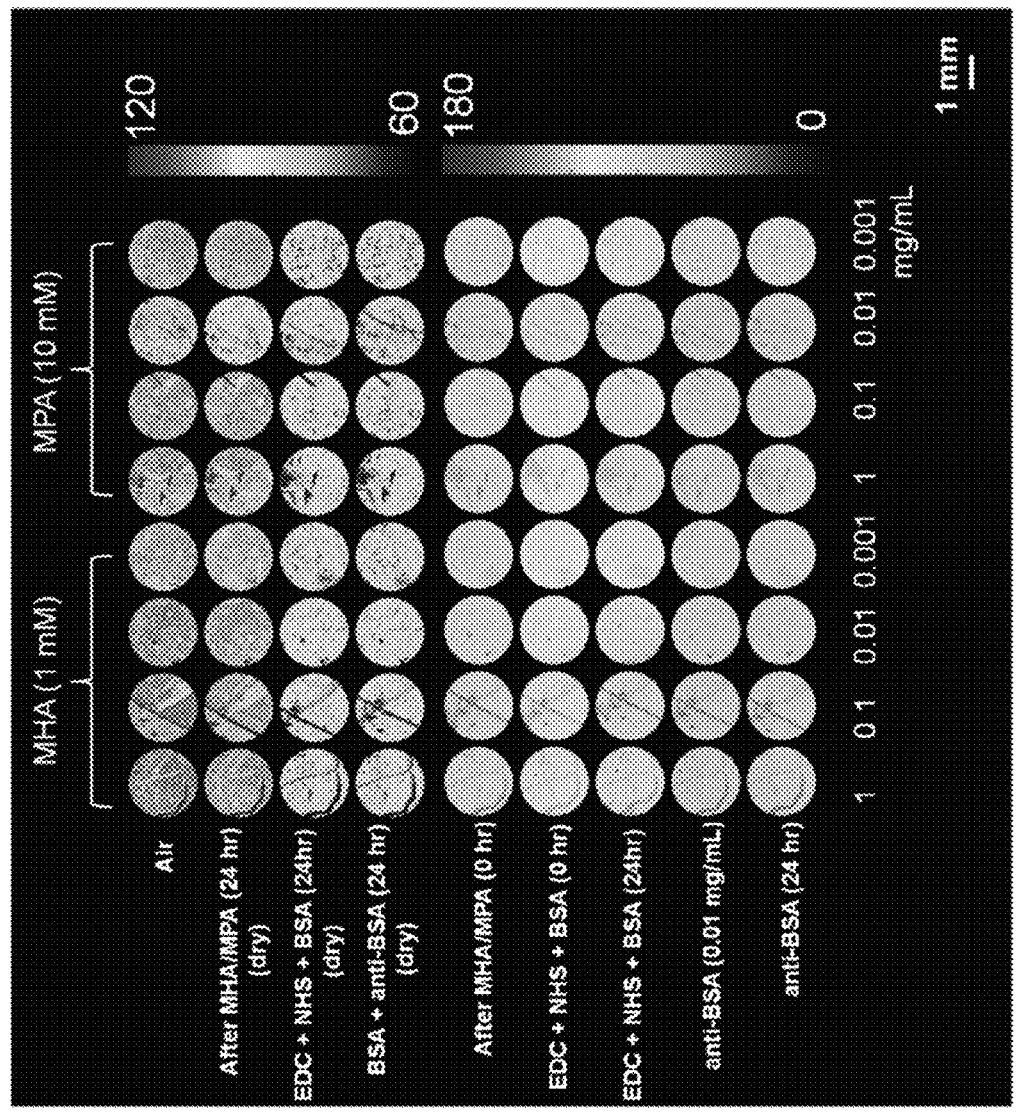
FIG. 20B shows a MATLAB analysis of the example sensors of FIG. 19 showing the green channel intensity distribution.
Figure 21:
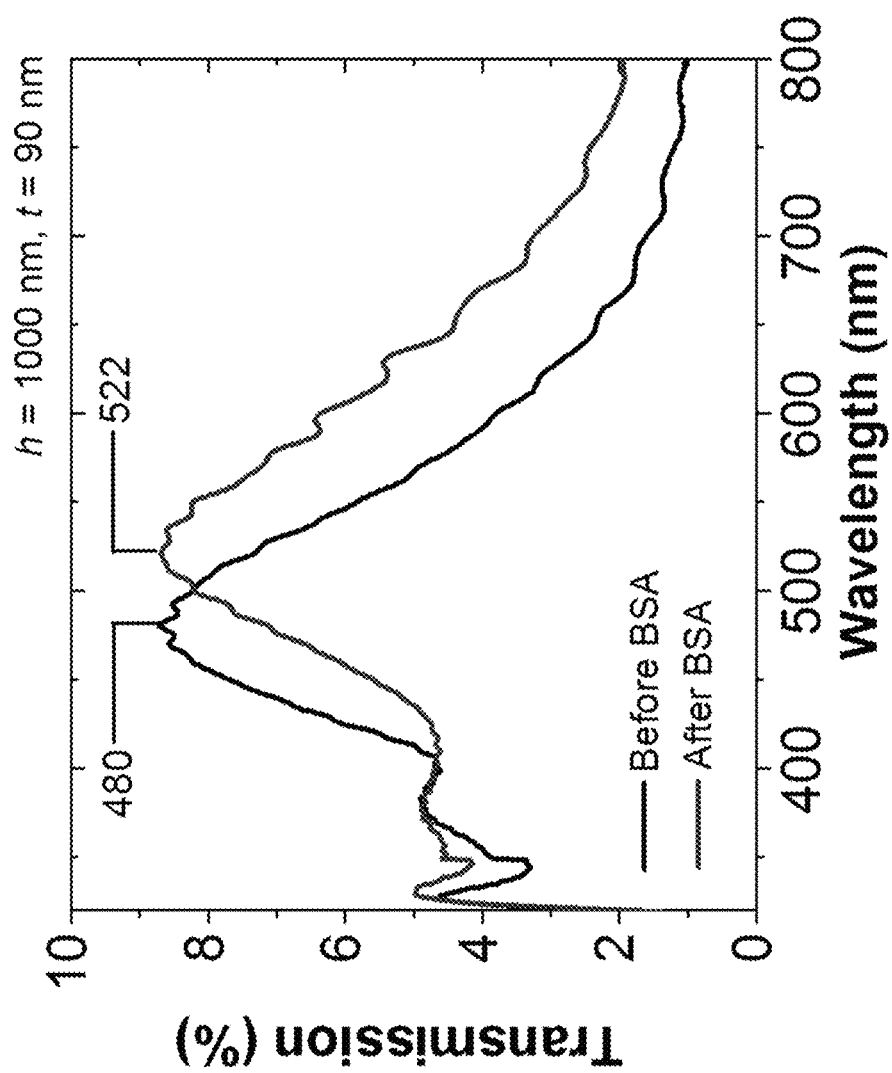
FIG. 21 shows a graph illustrating the transmission spectrum of an example embodiment of a sensor having nanoholes with height h=1000 nm before and after immobilizing BSA on the surface of the sensor. The concentration of BSA solution was 10 μM.

Furthermore, a simple biomolecular protein-protein interaction experiment was performed to demonstrate the therapeutic antibody screening functionality on the nanoLCA sensor. Color changes were observed on the sensor surface (raw images are shown in FIG. 19) due to BSA/anti-BSA immune complex formation which is also relevant to the studies related to the receptor sites of red blood cells. As shown in FIG. 6A (top is red channel intensity, bottom is for green channel intensity), before and after immune complex formation can be clearly discerned for different concentration of BSA/anti-BSA from the nanoLCA sensor imaging data (see Methods and FIGS. 20A-B). The spectral shift observed for the nanoLCA structure after BSA modification was ~42 nm, as shown in FIG. 21. For a similar experiment, resonant wavelength shift of ~5 nm was observed, which is 8.4 times lower than in the case of nanoLCA structure (even without optimization). In the colorimetric analysis, a decrease in the intensity of the red and green channels was observed following the BSA/anti-BSA complex formation. Further, in a previously reported experiment using an EOT plasmonic structure, only reduction of transmitted intensities after antibody adsorption to the surface was observed (the color was changed from red (before protein incubation) to black (after protein incubation)). In contrast, nanoLCA sensor leads to a change in color after protein adsorption due to the higher sensitivity of the device. The DNA and BSA experiments were performed in a 96-well microplate. The experiment has also been performed with microfluidics to show that the nanoLCA sensor may be integrated with a microfluidic device. FIG. 6B shows the BF image of the nanoLCA sensor with a polydimethylsiloxane ("PDMS") microfluidic device disposed on top of the sensor. At the contact point of the PDMS to the surface of the nanoLCA sensor, a color change is observed (green is in contact with air, red is in contact with PDMS). An added advantage of nanoLCA is that the proper contact of the device to the microfluidic surface can be checked even before the actual experiments. FIG. 6B also shows the mixing experiments with glycerol-water and DMSO-water solution to demonstrate the gradient change in color due to different concentrations of solutions in a microfluidic-on-nanoLCA environment.

Experimental

Fabrication of NanoLCA:

The nanocone master made on glass substrate was passivated with dimethyl dichlorosilane solution for 30 minutes, followed by ethanol and deionized water rinse. This step promotes the formation of a hydrophobic silane layer on the master which helps in the removal of cured polymer replica. A 250 µm thick flexible (Poly)ethylene terephthalate (PET) sheet was used as a supporting substrate, and a Teflon roller was used for evenly distributing the UV curable polymer on the master and PET interface. In order to cure the UV polymer, a UV light-curing flood lamp system (Dymax EC-Series) with average power density of 105 mW cm$^{-2}$ was used. The polymer was cured by UV light for 60 s at room temperature. For the metal (Ag, Au) evaporation a six pocket e-beam evaporation system (Temescal) was used. A thin adhesive layer of Titanium (5 nm) was deposited before the evaporation of Ag/Au.

Optical Characterization:

NanoLCA transmission spectra were collected using Varian Cary 5G UV-Vis-NIR spectrophotometer (spectral bandwidth=1 nm, data interval=1 nm) with normal incidence transmission mode. The angle and polarization dependent transmission spectra were obtained by J.A. Woollam Co. variable angle spectroscopic ellipsometer. For the dispersion diagram (angle-wavelength), the transmission spectra were taken at 1° intervals. The reflectance spectra were obtained in an inverted microscope (Zeiss Axio Observer D1) equipped with 100 W halogen light source. The light was focused on to the sample with 20× objective (NA=0.45) and the reflected light were collected by a silicon photodiode array (PDA) spectrometer (300-900 nm).

Image Analysis:

The color images of the nanopore devices were captured using a transmission light microscope with 5× magnification (Olympus, Center Valley, Pa., USA) with exposure time of 40 ms (gain=1; gamma=1). Each image is composed of three 8-bit channels of red, green, and blue, and therefore, each color image is 24-bit. For the calculation of mean intensity, an area of the 300×300 pixels (approximately 0.44 mm by 0.44 mm) was cropped from the original image to remove the boundary areas. The raw microscope images were split into three red, green, and blue (RGB) channels. The mean $$\left(\mu = \sum_{i=1}^{N} x_i/N\right),$$

standard deviation $$\left(\delta = \left(\frac{1}{N-1}\sum_{i=1}^{N}(x_i-\mu)^2\right)^{1/2}\right),$$

and mode of the intensity of the cropped area for each component were determined by the built-in MATLAB R2011b functions (MathWorks, Natick, Mass., USA). Earth's mover distance (EMD) algorithm was implemented to compute the flow that minimizes the overall ground distance between two signatures, $S_A$ and $S_B$. Each signature, $S_x = \{(x_1, w_{x1}), \ldots, (x_M, w_{xM})\}$, consists of m clusters with $x_i$, a cluster representative, and $w_{xi}$, the weight of the cluster. The distance, $d_{ij}$, is the vector norm (ground distance) between clusters $a_i$ and $b_j$. For each RGB channel, the signature consists of the binned (N=100) intensity of the pixels in the cropped area and the weights of the bins, which were calculated as the number of pixels in the bin divided by the total number of pixels. In EMD calculation, the flow, f, between the clusters $a_i$ and $b_j$, is calculated to minimize the overall work function:

$$\text{WORK}(A, B, F) = \sum_{i=1}^{M}\sum_{j=1}^{M} d_{ij} f_{ij}.$$

After the overall work function has been minimized, the EMD is calculated as:

$$\text{EMD}(A, B) = \sum_{i=1}^{M}\sum_{j=1}^{N} d_{ij} f_{ij} \bigg/ \sum_{i=1}^{M}\sum_{j=1}^{N} f_{ij}.$$

In the EMD calculation of RGB images, the signature of DI water was compared to itself (as a negative control) and the signature of other dissimilar solutions.

FDTD Simulations:

The 3D finite difference time-domain (FDTD) analysis was performed using a commercial software package (FDTD solutions, Lumerical Solutions, Inc. Vancouver, Canada). A unit magnitude plane wave with normal incidence angle, polarized in x-direction and propagating in +z direction was used for exciting the modes in nanoLCA. A uniform mesh size of 1 nm (x, y, z-directions) was used. The optical constants of Ag in the spectral range of 300-1100 nm were taken from Palik's handbook. In order to properly calculate the angular and wavelength dependent transmission spectra, perfectly matched layers (PMLs) are imposed at boundaries normal to the light propagation directions. Similarly, the boundary conditions in x and y directions were set as periodic.

Numerical Calculations:

For the SPP-BW calculation, the dielectric constant of Ag is calculated with a Drude plus two-pole Lorentzian form as:

$$\varepsilon_{Ag}(\omega) = \varepsilon_\infty - \frac{\omega_D^2}{\omega^2 + i\gamma_D\omega} - \sum_{m=1}^{2} \frac{g_{L_m}\omega_{L_m}^2 \Delta\varepsilon}{\omega^2 - \omega_{L_m}^2 + i2\gamma_{L_m}\omega}$$

where, $\varepsilon_\infty = 2.3646$, $\omega_D = 8.7377$ eV, $\gamma_D = 0.07489$ eV, $\Delta\varepsilon = 1.1831$, $g_{L_1} = 0.2663$, $\omega_{L_1} = 4.3802$ eV, $\gamma_{L_1} = 0.28$ eV, $g_{L_2} = 0.7337$, $\omega_{L_2} = 5.183$ eV and $\gamma_{L_2} = 0.5482$ eV. The Mie scattering calculation for the metal nanoparticles are performed using Lorenz-Mie theory ("MiePlot v 4.2.05" by Philip Laven) (http://www.philiplaven.com/mieplot.htm).

Materials:

The UV curable polymer (NOA 61) was obtained from Norland Products, Cranbury, N.J. Polydimethylsiloxane (PDMS) (Dow Corning, Midland, Mich.). Micro-channels were prepared using a 10:1 v/v ratio of base to curing agent and the polymer was cured at 65° C. for 1 hour. Glycerol, NaCl and Glucose were purchased from Sigma and used without any modification. The custom made DNA sequences were obtained from Alpha DNA and used without any purification. The DNA was diluted with DI water for making different concentrations of DNA solution. For hybridization experiments, 1× Phosphate Buffer Solution (PBS) solution was used for the dilution of target DNA (HEX modified probe). Albumin from bovine serum (BSA), Anti-Bovine Albumin (anti-BSA), N-Hydroxysuccinimide (NHS) and N-(3-Dimethylaminopropyl)-N'-ethylcarbodiimide hydrochloride (EDC) were obtained from Sigma-Aldrich.

DNA Hybridization Experiments:

Two sets of DNA hybridization experiment were performed. In one experiment, the concentration of 'probe' DNA (5'-thiol-CAGCAAATGGGCTCCGAC-3'; hereafter called "DNA-1"; SEQ ID NO: 01) was prepared from 100 nM to 100 μM and the concentration of 'target' DNA (3'-GTCGGAGCCCATTTGCTG-5'-HEX; hereafter called "DNA-2"; SEQ ID NO: 02) was kept constant (10 μM). In the second experiment, concentration of DNA-1 was kept constant (100 nM) and the concentration of DNA-2 was prepared from 100 μM to 100 nM. The nanoLCA devices were first attached to the bottom of 96-well microplate (4 wells for the samples and 4 wells as duplicates). Transmission and reflection mode bright field (BF) images of each well were taken. Then 100 μL of DNA-1 solution (in DI water) was put in each well and imaged immediately. The DNA-1 solution was kept in a humidity controlled chamber for 24 hours to allow the immobilization of oligo to the Ag surface through thiol chemistry. Images were taken after 24 hours in wet state. The DNA-1 that is not bound to the surface was removed by washing thoroughly with DI water and the surface was dried by N2 blow gun and immediately BF images were taken. Similarly, the nanoLCA sensors were immersed in 100 μL of DNA-2 solutions, imaged immediately, incubated for 24 hours, imaged again, washed and dried, and imaged subsequently, both in BF and fluorescence imaging mode.

Protein-Protein Binding Experiments:

In order to make carboxylated monolayer and thiol linker on the surface, 3-Mercaptopropionic acid (MPA) (10 mM) and 6-Mercaptohexanoic acid (MHA) (1 mM) in anhydrous ethanol solution were used. Immobilization of protein (BSA) to the surface was achieved by linking one of the amine functional groups on protein to the carboxyl group through a peptide bond (amide linkage) in the presence of catalyst N-(3-Dimethylaminopropyl)-N'-ethylcarbodiimide hydrochloride (EDC) (50 mM) and N-Hydroxysuccinimide (NHS) (200 mM). Different concentrations of BSA solution (0.001-1 mg/mL) were prepared in DI water. The concentration of anti-BSA solution prepared in 1× Phosphate Buffer Saline (PBS) was kept constant (0.01 mg/mL). Images were taken at each step (before addition of solution, after addition of solution and after washing and drying).

7. The apparatus of claim 1, further comprising a light source.

8. The apparatus of claim 7, wherein the light source comprises an LED screen or one or more point LEDs.

9. The apparatus of claim 1, further comprising a microfluidic device disposed on the top surface of the array layer.

10. The apparatus of claim 9, wherein the microfluidic device comprises a plurality of channels defined in a base,

We claim:

1. An apparatus, comprising:
   an array layer having a top surface and a bottom surface, wherein a plurality of nanoholes are defined in the top surface of the array layer, wherein the plurality of nanoholes each have at least one sidewall surface and a bottom surface;
   a thin metal film disposed on the top surface of the array layer and on the bottom surface of each of the plurality of nanoholes; and
   a plurality of nanoparticles disposed on the at least one sidewall surface of the plurality of nanoholes.

2. The apparatus of claim 1, wherein the plurality of nanoholes each have frustoconical shape.

3. The apparatus of claim 1, wherein the plurality of nanoparticles are arranged in a discontinuous manner.

4. The apparatus of claim 1, wherein the plurality of nanoparticles comprise metal.

5. The apparatus of claim 1, wherein the thin metal film and the plurality of nanoparticles comprise gold, silver, aluminum, copper, platinum or alloys thereof.

6. The apparatus of claim 1, further comprising a substrate layer having a top surface and a bottom surface, wherein the bottom surface of the array layer is disposed on the top surface of the substrate.

wherein the plurality of channels each have an inlet at a first end and an outlet at a second end, wherein the base is transparent or translucent.

11. The apparatus of claim 1, wherein the array layer is transparent or translucent.

12. The apparatus of claim 1, further comprising a computing device having a camera.

13. The apparatus of claim 12, wherein the computing device comprises a mobile phone.

14. An apparatus, comprising:
   a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes;
   a light source having a light emitting surface;
   a computing device having a camera;
   a housing having a first end and a second end and having at least one sidewall extending between the first end and the second end of the housing, wherein the at least one sidewall defines a chamber, wherein the at least one sidewall is opaque, wherein the at least one sidewall defines a slot at a location between the first and second ends of the housing, wherein the slot is configured to permit ingress and egress of the sensor within the chamber, wherein the first end of the housing may be coupled to a base, wherein the light emitting surface of the light source is arranged within or beneath the base, wherein the base is configured to permit light from the light emitting surface to reach a bottom surface of the sensor, wherein the second end of the housing is configured to receive the computing device and position the camera in line with a top surface of the sensor.

15. The apparatus of claim 14, wherein the sensor further comprises a microfluidic device disposed on the top surface of the array layer.

16. An apparatus, comprising:
a plate defining a plurality of wells; and
a plurality of sensors each disposed within one of the plurality of wells, wherein each sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes.

17. A method of detecting at least one target analyte, comprising:
providing at least one sensor, wherein the at least one sensor comprises a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes;
receiving, by the sensor, at least one target analyte adjacent to a top surface of the sensor;
receiving, by the sensor, a broadband light transmission;
in response to receiving a broadband light transmission, the sensor transmitting or reflecting a specific wavelength of light, wherein the specific wavelength of light is a function of a refractive index of the at least one target analyte; and
causing, by the sensor, a shift in the specific wavelength of transmitted or reflected light, wherein the at least one target analyte is detected.

18. The method of claim 17, further comprising:
measuring the shift in the specific wavelength of light.

19. The method of claim 17, further comprising:
binding of the at least one target analyte to the thin metal film of the sensor.

20. A method of analysis of an image of a sensor, comprising:
receiving, by a computing device, a message providing instructions to capture an image of a sensor, wherein the sensor comprises (i) an array layer having a top surface and a bottom surface, wherein a plurality of nanoholes are defined in the top surface of the array layer, wherein the plurality of nanoholes each have at least one sidewall surface and a bottom surface, (ii) a thin metal film disposed on the top surface of the array layer and on the bottom surface of each of the plurality of nanoholes and (iii) a plurality of nanoparticles disposed on the at least one sidewall surface of the plurality of nanoholes;
capturing, by the computing device, an image of the sensor that is transmitting or reflecting light;
receiving, by the computing device, a message indicating the concentration of a target analyte that is disposed on a top surface of the sensor;
analyzing, by the computing device, the image of the sensor;
receiving, by the computing device, a message requesting that analytical data for the image of the sensor be displayed; and
displaying, by the computing device, the results of the analysis.

* * * * *

UNITED STATES PATENT AND TRADEMARK OFFICE
CERTIFICATE OF CORRECTION

| | | |
|---|---|---|
| PATENT NO. | : 9,464,985 B2 | Page 1 of 1 |
| APPLICATION NO. | : 14/156836 | |
| DATED | : October 11, 2016 | |
| INVENTOR(S) | : Liu et al. | |

It is certified that error appears in the above-identified patent and that said Letters Patent is hereby corrected as shown below:

In Statement of United States Government Contract, delete "The invention described herein was made by an agency of the United States Government or under a contract with an agency of the United States Government. The name of the U.S. Government agency and the Government contract numbers are: Department of Energy DE-G02-07ER 46453; DE-FG02-07ER 46471 and DE-AC52-07NA27344/B598612." insert -- The invention was made with governmental support under grant numbers DE-G02-07ER 46453; DE-FG02-07ER 46471 and DE-AC52-07NA27344/B598612 awarded by the Department of Energy. The government has certain rights in the invention. --

Signed and Sealed this
Tenth Day of April, 2018

Andrei Iancu
*Director of the United States Patent and Trademark Office*